US010475539B2

(12) United States Patent
Rubenstein et al.

(10) Patent No.: US 10,475,539 B2
(45) Date of Patent: Nov. 12, 2019

(54) SYSTEMS AND METHODS FOR PREDICTING TREATMENT-REGIMEN-RELATED OUTCOMES

(71) Applicant: Inform Genomics, Inc., Boston, MA (US)

(72) Inventors: Ed Rubenstein, Boston, MA (US); Stephen T. Sonis, Boston, MA (US); Carl De Moor, Boston, MA (US)

(73) Assignee: Inform Genomics, Inc., Boston, MA (US)

( * ) Notice: Subject to any disclaimer, the term of this patent is extended or adjusted under 35 U.S.C. 154(b) by 0 days.

(21) Appl. No.: 15/953,544

(22) Filed: Apr. 16, 2018

(65) Prior Publication Data

US 2018/0233230 A1   Aug. 16, 2018

Related U.S. Application Data

(63) Continuation of application No. 15/939,621, filed on Mar. 29, 2018, which is a continuation of application No. PCT/US2016/054355, filed on Sep. 29, 2016.

(60) Provisional application No. 62/234,763, filed on Sep. 30, 2015.

(51) Int. Cl.
*G16H 50/20* (2018.01)
*G06N 20/00* (2019.01)
(Continued)

(52) U.S. Cl.
CPC ............. *G16H 50/20* (2018.01); *G06N 20/00* (2019.01); *G16H 50/30* (2018.01); *G16H 50/50* (2018.01); *G06N 5/025* (2013.01)

(58) Field of Classification Search
CPC ........ G16H 20/00; G16H 50/20; G16H 50/30; G16H 50/50; G16H 80/00; G06F 19/30;
(Continued)

(56) References Cited

U.S. PATENT DOCUMENTS

| 6,658,396 B1* | 12/2003 | Tang | G01N 33/5091 706/17 |
| 2002/0077756 A1* | 6/2002 | Arouh | G01N 33/5091 702/20 |

(Continued)

FOREIGN PATENT DOCUMENTS

| WO | WO-2009067473 A2 * | 5/2009 | ........... C12Q 1/6883 |
| WO | 2012009382 A2 | 1/2012 | |
| WO | 2013090620 A1 | 6/2013 | |

OTHER PUBLICATIONS

Shipp, Margaret A et al.; Diffuse large B-cell lymphoma outcome prediction by gene-expression profiling and supervised machine learning; 2002; Nature Publishing Group; Nature Medicine, vol. 8, No. 1; pp. 68-74. (Year: 2002).*

(Continued)

*Primary Examiner* — Stanley K. Hill
(74) *Attorney, Agent, or Firm* — Jones Day

(57) ABSTRACT

Systems and methods are provided for predicting treatment-regimen-related outcomes (e.g., risks of regimen-related toxicities). A predictive model is determined for predicting treatment-regimen-related outcomes and applied to a plurality of datasets. An ensemble algorithm is applied on result data generated from the application of the predictive model. Treatment-regimen-related outcomes are predicted using the predictive model. A combination of machine learning prediction and patient preference assessment is provided for enabling informed consent and precise treatment decisions.

13 Claims, 48 Drawing Sheets

(51) Int. Cl.
G16H 50/30 (2018.01)
G16H 50/50 (2018.01)
G06N 5/02 (2006.01)

(58) Field of Classification Search
CPC ......... G06F 19/32; G06F 19/34; G06Q 50/22; G06Q 50/24
See application file for complete search history.

(56) References Cited

U.S. PATENT DOCUMENTS

| | | | | |
|---|---|---|---|---|
| 2011/0202486 | A1* | 8/2011 | Fung | G06N 7/005 706/12 |
| 2014/0080731 | A1 | 3/2014 | Davicioni et al. | |
| 2015/0186596 | A1* | 7/2015 | Chakrabarti | G06F 19/24 702/19 |

OTHER PUBLICATIONS

Tan, Aik Choon et al.; Ensemble machine learning on gene expression data for cancer classification; 2003; Open Mind Journals Limited; Applied Bioinformatics 2003:2(3 Suppl); pp. 1-9. (Year: 2003).*

Ayers, M. et al.; Gene Expression Profiles Predict Complete Pathologic Response to Neoadjuvant Paclitaxel and Fluorouracil, Doxorubicin, and Cyclophosphamide Chemotherapy in Breast Cancer; 2004; American Society of Clinical Oncology; Journal of Clinical Oncology, vol. 22, No. 12; pp. 2284-2293. (Year: 2004).*

Weiss, Jeremy C. et al.; Machine Learning for Personalized Medicine: Predicting Primary Myocardial Infarction from Electronic Health Records; 2012; Association for the Advancement of Artificial Intelligence; AI Magazine Winter 2012. (Year: 2012).*

Abraham, Jean, Guo, Qi, Dorling, Leila, Tyrer, Jonathan, Ingle, Susan, Hardy, Richard, Vallier, Anne-Laure, Hiller, Louise, Burns, Russell, Jones, Linda, Bowden, Sarah, Dunn, Janet, Poole, Christopher, Caldas, Carlos, Pharoah, Paul, Earl, Helena; Replication of Genetic Polymorphisms Reported to be Associated with Taxane-Related Sensory Neuropathy in Patients with Early Breast Cancer Treated with Paclitaxel; Clinical Cancer Research, 20(9); pp. 2466-2475; May 2014.

Beusterien, Kathleen, Grinspan, Jessica, Kuchuk, Iryna, Mazzarello, Sasha, Dent, Susan, Gertler, Stan, Bouganim, Nathaniel, Vandermeer, Lisa, Clemons, Mark; Use of Conjoint Analysis to Assess Breast Cancer Patient Preferences for Chemotherapy Side Effects; The Oncologist, 19(2); pp. 127-134; 2014.

Blinman, Prunella, Duric, Vlatka, Nowak, Anna, Beale, Philip, Clarke, Stephen, Briscoe, Karen, Boyce, Adam, Goldstein, David, Hudson, Malcolm, Stockler, Martin; Adjuvant Chemotherapy for Early Colon Cancer: What Survival Benefits Make It Worthwhile?; European Journal of Cancer, 46(10); pp. 1800-1807; Jul. 2010.

Blinman, Prunella, McLachlan, Sue-Anne, Nowak, Anna, Duric, Vlatka, Brown, Chris, Wright, Gavin, Milward, Michael, Fong, Kwun, Stockler, Martin; Lung Cancer Clinicians' Preferences for Adjuvant Chemotherapy in Non-Small-Cell Lung Cancer: What Makes It Worthwhile?; Lung Cancer, 72(2); pp. 213-218; May 2011.

Blinman, Prunella, King, M., Norman, R., Viney, R., Stockler, Martin; Preferences for Cancer Treatments: An Overview of Methods and Applications in Oncology; Annals of Oncology, 23(5); pp. 1104-1110; May 2012.

Bodurka, D., Jhingran, A., Ramondetta, L., Eifel, P., Crane, C., Phan, A.; Visual Analog Scale (VAS) and Time Trade-Off (TTO) Preferences for Side Effects (SE) of Chemoradiation (chemoXRT): A Comparison of Patients (pts) and caregivers (CG); Abstract; Journal of Clinical Oncology, 28; 2010.

Dubey, Sarita, Brown, Roger, Esmond, Sarah, Bowers, Barbara, Healy, Janet, Schiller, Joan; Patient Preferences in Choosing Chemotherapy Regimens for Advanced Non-Small Cell Lung Cancer; Journal of Supportive Oncology, 3(2); pp. 149-154; Mar. 2005.

Duric, V., Fallowfield, L., Saunders, C., Houghton, J., Coates, A., Stocker, M.; Patients' Preferences for Adjuvant Endocrine Therapy in Early Breast Cancer: What Makes It Worthwhile?; British Journal of Cancer, 93(12); pp. 1319-1323; 2005.

Kilbridge, Kerry, Weeks, Jane, Sober, Arthur, Haluska, Frank, Slingluff, Craig, Atkins, Michael, Sock, Dana, Kirkwood, John, Nease, Robert; Patient Preferences for Adjuvant Interferon Alfa-2b Treatment; Journal of Clinical Oncology, 19(3); pp. 812-823; 2001.

Koedoot, C., De Haan, R., Stiggelbout, A., Stalmeier, P., De Graeff, A., Bakker, P., De Haes, J.; Palliative Chemotherapy or Best Supportive Care? A Prospective Study Explaining Patients' Treatment Preference and Choice; British Journal of Cancer, 89(12); pp. 2219-2226; 2003.

Kuchuk, I., Bouganim, N., Beusterien, K., Grinspan, J., Vandermeer, L., Gertler, S., Dent, S., Song, X., Segal, R., Mazzarello, S., Crawley, F., Dranitsaris, G., Clemons, M.; Preference Weights for Chemotherapy Side Effects from the Perspective of Women with Breast Cancer; Breast Cancer Research and Treatment, 142(1); pp. 101-107; Nov. 2013.

Ryan, Mandy, Farrar, Shelley; Using Conjoint Analysis to Elicit Preferences for Health Care; BMJ, 320(1530); 2000.

Simes, R. John, Coates, Alan; Patient Preferences for Adjuvant Chemotherapy of Early Breast Cancer: How Much Benefit Is Needed?; Journal of National Cancer Institutes Monographs, 30(1); pp. 146-152; Dec. 2001.

Siminoff, Laura, Gordon, Nahida, Silverman, Paula, Budd, Thomas, Ravdin, Peter; A Decision Aid to Assist in Adjuvant Therapy Choices for Breast Cancer; Psycho-Oncology, 15(11); pp. 1001-1013; Nov. 2006.

Stiggelbout, A., De Haes, J.; Patient Preference for Cancer Therapy: An Overview of Measurement Approaches; Journal of Clinical Oncology, 19(1); pp. 220-230; 2001.

Sun, Charlotte, Bodurka, Diane, Donato, Michele, Rubenstein, Edward, Borden, Candice, Basen-Engquist, Karen, Munsell, Mark, Kavanagh, John, Gershenson, David; Patient Preferences Regarding Side Effects of Chemotherapy for Ovarian Cancer: Do They Change Over Time?; Gynecologic Oncology, 87(1); pp. 118-128; Oct. 2002.

Sun, Charlotte, Bodurka, Diane, Weaver, Candice, Rasu, Rafia, Wolf, Judith, Bevers, Michael, Smith, Judith, Wharton, J. Taylor, Rubenstein, Edward; Rankings and Symptom Assessments of Side Effects from Chemotherapy: Insights from Experienced Patients with Ovarian Cancer; Support Care in Cancer, 13(4); pp. 219-227; Apr. 2005.

Sun, Charlotte, Ramondetta, L., Jhingran, A., Eifel, P., Crane, C., Phan, A.; Patient Preferences for Chemoradiation-Related Side Effects; Abstract; Journal of Clinical Oncology, 27; 2009.

Sun, Charlotte, Brown, Alaina, Jhingran, Anuja, Frumovitz, Michael, Ramondetta, Lois, Bodurka, Diane; Patient Preferences for Side Effects Associated with Cervical Cancer Treatment; International Journal of Gynecological Cancer, 24(6); pp. 1077-1084; Jul. 2014.

Thewes, Belinda, Meiser, Bettina, Duric, Vlatka, Stockler, Martin, Taylor, Alan, Stuart-Harris, Robin, Links, Matthew, Wilcken, Nicholas, McLachlan, Sue Anne, Phillips, Kelly-Anne, Beith, Jane, Boyle, Frances, Friedlander, Michael; What Survival Benefits Do Premenopausal Patients With Early Breast Cancer Need to Make Endocrine Therapy Worthwhile?; Lancet Oncology, 6(8); pp. 581-588; Aug. 2005.

Torrance, George, Feeny, David, Furlong, William; Visual Analog Scales: Do They Have a Role in the Measurement of Preferences for Health States?; Medical Decision Making, 21(4); pp. 329-334; Jul.-Aug. 2001.

Torrance, George, Feeny, David; Utilities and Quality-Adjusted Life Years; International Journal of Technology Assessment in Health Care, 5(4); pp. 559-575; Oct. 1989.

Torrance, George; Utility Approach to Measuring Health-Related Quality of Life; Journal of Chronic Diseases, 40 (6); pp. 593-600; 1987.

Zafar, S. Yousuf, Malin, Jennifer, Grambow, Steven, Abbott, David, Kolimaga, Jane, Zullig, Leah, Weeks, Jane, Ayanian, John, Kahn, Katherine, Ganz, Patricia, Catalano, Paul, West, Dee, Provenzale, Dawn; Chemotherapy Use and Patient Treatment Preferences in Advanced Colorectal Cancer: A Prospective Cohort Study; Cancer, 119(4); pp. 854-862; Feb. 2013.

(56) References Cited

OTHER PUBLICATIONS

McWhinney-Glass, Sarah, Winham, Stacey, Hertz, Daniel, Revollo, Jane Yen, Paul, Jim, He, Yijing, Brown, Robert, Motsinger-Reif, Alison, McLeod, Howard; Cumulative Genetic Risk Predicts Platinum/Taxane-Induced Neurotoxicity; Clinical Cancer Research, 19(20); pp. 5769-5776; Oct. 2013.
Won, Hong-Hee, Lee, Jeeyun, Park, Joon Oh, Park, Young Suk, Lim, Ho Yeong, Kang, Won Ki, Kim, Jong-Won, Lee, Soo-Youn, Park, Se Hoon; Polymorphic Markers Associated With Severe Oxaliplatin-Induced, Chronic Peripheral Neuropathy in Colon Cancer Patients; Cancer, 118(11); pp. 2828-2836; Jun. 2012.
Supplementary European Search Report; EP 16852565; dated Apr. 12, 2019.
Kim, Jinseog, Sohn, Insuk, Kim, Dennis, Jung, Sin-Ho; SNP Selection in Genome-Wide Association Studies via Penalized Support Vector Machine with MAX Test; Computational and Mathematical Methods in Medicine, 2013(8); pp. 1-8; Jan. 2013.
Cosgun, Erdal, Limdi, Nita, Duarte, Christine; High-Dimensional Pharmacogenetic Predition of a Continuous Trait Using Machine Learning Technique with Application to Warfarin Dose Prediction in African Americans; Bioinformatic, 27(10); pp. 1384-1389; Mar. 2011.

\* cited by examiner

SYSTEMS AND METHODS FOR PREDICTING TREATMENT-REGIMEN-RELATED OUTCOMES

CROSS-REFERENCE TO RELATED APPLICATIONS

This application is a continuation of U.S. application Ser. No. 15/939,621, filed Mar. 29, 2018, entitled "Systems and Methods for Predicting Treatment-Regimen-Related Outcomes," which is a continuation of Patent Cooperation Treaty Application No. PCT/US2016/054355, filed Sep. 29, 2016, entitled "Systems and Methods for Predicting Treatment-Regimen-Related Outcomes," which claims priority to U.S. Provisional Application No. 62/234,763, filed Sep. 30, 2015, entitled "Systems and Methods for Predicting Treatment-Regimen-Related Outcomes," both of which are incorporated herein by reference in their entireties.

TECHNICAL FIELD

The present disclosure relates generally to the field of risk prediction, and, more specifically, to systems and methods for predicting treatment-regimen-related outcomes using predictive models. The present disclosure describes a combination of machine learning prediction and patient preference assessment to enable informed consent and precise treatment decisions.

BACKGROUND

Cancer, a genetic disease resulting in abnormal proliferation of affected cells, is one of the most common causes of death in many parts of the world. Estimated new cases of cancer in the United States in 2014 were over 1.5 million (excluding nonmelanoma skin cancers), and estimated deaths from cancer were in excess of 500,000.

One cancer treatment option is chemotherapy. Chemotherapy is the use of anticancer drugs to suppress or kill cancerous cells, and is one of the most common treatments for cancer. Tumor cells are characterized by fast growth reproduction, local invasion and distant spread (metastases). In most cases, chemotherapy works by targeting various cell cycle pathways that are used by the tumor cells to promote their growth and spread. A chemotherapeutic drug may be used alone, in combination with one or more other chemotherapeutic drugs, in combination with other treatments such as radiation or surgery, or in combination with biologic agents, targeted agents, immune-therapies or antibody-based therapies. Certain chemotherapy drugs and their combinations may be administered in a specific order depending on the type of cancer it is being used to treat.

Clinical outcomes, such as efficacy and/or side effects (also known as toxicities) of certain medical treatments such as chemotherapy, are important for evaluating or assessing the effect of the treatment regimens. The prediction of the clinical outcomes plays a critical role for developing precision medical treatments. For example, upon diagnosis of cancer and during the planning of treatment options by the physician, additional patient information, such as genetic information or non-genetic information, may help determine the likelihood of a patient developing regimen-related toxicities. Currently there are no precise methods or systems that allow a physician to predict an individual patient's risk of side-effects or toxicities of anticancer regimens. Having such methods or systems would allow for the adoption of precision medicine for treatment of cancer. Predicting efficacy and potential side effects or toxicities based on genetic or other patient information requires an innovative approach because such risk may be associated with combinations of factors including but not limited to networks of genes functioning and interacting together.

SUMMARY

Systems and methods are provided for predicting regimen-related outcomes (e.g., risks of regime-related toxicities). A predictive model is determined for predicting regimen-related outcomes and applied to a plurality of datasets. An ensemble algorithm is applied on result data generated from the application of the predictive model. Regimen-related outcomes are predicted using the predictive model.

According to one embodiment, a processor-implemented method is provided for predicting risk of regimen-related toxicities. The method comprises: generating, using the one or more data processors, one or more training datasets and one or more testing datasets based at least in part on clinical data or gene feature data of a plurality of patients; determining, using one or more data processors, one or more initial predictive models using one or more machine learning algorithms based at least in part on the one or more training datasets; applying, using the one or more data processors, the one or more initial predictive models on the one or more training datasets to generate result data; performing, using the one or more data processors, an ensemble algorithm on the result data to generate ensemble data; determining, using the one or more data processors, one or more final predictive models based at least in part on the ensemble data; evaluating, using the one or more data processors, performance of the one or more final predictive models based at least in part on the one or more test datasets; and predicting, using the one or more data processors, regimen-related outcomes using the one or more final predictive models.

According to another embodiment, a processor-implemented method is provided for building a predictive model for predicting regimen-related outcomes. The method comprises: dividing, using one or more data processors, a training dataset into a plurality of sub-datasets; selecting, using the one or more data processors, one or more first training sub-datasets from the plurality of sub-datasets; determining, using the one or more data processors, a first predictive model using one or more machine learning algorithms based at least in part on the one or more first training sub-datasets; evaluating, using the one or more data processors, the performance of the first predictive model using the plurality of sub-datasets excluding the one or more first training sub-datasets; and determining, using the one or more data processors, a final predictive model based at least in part on the performance evaluation of the first predictive model.

According to yet another embodiment, a processor-implemented system is provided for predicting regimen-related outcomes. The system comprises: one or more processors and one or more non-transitory machine-readable storage media. The one or more processors are configured to: generate one or more training datasets and one or more testing datasets based at least in part on clinical data or gene feature data of a plurality of patients; determine one or more initial predictive models using one or more machine learning algorithms based at least in part on the one or more training datasets; apply the one or more initial predictive models on the one or more training datasets to generate result data; perform an ensemble algorithm on the result data to generate ensemble data; determine one or more final predictive models based at least in part on the ensemble data; evaluate performance of the one or more final predictive models based at least in part on the one or more test datasets; and predict regimen-related outcomes using the one or more final predictive models. The one or more non-transitory machine-readable storage media are provided for storing a computer database having a database schema that includes and interrelates clinical data fields, gene feature data fields, result data fields, ensemble data fields and predictive model data fields. The clinical data fields store the clinical data, the gene feature data fields store the gene feature data, and the result data fields store the result data. The ensemble data fields store the ensemble data, and the predictive model data fields store parameter data of the initial predictive models and the final predictive models.

According to yet another embodiment, a processor-implemented system is provided for building a predictive model for predicting regimen-related outcomes. The system comprises: one or more processors and one or more non-transitory machine-readable storage media. The one or more processors are configured to: divide a training dataset into a plurality of sub-datasets; select one or more first training sub-datasets from the plurality of sub-datasets; determine a first predictive model using one or more machine learning algorithms based at least in part on the one or more first training sub-datasets; evaluate the performance of the first predictive model using the plurality of sub-datasets excluding the one or more first training sub-datasets; and determine a final predictive model based at least in part on the performance evaluation of the first predictive model. The one or more non-transitory machine-readable storage media are provided for storing a computer database having a database schema that includes and interrelates training data fields, first predictive model data fields, and final predictive model data fields. The training data fields store the training dataset, the first predictive model data fields store parameter data of the first predictive model, and the final predictive model data fields store parameter data of the final predictive model.

In some embodiments, a non-transitory computer-readable medium is encoded with instructions for commanding one or more processors to execute operations of a method for predicting regimen-related outcomes. The method comprises: generating one or more training datasets and one or more testing datasets based at least in part on clinical data or gene feature data of a plurality of patients; determining one or more initial predictive models using one or more machine learning algorithms based at least in part on the one or more training datasets; applying the one or more initial predictive models on the one or more training datasets to generate result data; performing an ensemble algorithm on the result data to generate ensemble data; determining one or more final predictive models based at least in part on the ensemble data; evaluating performance of the one or more final predictive models based at least in part on the one or more test datasets; and predicting regimen-related outcomes using the one or more final predictive models.

In certain embodiments, a non-transitory computer-readable medium is encoded with instructions for commanding one or more processors to execute operations of a method for building a predictive model for predicting regimen-related outcomes. The method comprises: dividing a training dataset into a plurality of sub-datasets; selecting one or more first training sub-datasets from the plurality of sub-datasets; determining a first predictive model using one or more machine learning algorithms based at least in part on the one or more first training sub-datasets; evaluating the performance of the first predictive model using the plurality of sub-datasets excluding the one or more first training sub-datasets; and determining a final predictive model based at least in part on the performance evaluation of the first predictive model.

In other embodiments, a non-transitory computer-readable medium is provided for storing data for access by an application program being executed on a data processing system. The storage medium comprises: a data structure stored in said memory, said data structure including information, resident in a database used by said application program. The data structure includes: one or more clinical data objects stored in said memory, the clinical data objects containing clinical data of a plurality of patients from said database; one or more gene feature data objects stored in said memory, the gene feature data objects containing gene feature data of the plurality of patients from said database; one or more training data objects stored in said memory, the training data objects containing one or more training datasets generated based at least in part on the clinical data or the gene feature data; one or more predictive model data objects stored in said memory; one or more initial predictive model data objects stored in said memory, the initial predictive model data objects containing parameters of one or more initial predictive models determined using one or more machine learning algorithms based at least in part on the one or more training datasets; one or more result data objects stored in said memory, the result data objects containing result data generated by applying the initial predictive models on the one or more training datasets; one or more ensemble data objects stored in said memory, the ensemble data objects containing ensemble data generated by performing an ensemble algorithm on the result data; and one or more final predictive model data objects stored in said memory, the final predictive model data objects containing parameters of one or more final predictive models determined based at least in part on the ensemble data. The final predictive model data objects are used by said application program for predicting regimen-related outcomes.

In other embodiments, a non-transitory computer-readable medium is provided for storing data for access by an application program being executed on a data processing system. The storage medium comprises: a data structure stored in said memory, said data structure including information, resident in a database used by said application program. The data structure includes: one or more training data objects stored in said memory, the training data objects containing a training dataset from said database, the training dataset including a plurality of sub-datasets; one or more first predictive model data objects stored in said memory, the first predictive model data objects containing parameter data of a first predictive model determined using one or more machine learning algorithms based at least in part on one or more first training sub-datasets from the plurality of sub-datasets; one or more final predictive model data objects stored in said memory, the final predictive model data objects containing parameter data of a final predictive model determined based at least in part on performance evaluation of the first predictive model. The final predictive model data objects are used by said application program for predicting regimen-related outcomes.

DETAILED DESCRIPTION

1. Overview

Figure 1:
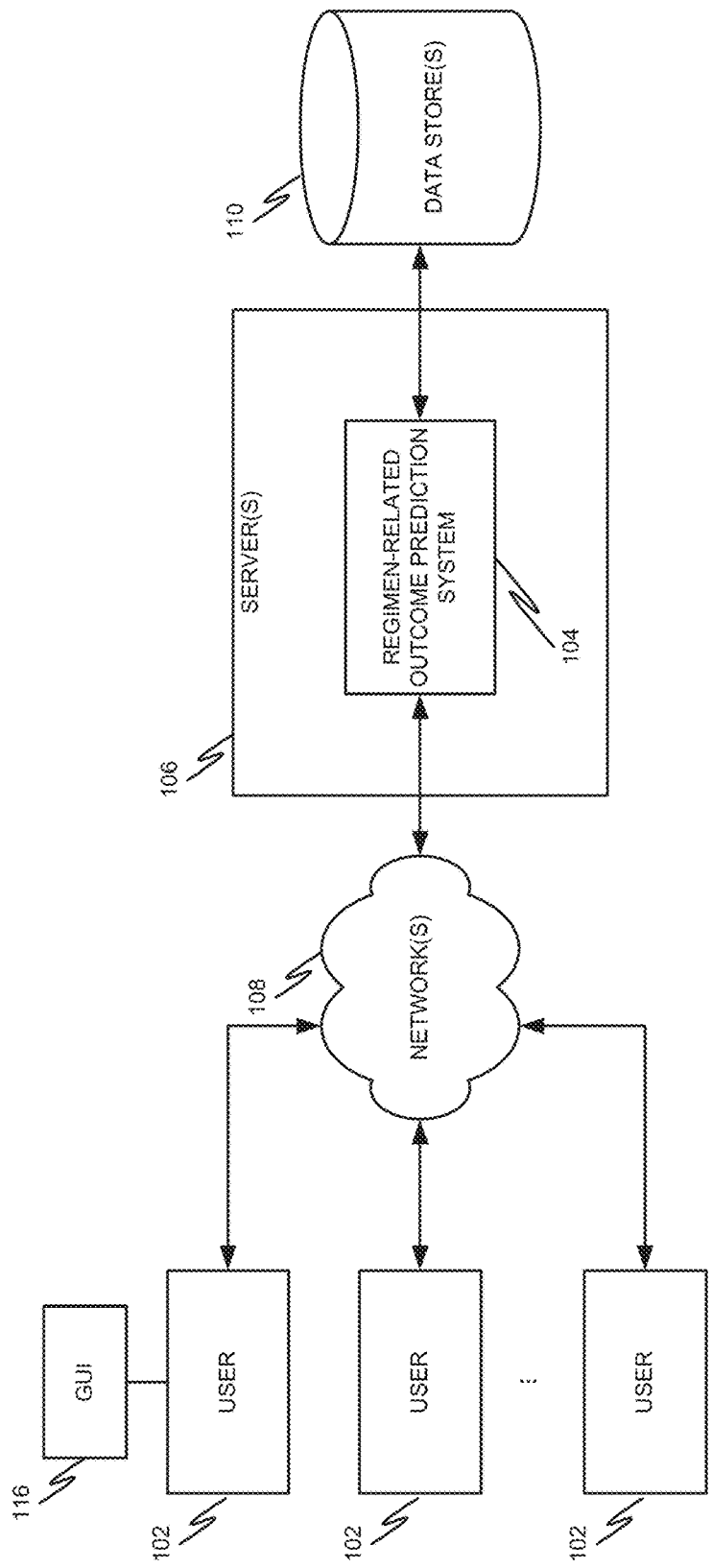
FIG. 1 depicts an example computer-implemented environment wherein users can interact with a regimen-related outcome prediction system hosted on one or more servers through a network.

The present disclosure relates to systems and methods for treating diseases (e.g., cancer) in a subject. For example, cancer encompasses a wide range of conditions, each with a unique disease profile and treatment regimen. After a subject is diagnosed with a certain type of cancer, various chemotherapeutic and anticancer treatment options are considered based on the cancer type and a variety of its genetic makeup and molecular markers. Additional external information about the patient is collected, including, but not limited to medical history, gender, age, ethnicity, hereditary medical information, genetic information, demographic information, environmental information, and other information related to the individual patient. Such information can be obtained using various methods, including at the point of care through questionnaires, from surveys, or from personal health records. One or more sources of such additional information are used as input for a regimen-related outcome prediction tool to predict regimen-related outcomes, such as risks of regimen-related toxicities. A personalized risk profile can be generated and the optimal course of treatment can be determined. It should be understood that the systems and methods described herein are not limited to any particular disease (such as cancer) or any particular treatment regimen.

2. Types of Cancer

The systems and methods provided herein can be used for treating the side effects of a number of cancer types including Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytoma/Malignant Glioma; Craniopharyngioma; Ependymoblastoma; Ependymoma; Medulloblastoma; Medulloepithelioma; Pineal Parenchymal Tumors of Intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma; Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extra gonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; Intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, Intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Cell Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; or Wilms Tumor.

3. Cancer Therapy

Chemotherapy is one of the most widely used treatment method for cancer. Chemotherapy can be used alone or in combination with surgery or radiation therapy, or in combination with other anti-cancer agents. These other anti-cancer agents, which can be used alone or in combination with other treatments, include, but are not limited to, monoclonal antibodies, biologic agents, targeted agents, immunetherapies or antibody-based therapies.

A number of chemotherapeutic agents are available today. These agents include, but are not limited to, alkylating agents, antimetabolites, anti-tumor antibiotics, topoisomerase inhibitors and mitotic inhibitors.

While chemotherapy can be quite effective in treating certain cancers, chemotherapy drugs reach all parts of the body, not just the cancer cells. Because of this, there may be many side effects during treatment, including tissue damage. For example, oxidative stress, caused directly or indirectly by chemotherapeutics (e.g. doxorubicin), is one of the underlying mechanisms of the toxicity of anticancer drugs in noncancerous tissues, including the heart and brain. In addition, extravasation, i.e. the accidental administration of intravenously (IV) infused chemotherapeutic agents into the tissue surrounding the infusion sites, can cause significant injury.

3.1 Types of Chemotherapy

The systems and methods provided herein can be used to predict regimen-related outcomes, including efficacy and toxicity, that can be used by a physician or a patient to tailor a specific treatment regimen in order to optimize the patient's clinical outcomes. For example, a chemotherapeutic agent can be administered to patients to treat virtually any disorder that is now known or that is later discovered to be treatable with such compounds or combinations thereof. These agents include Alkylating agents, Platinum agents, Anthracyclines Antimetabolites, Anti-tumor antibiotics, Topoisomerase inhibitors (such as camptothecin compounds), Podophyllotoxin derivatives, Antimetabolites, antibiotics, anti-tumor antibodies, Taxanes, and Mitotic inhibitors. In particular, chemotherapeutic agents include, but are not limited to Amsacrine, Actinomycin, All-trans retinoic acid, Azacitidine, Azathioprine, belustine, Bleomycin, Bortezomib, Busulfan, Camptosar™ (irinotecan HCL), Carmustine, Carboplatin, Capecitabine, Cisplatin, Chlorambucil, Chlomaphazin, Cyclophosphamide, Cytarabine, Cytosine arabinoside, Dacarbazine, Dactinomycin, Daunomycin, Daunorubicin, Docetaxel, Doxifluridine, Doxorubicin, Epirubicin, Epothilone, Etoposide, Fluorouracil, Gemcitabine, Hycamtin™ (topotecan HCL), Hydroxyurea, Idarubicin, Imatinib, Irinotecan, Ifosfamide, Mechlorethamine, Melphalan, Mercaptopurine, Methotrexate, Mithramycin, Mitomycin, Mitomycin C, Mitoxantrone, Mitopodozide, Navelbine™ (vinorelbine-5'-noranhydroblastine), Nitrogen mustard, Oxaliplatin, Paclitaxel, Pemetrexed, Procarbazine Teniposide, Tioguanine, Topotecan, Trimethylene thiophosphoramide, Uracil mustard, Valrubicin, Vinblastine, Vincristine, Vindesine, and Vinorelbine, and other compounds derived from Camptothecin and its analogues.

3.2 Side Effects of Chemotherapy

Chemotherapy can cause a variety of side-effects/toxicities, and it is imperative to reduce the severity or frequency of certain toxicities associated with the exposure to the chemotherapy in the patient to both alleviate suffering and potentially increase the dose, thus increasing the chance of successful therapy. These toxicities include, but are not limited to, neurotoxicity, nephrotoxicity, ototoxicity, cardiotoxicity, alopecia, fatigue, cognitive dysfunction, diarrhea nausea, vomiting, mucosal toxicities (mucositis of the gastrointestinal tract and vaginitis), xerostomia, infertility, pulmonary toxicity, low white blood cell counts, infection, anemia, low platelet counts with or without bleeding, and renal failure. Some of these toxicities when severe enough can lead to hospitalizations, medical care in an intensive unit and sometimes death. In specific embodiments, the side effects whose severity or frequency may be predicted by the systems and methods provided herein include: chemotherapy-induced peripheral neuropathy (CIPN) (including damages to certain nerves, which may impair sensation, movement, gland or organ function, or other aspects of health, depending on the type of nerves affected), chemotherapy-induced nausea and vomiting (CINV), fatigue, oral mucositis, diarrhea and cognitive dysfunction.

The side effect profiles of chemotherapeutic drugs vary considerably in terms of short- and long-term side effects. Short term side effects include mostly the toxic effects encountered during or shortly after a course of chemotherapy. Long-term side effects include later complications arising after the conclusion of the course of chemotherapy and may last for many months, years or be permanent. The side effect profiles vary by type of drug, dosage and treatment regimen, but there is also considerable variability in side effect profile across patient populations and more specifically individual patients. It is therefore highly desirable to be able to predict the outcomes of a treatment regimen in terms of both short and long term side effects for each individual patient to enable the patient and the physician to make the appropriate choice given the individual patient's circumstances.

4. Obtaining Patient Information

The techniques described herein can be used with all types of patient information or information from healthy individuals (e.g. to generate control groups), including, but not limited to medical history, gender, age, ethnicity, hereditary medical information, genetic information, demographic information, environmental information, and other information related to the individual patient. Such information can be obtained using various methods, including at the point of care through questionnaires, from surveys, or from personal health records.

Genetic information is generated from genetic material that can be collected from patients or healthy individuals in various ways. In one embodiment, the material is a sample of any tissue or bodily fluid, including hair, blood, tissue obtained through biopsy, or saliva. The material can be collected at point of care or at home. When collected at home, the patient or healthy individual may be sent a collection kit accompanied by instructions for collecting the sample and questionnaire. In addition to the genetic sample collection kit, the patient or healthy individual may be sent a unique identifier which is to be used to link the information provided in response to the questionnaire with the genetic material. DNA can be extracted using techniques known in the art.

A number of techniques can be used to obtain genetic information from material samples. These techniques include, but are not limited to, SNP-arrays to detect SNPs, DNA microarrays to determine gene expression profiles, tiling arrays to analyze larger genomic region of interest (e.g. human chromosome), and Nanopore sequencing for cost-effective high-throughput sequencing of the entire genome. It should be understood that the systems and methods described herein may be configured to obtain other types of patient information or information from healthy individuals (e.g. to generate control groups) as input data, including but not limited to, proteomic information, transcriptomic information, and metabolomic information.

5. Predictive Modeling

FIG. 1 depicts an example computer-implemented environment wherein users 102 (e.g., health care providers) can interact with a regimen-related outcome prediction system 104 hosted on one or more servers 106 through a network 108. The regimen-related outcome prediction system 104 can assist the users 102 to build and/or evaluate one or more predictive models for predicting regimen-related outcomes (e.g., risk of regimen-related out toxicities) for treating diseases in a subject. In specific embodiments, the regimen-related outcome prediction system 104 is configured to combine machine learning prediction based on the one or more predictive models and patient preference assessment to enable informed consent and precise treatment decisions.

In some embodiments, the regimen-related outcome prediction system 104 assists the users 102 to obtain genetic information or non-genetic information of certain patients (e.g., by any means known to a skilled artisan) for creating analysis datasets and build one or more predictive models for predicting outcomes of specific treatment regimens. Data handling of genetic information or non-genetic information will be described in detail as in FIG. 2. In certain embodiments, the regimen-related outcome prediction system 104 implements the one or more predictive models to predict outcomes of a specific treatment regimen using genetic or non-genetic information from an individual patient and determine suitability of the treatment regimen for the patient.

In specific embodiments, the regimen-related outcome prediction system 104 builds the one or more predictive models using one or more deterministic models/algorithms. For example, the regimen-related outcome prediction system 104 implements one or more machine learning algorithms, such as penalized logistic regression, random forests, and/or C5.0, for building the one or more predictive models. The modeling building process will be described in detail as in FIG. 3. It should be understood that other known machine learning algorithms may also be implemented for building the one or more predictive models.

In some embodiments, the regimen-related outcome prediction system 104 may assists one or more of the users 102 to build and/or evaluate one or more predictive models through a graphical user interface 116. For example, the users 102 (or the system operator) may provide inputs at the graphical user interface 116 for the regimen-related outcome prediction system 104 to build the one or more predictive models. In certain embodiments, the user inputs may include non-genetic information related to individual patients, such as medical history, gender, age, ethnicity, demographic information, and environmental information. For example, the user inputs may include patient preferences for disease treatments or toxicities. In some embodiments, the regimen-related outcome prediction system 104 may assists one or more of the users 102 to predict regimen-related outcomes using the one or more predictive models through the graphical user interface 116. For example, the regimen-related outcome prediction system 104 may output a personalized risk profile related to a particular disease for an individual patient and the optimal course of treatment of the disease on the graphical user interface 116.

As shown in FIG. 1, the users 102 can interact with the regimen-related outcome prediction system 104 through a number of ways, such as over one or more networks 108. One or more servers 106 accessible through the network(s) 108 can host the regimen-related outcome prediction system 104. The one or more servers 106 can also contain or have access to the one or more data stores 110 for storing data for the regimen-related outcome prediction system 104, or receive input data (e.g., genetic information or non-genetic information) from external sources. It should be appreciated that in alternative embodiments the server 106 may be self-contained and not connected to external networks due to security or other concerns.

Figure 2:
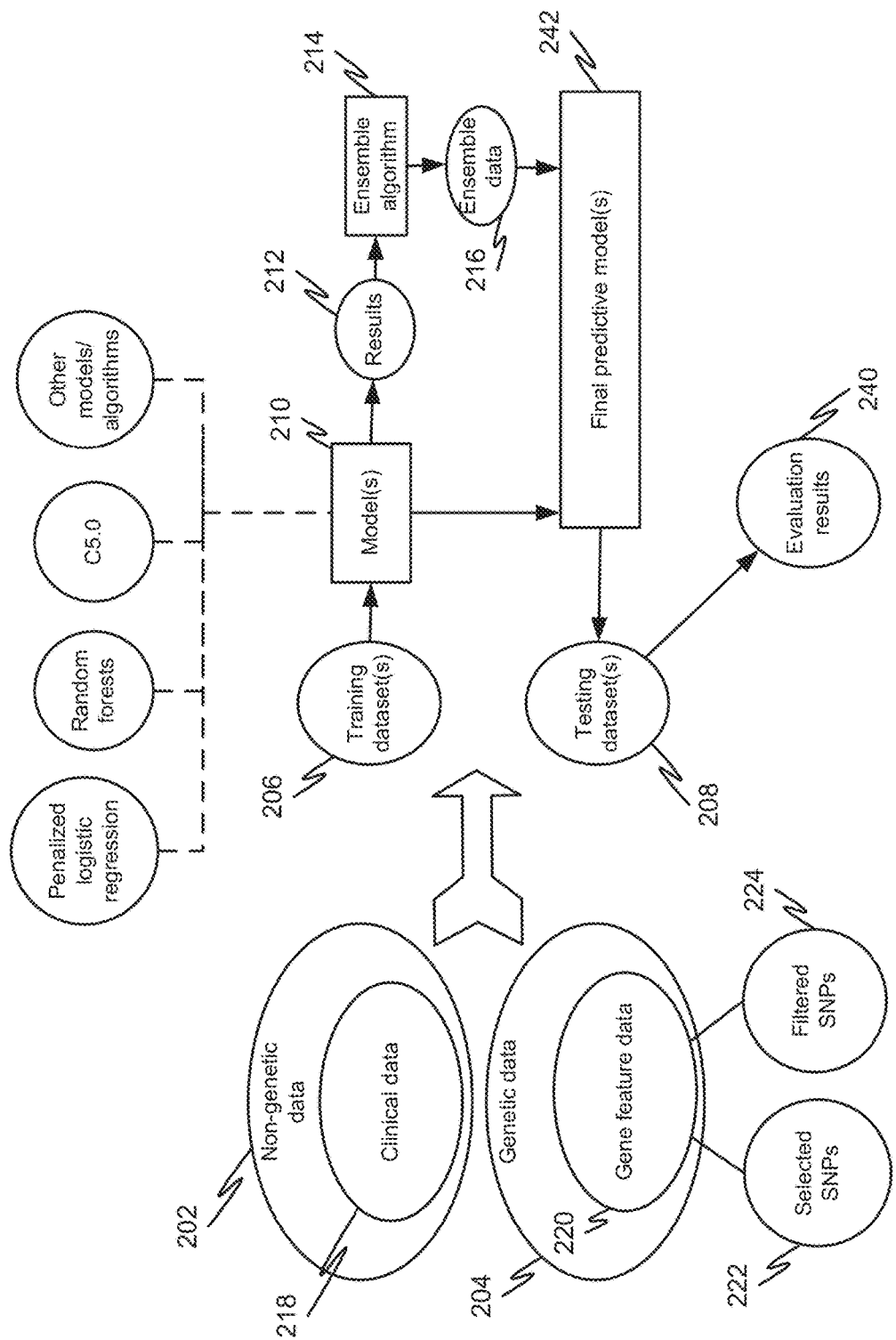
FIG. 2 depicts an example block diagram for building and evaluating predictive models.

FIG. 2 depicts an example block diagram for building and evaluating predictive models. As shown in FIG. 2, non-genetic data 202 and/or genetic data 204 are obtained to generate one or more training datasets 206 and one or more testing datasets 208. One or more models 210 are built using the one or more training datasets 206. Prediction result data 212 of the one or more models 210 based at least in part on the one or more training datasets 206 is given as inputs to an ensemble algorithm 214 for generating ensemble data 216 as a final set of predictions. One or more final predictive models 242 are determined based at least in part on the ensemble data 216. The one or more final predictive models 242 are applied to the one or more test datasets 208 for performance evaluation to generate evaluation results 240. The one or more final predictive models 242 can be applied to new patient data of an individual patient for prediction of regime-related outcomes.

Specifically, a data handling process is performed (e.g., by the regimen-related outcome prediction system 104) to obtain the non-genetic data 202 and/or the genetic data 204. The non-genetic data 202 may include certain clinical data 218 of individual patients which can be used to generate the one or more training datasets 206 and the one or more testing datasets 208. For example, the clinical data 218 includes diagnosis data, cancer-stage data, regimen related data, and neuropathy related data related to individual patients. Binary predictors may be generated by splitting parameters (e.g., diagnosis factors, cancer-stage factors, regimen factors) related to the clinical data 218. In some embodiments, a stratified random approach is used to generate the one or more training datasets 206 and the one or more testing datasets 208 with a numeric regimen categorization and response category so that regimens for affected subjects are proportionally represented in the training datasets and the testing datasets.

In some embodiments, the genetic data 204 includes gene feature data 220, such as data related to one or more SNPs, which can be used to generate the one or more training datasets 206 and the one or more testing datasets 208. In some embodiments, original gene feature data 220 may include a large number of SNPs, and certain pre-processing steps and/or a data filtering process may be performed to determine a limited number of filtered SNPs 224 from the large number of SNPs to simplify and improve the subsequent predictive modeling. For example, the pre-processing steps may include removing certain SNPs due to too much missing data. Also, highly associated SNPs (e.g., contingency table agreement≥0.7) may be removed (e.g., one of each pair of associated SNPs may be removed). It should be understood that other known pre-processing steps may also be performed to ensure data quality.

After the pre-processing steps, the filtering process is performed through recursive partitioning models (e.g., using 10-fold cross-validation) to determine the filtered SNPs 224. Recursive partitioning creates a decision tree that strives to correctly classify members of a dataset by splitting it into sub-datasets based on several dichotomous independent variables. Each sub-dataset may in turn be split an indefinite number of times until the splitting process terminates after a particular stopping criterion is reached. For example, the pre-processed SNP dataset is divided into ten sub-datasets. Nine out of the ten sub-datasets are selected for recursive partitioning modeling which involves building a classification tree. The size of the classification tree is selected by developing recursive partitioning models for each potential tree size on the selected nine sub-datasets. The one sub-dataset other than the selected nine sub-datasets is used to determine the size of the tree that yields a maximum predictive accuracy. Such a process is repeated on each of the possible arrangements of the ten sub-datasets. Any SNPs that are used in any of the recursive partitioning models are kept for predictive modeling. Upon completion of the pre-processing steps and the filtering process, the filtered SNPs 224 are determined for predictive modeling. In specific embodiments, the gene feature data 220 may include one or more selected SNPs 222 (e.g., as identified in Jean E. Abraham et al., Clinical Cancer Research 20(9), May 1, 2014; McWhinney-Glass et al., Clinical Cancer Research 19(20), Oct. 15, 2013; Won et al., Cancer, 118:2828-36, 2012).

As shown in FIG. 2, the one or more training datasets 206 may be generated using the non-genetic data 202 (e.g., the clinical data 218) and/or the genetic data 204 (e.g., the selected SNPs 222, the filtered SNPs 224). The one or more models 210 can be built (e.g., by the regimen-related outcome prediction system 104) using the one or more training datasets 206. In the process of building the models 210, imbalance in the response may influence models to predict samples into the majority class. To adjust for imbalance, the regimen-related outcome prediction system 104 may perform both up-sampling (e.g., selecting additional minority class subjects with replacement to increase the minority class size) and down-sampling (e.g., sampling the majority class to create balance with the minority class). In some embodiments, down-sampling yields better predictive models than up-sampling.

Figure 3:
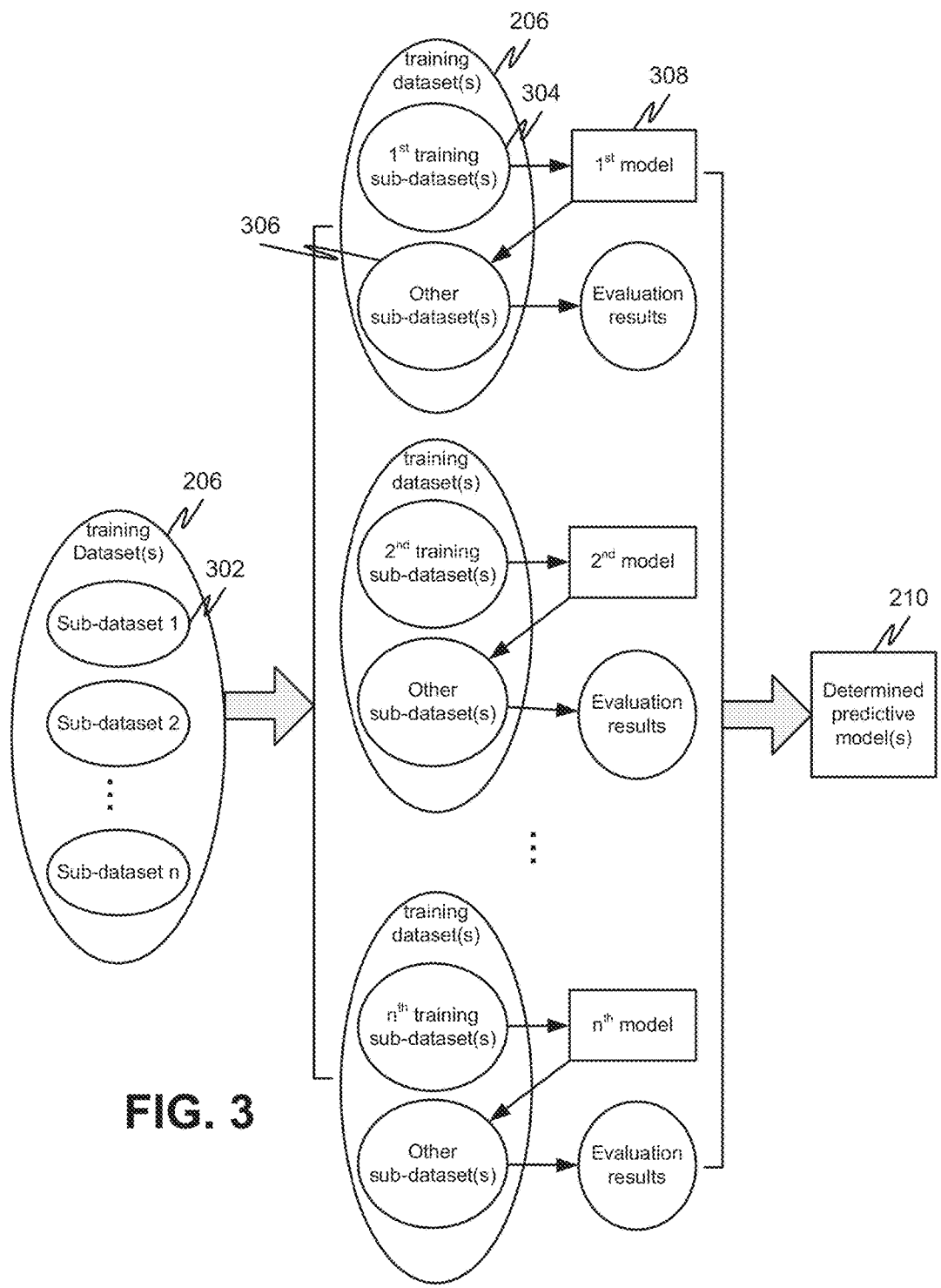
FIG. 3 depicts an example block diagram for model building.

For example, as shown in FIG. 3, the one or more training datasets 206 are divided into a plurality of sub-datasets for exploring different models/algorithms (e.g., machine learning models/algorithms). One or more training sub-datasets 304 are selected from the plurality of sub-datasets 302 for building a model 308. The performance of the model 308 is evaluated using other sub-datasets 306 in the training datasets 206. Such a process is repeated for multiple times, and each time a different group of sub-datasets are selected from the training datasets 206 for building and evaluating a model, until a set of models (e.g., the one or more models 210) are determined. In certain embodiments, five repeats of 10-fold cross-validation are used on the training datasets 206 to determine the optimal tuning parameter setting for the models 210.

One or more machine learning algorithms, including but not limited to, penalized logistic regression, random forests, and/or C5.0, can be applied (e.g., by the regimen-related outcome prediction system 104) on the one or more training datasets 206 for predictive model building (e.g., as shown in FIG. 3). In some embodiments, the penalized logistic regression algorithm can be implemented to find parameter estimates that maximize the objective function (e.g. log-likelihood), subject to regularization constraints. One regularization constraint forces the parameter estimates to be smaller (e.g. shrinkage), while the other regularization constraint essentially forces some parameter estimates to zero (e.g. lasso). The penalized logistic regression algorithm is suited for problems where the predictors are highly correlated or when there are more predictors than subjects. Because the regularization forces some parameter estimates to zero, a predictive model generated based on the penalized logistic regression algorithm performs internal variable selection.

In certain embodiments, the random forests (RF) algorithm is a tree-based method built on an ensemble of trees. A predictive model generated based on the RF algorithm does the following process many times: selects a bootstrap sample of the training dataset and builds a tree on the bootstrap sample. Within each tree, a randomly selected number of predictors are chosen and the optimal split is selected only from that sample. One or more tuning parameters for predictive model generated based on the RF algorithm include the number of randomly selected predictors for each split. Building an ensemble of trees in this way reduces the variance seen by using just a single tree.

In specific embodiments, the C5.0 algorithm can be used to generate a predictive model. Specifically, the C5.0 algorithm is implemented (e.g., by the regimen-related outcome prediction system 104) to build a sequence of trees. At each step in the sequence, the regimen-related outcome prediction system 104 adjusts each sample's weight based on the accuracy of the model at each iteration. Samples that are predicted correctly are given less weight, while samples that are predicted incorrectly are given more weight. The final model prediction is a combination of the predictions across all trees. It should be understood that the systems and methods disclosed herein are not limited to penalized logistic regression, random forests, and C5.0 that are merely described above as examples. Other machine learning algorithms may be implemented for predictive modeling (e.g., as shown in FIG. 3).

In some embodiments, the ensemble algorithm 214 is trained to combine the prediction result data 212 optimally to generate the ensemble data 216. For example, a weight may be determined for the prediction result of each of the models 210, and a weighted sum of the prediction results of all the models 210 is calculated to generate the ensemble data 216.

In certain embodiments, the ensemble algorithm 214 involves an average calculation of the result data 212 generated by applying the models 210 on the training datasets 206. In some embodiments, the ensemble algorithm 214 uses a logistic regression model to combine the result data 212 across models. It should be understood that the ensemble algorithm 214 disclosed herein is not limited to the average calculation and the logistic regression model. The ensemble algorithm 214 may include a stacking technique, a blending technique, or any other known second-level machine learning algorithm in which predictions of a collection of models are combined to form a final set of predictions.

In specific embodiments, the training datasets 206 include a clinical predictor dataset, a selected SNP dataset, and a filtered SNP dataset. Correspondingly, the result data 212 includes clinical predictor result data, selected SNP result data, and filtered SNP result data. The ensemble algorithm 214 can be applied to a combination of these result data. For example, the ensemble algorithm 214 is applied to a combination of the clinical predictor result data and the selected SNP result data, or a combination of the clinical predictor result data, the selected SNP result data, and the filtered SNP result data.

As shown in FIG. 2, the final predictive models 242 are applied to the testing datasets 208 to generate the evaluation results 240. As an example, the evaluation results 240 include sensitivity or specificity parameters for the one or more final predictive models 242. In certain embodiments, the one or more final predictive models 242 provided herein can be used to predict the occurrence of a side effect (such as those listed in Section 3.2) during the treatment of a cancer (such as those listed in Section 2) with a therapy (such as those listed in Section 3.1) with an accuracy of at least 85%, 86%, 87%, 88%, 89%, 90%, 91%, 92%, 93%, 94%, 95%, 96%, 97%, 98%, or at least 99%.

In specific embodiments, the systems and methods disclosed herein (e.g., the regimen-related outcome prediction system 104) are configured to combine model prediction and patient preferences for generating individualized patient reports so that treatment options tailored for individual patients can be determined. For example, patients diagnosed with cancer face important decisions, in partnership with their physicians, regarding chemotherapy options. The patients may weigh the potential clinical benefit against the potential toxicities of the available therapies and their likely effects on quality of life. Patient preferences for cancer therapy incorporate a patient's understanding of the relative benefit and harm of the various alternatives. Understanding a patient's preferences can better inform clinical decision-making.

As an example, three treatment options may be presented to a patient with breast cancer: 1. dose-dense doxorubicin/cyclophosphamide (AC) for four cycles, followed by dose-dense paclitaxel (T) for a first number of weeks with granulocyte-colony stimulating factor (G-CSF) support; 2. dose-dense AC for the first number of weeks for four cycles, followed by paclitaxel (T) weekly for twelve weeks; 3. docetaxel/cyclophosphamide (TC) for a second number of weeks for six cycles. The regimen-related outcome prediction system 104 determines a personalized genomic risk profile related to these three treatment regimens for the patient, e.g., as shown in Table 0. Particularly, each number shown in a particular cell of Table 0 refers to a percentage risk for a corresponding side-effect/toxicity.

TABLE 0

| Chemotherapy | CINV | Oral mucositis | Diarrhea | Cognitive dysfunction | Fatigue | Peripheral neuropathy |
|---|---|---|---|---|---|---|
| 1. Dose-dense AC + T | >90 | <10 | >90 | <10 | 70 | <10 |
| 2. Dose-dense AC + weekly T | >90 | <10 | >90 | <10 | 70 | <10 |
| 3. TC | 50 | >90 | >90 | 30 | 70 | <10 |

As shown in Table 0, the patient has a high risk of CINV for the first treatment option and the second treatment option and a high risk of oral mucositis for the third treatment option. For all three treatment options, the patient has a high risk of diarrhea, a moderate-high risk of fatigue, and a low risk of cognitive dysfunction and peripheral neuropathy.

The informed consent for the treatment regimens may be obtained from the patient based on the risk profile. For example, the patient may be informed of lowering of white blood cells, red blood cells, and platelets (CBC) and associated risks. In addition, the patient may be informed of the risk of CINV, diarrhea, dehydration, electrolyte imbalance, organ damage, fatigue, hair loss, infusion reactions, allergic reactions, etc. Also, the patient may be informed of the risk of cardiac dysfunction due to doxorubicin, bleeding in the bladder due to cyclophosphamide, and other side effects that can be severe and cause death.

Figure 4:
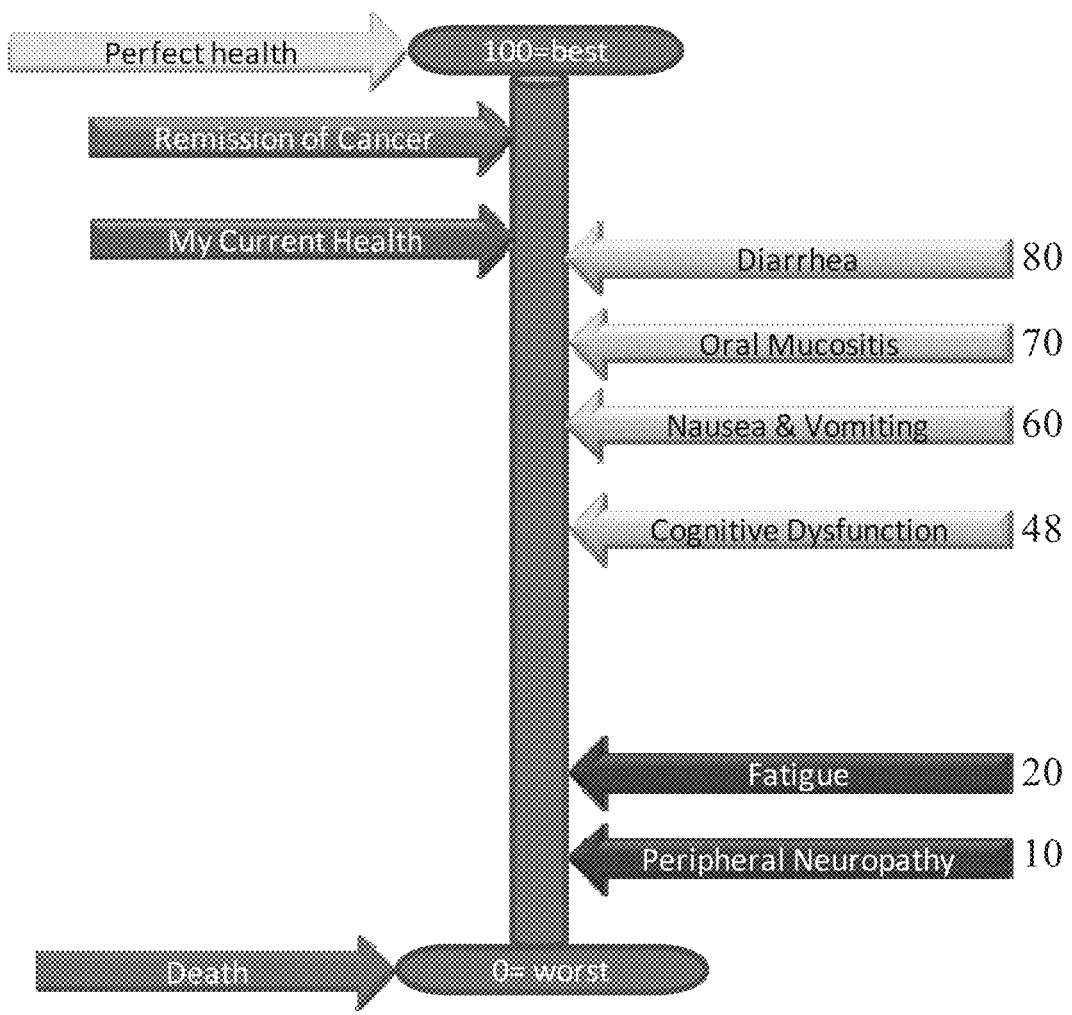
FIG. 4 depicts an example diagram for patient preference assessment.

FIG. 4 depicts an example diagram for patient preference assessment. As shown in FIG. 4, a visual analog scale is designed for quantifying the patient's willingness to tolerate side effects. For example, on the analog scale, a score of 100 is set for perfect health, and a score of 0 is set for death. Patient preferences with respect to different side effects can be quantified on the analog scale.

Specifically, as shown in FIG. 4, current health of the patient, for example, is ranked at 82 out of 100. Preference assessment shows that the patient is least willing to tolerate peripheral neuropathy (ranked at 10 out of 100) and fatigue (ranked at 20 out of 100).

A treatment regimen can be selected based on the combination of the personalized risk profile and the patient preference assessment. For example, for this particular patient with breast cancer, the second treatment option, dose-dense AC and weekly paclitaxel, may be selected as the preferred therapy. This allows a clinician to plan best supportive care, for example, including: palonosetron and dexamethasone prior to chemotherapy, two additional days of dexamethasone after chemotherapy for prevention of CINV, daily IV hydration and loperamide for prevention of diarrhea. In addition, the nursing staff may provide teaching to monitor the patient's temperature daily.

In some embodiments, chemotherapy regimens or agents may be switched to avoid side effects yet maintain the anti-cancer effect of a therapeutically equivalent regimen. Further, supportive care agents to prevent and/or ameliorate side effects may be planned accordingly.

In certain embodiments, the regimen-related outcome prediction system 104 is configured to implement one or more methods for assessing patient preferences. For example, several methods of assessing patient preferences in oncology treatment can be used: 1) standard gamble (SG), 2) time trade-off (TTO), 3) ranking or rating scale, and 4) visual analogue scale (VAS). In some embodiments, these methods are combined in different manners to effectively assess patient preferences.

The SG method is a quantitative assessment of patient preferences based on modern (or expected) utility theory, and is a method of decision-making under uncertainty that incorporates the decision maker's fundamental preferences in the decision process. Utility in this context refers to the desirability or preference of the individual for a given outcome expressed in a cardinal number; utility methods enable the decision-maker to reach a rational decision that is consistent with his/her personal preferences. Use of utility methods is based on health-related quality of life conditions (e.g., as described in Torrance et al., Journal of chronic diseases, 40.6, 1987). The SG technique may be implemented to measure utilities and used in clinical situations to help individual patients reach healthcare-related decisions (e.g., as described in Torrance et al., Journal of chronic diseases, 40.6, 1987). Because the individual's choices are made under uncertainty, this technique most closely resembles the uncertainty of the clinical situation and is considered to be the 'gold standard' of preference assessment tools.

In the SG method, patients choose either a gamble between perfect health (for a set time) and immediate death or a certainty of living in an intermediate health state (between perfect health and death) for a set time. Perfect health has a probability of P and death has a probability of 1−P. The value of P is varied until the patient is indifferent to the choice between the gamble and the certain intermediate health state, at which point P is the utility for the certain intermediate health state (e.g., as described in Blinman et al., Ann. Oncol., 23: 1104-1110, 2012). The treatment with highest expected utility may be the preferred treatment.

The TTO method was developed as an alternative for SG, specifically for use in healthcare settings (e.g., as described in Torrance et al., Journal of chronic diseases, 40.6, 1987). The TTO does not involve probabilities and is easier for patients to use. It involves trade-offs between two alternative health states, although patient decisions are made under conditions of certainty, which lessens its similarity to clinical realities. Patients choose either an intermediate health state for a given time (t) or perfect health for less than that given time (x<t) followed by immediate death. The duration (x) is modified until the patient is indifferent between the two alternatives.

The TTO technique has been validated against SG for assessment of health states 'preferred to death' and found to give similar results (as described in Torrance et al., Journal of chronic diseases, 40.6, 1987). The systems described herein may implement the TTO technique to determine preferences of treatment in breast, ovarian, colon, and lung cancers (e.g., as described in Sun et al., Oncology, 87: 118-128, 2002; Simes et al., Psycho-Oncology, 15: 1001-1013, 2001; Duric et al., Br. J. Cancer, 93(12): 1319-1323, 2005; Blinman et al., Eur. J. Cancer, 46(10): 1800-1807, 2010; Blinman et al., Lung Cancer, 72(2): 213-218, 2011).

The rating scale method is a quick and easy assessment tool in which patients are asked to rate a set of available options (i.e., chemotherapies; side effects) on a Likert scale or other scales, with the most preferred health state at one end and the least preferred at the other end. The rating scale method provides ordinal data about patient preferences (e.g., as described in Blinman et al., Ann Oncol., 23: 1104-1110, 2012). Rating scale results may require a power curve correction for optimal reliability (e.g., as described in Torrance et al., Journal of chronic diseases, 40.6, 1987).

The VAS method is simple for patients and caregivers to use, and patients may be asked to choose their health preference on a visual linear rating scale, with the scale anchored on a line by perfect health and death. The VAS ratings are made under conditions of certainty, have no trade-offs, and contain some measurement biases. The VAS may be better used in combination with other methods. The systems described herein may implement the VAS to determine patient preferences for cancer chemotherapy for ovarian cancer (e.g., as described in Sun et al., Oncology, 87: 118-128, 2002 and Sun et al., Support Care Cancer, 13: 219-227, 2005) and for cervical cancer (e.g., as described in Sun et al., Int. J. Gynecol. Cancer, 24(6): 1077-1084, 2014).

The choice of method(s) for assessing patient preferences depends on the clinical situation, goal of the assessment, and degree of acceptable patient burden, with some of the methods being more cognitively demanding than others. Multiple methods may be, and often are, combined to assess preferences most effectively. Determining patient preference is key in facilitating the most appropriate therapeutic decisions.

A number of clinical and demographic factors may influence a patient's preferences for cancer treatments. Incorporating the patient's perspective and value judgments into decisions about their treatment, for example, the trade-offs between the relative preference for improved survival and potential side effects, can help guide therapeutic regimens that are most effective and well-tolerated for the patient. Patient preferences may change depending on the situation. Whether a patient has already been treated or has already made a treatment decision can affect the outcomes of the assessment, so results should be considered in the context of the patient's situation (e.g., as described in Stiggelbout et al., J. Clin. Oncol., 19(1): 220-230, 2001).

In some embodiments, the systems and methods disclosed herein are configured to combine patient preference data, collected using well validated tools, with other patient results such as genomic analyses, in a shared medical decision model with the patient to obtain the most favorable treatment results.

Figure 5:
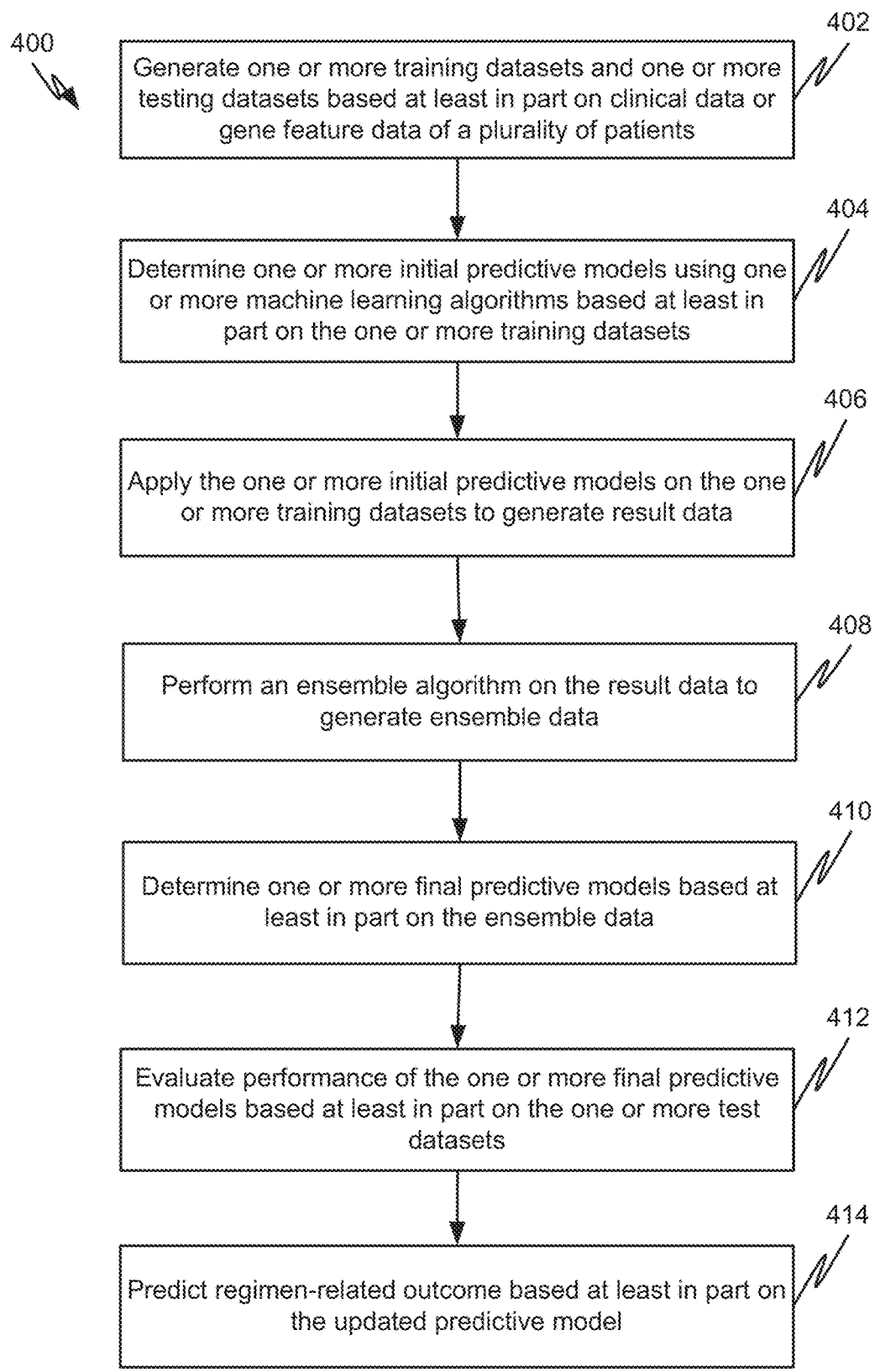
FIG. 5 depicts an example flow chart for building and evaluating predictive models.
Figure 6:
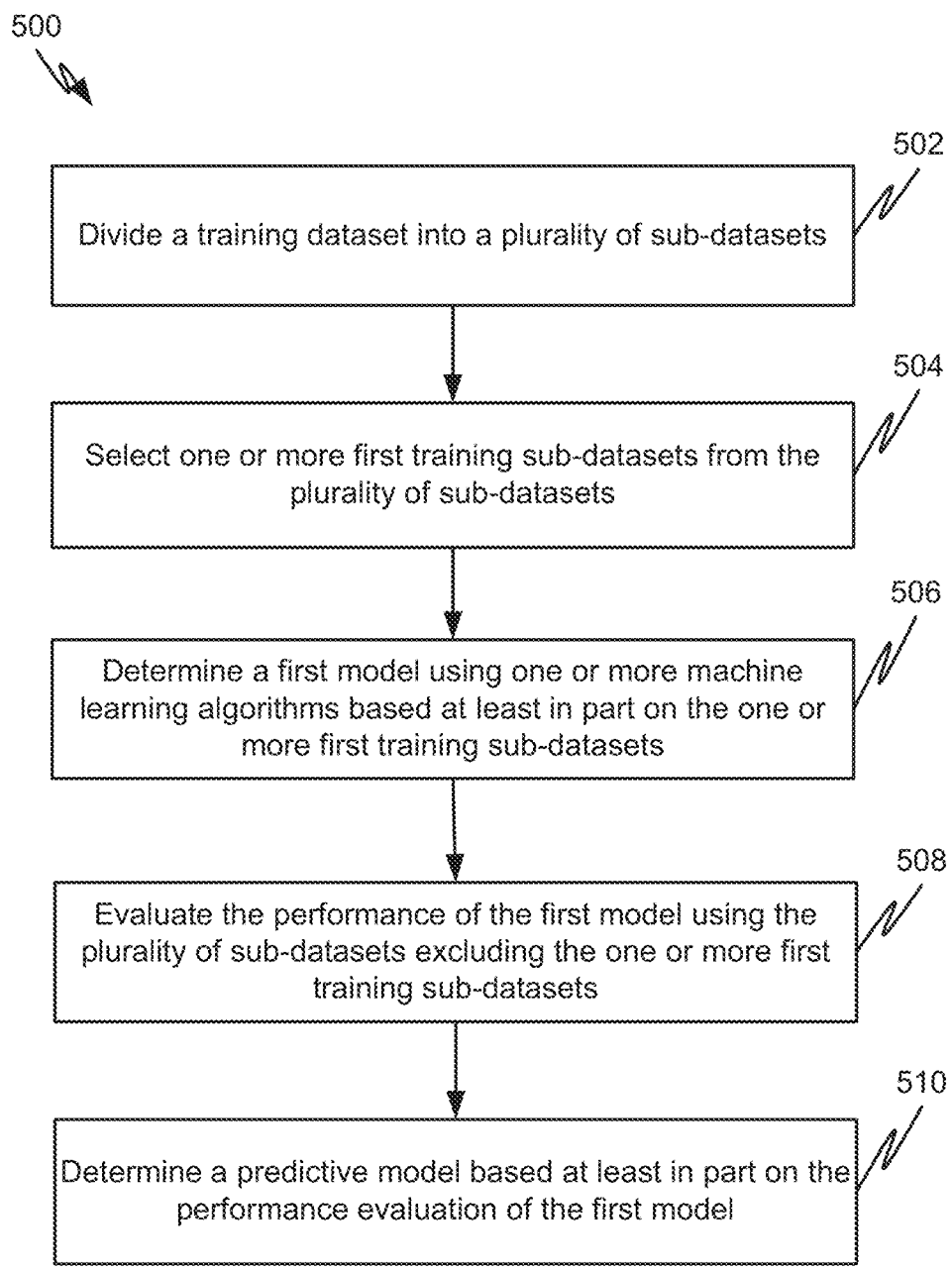
FIG. 6 depicts an example flow chart for model building.

FIG. 5 depicts an example flow chart for building and evaluating predictive models. As shown in FIG. 5, at 402, one or more training datasets and one or more testing datasets are generated based at least in part on clinical data or gene feature data of a plurality of patients. For example, the clinical data includes diagnosis data, cancer-stage data, regimen related data, and neuropathy related data related to individual patients. The gene feature data may include one or more predetermined SNPs and/or one or more filtered SNPs which are generated through certain pre-processing steps and a filtering process. At 404, one or more initial predictive models are determined using one or more machine learning algorithms based at least in part on the one or more training datasets (e.g., as shown in FIG. 6). For example, the one or more machine learning algorithms correspond to one or more of the following: penalized logistic regression, random forests, and C5.0.

At 406, the one or more initial predictive models are applied on the one or more training datasets to generate result data. For example, the training datasets include a clinical predictor dataset, a selected SNP dataset, and a filtered SNP dataset. At 408, an ensemble algorithm is performed on the result data to generate ensemble data. For example, the ensemble algorithm corresponds to an average calculation or a logistic regression model. The ensemble algorithm may be applied to a combination of clinical predictor result data and selected SNP result data, or a combination of the clinical predictor result data, the selected SNP result data, and filtered SNP result data. At 410, one or more final predictive models are determined based at least in part on the ensemble data. At 412, performance of the one or more final predictive models is evaluated based at least in part on the one or more test datasets. At 414, regimen-related outcomes are predicted using the one or more final predictive models.

FIG. 6 depicts an example flow chart for model building. As shown in FIG. 6, at 502, a training dataset is divided into a plurality of sub-datasets. At 504, one or more first training sub-datasets are selected from the plurality of sub-datasets. At 506, a first model is determined using one or more machine learning algorithms based at least in part on the one or more first training sub-datasets. At 508, the performance of the first model is evaluated using the plurality of sub-datasets excluding the one or more first training sub-datasets. Such a process is repeated multiple times, and each time a different group of sub-datasets are selected from the training dataset for model building and evaluation. At 510, a predictive model is determined based at least in part on the performance evaluation of the first model and other models generated through the different iterations based on different groups of sub-datasets selected from the training dataset.

Figure 7:
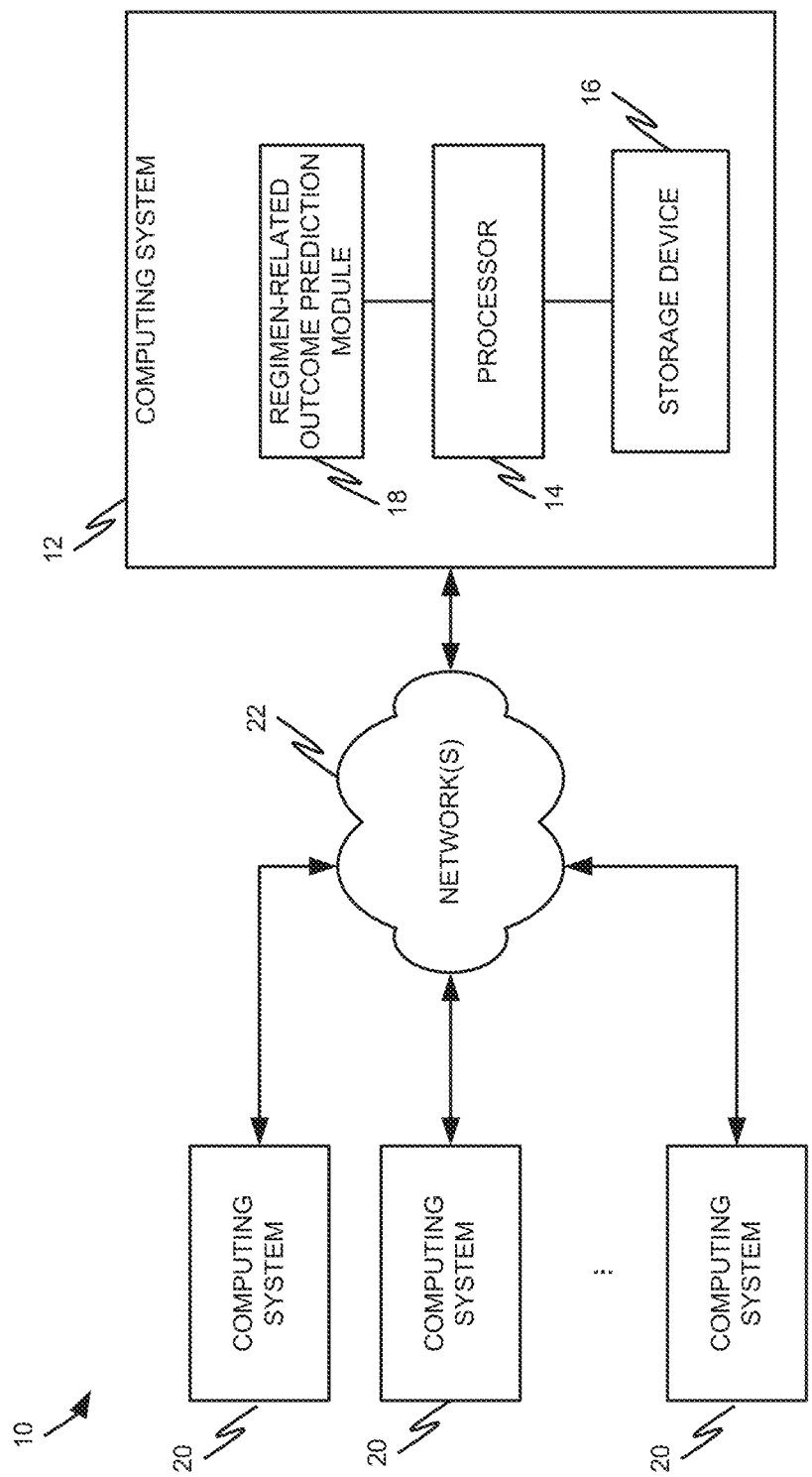
FIG. 7 depicts an example diagram showing a system for predicting regimen-related outcomes.

FIG. 7 depicts an example diagram showing a system for predicting regimen-related outcomes. As shown in FIG. 7, the system 10 includes a computing system 12 that contains a processor 14, a storage device 16 and a regimen-related outcome prediction module 18. The computing system 12 includes any suitable type of computing device (e.g., a server, a desktop, a laptop, a tablet, a mobile phone, etc.) that includes the processor 14 or provide access to a processor via a network or as part of a cloud-based application. The regimen-related outcome prediction module 18 includes tasks (e.g., corresponding to steps shown in FIG. 4) and is implemented as part of a user interface module (not shown in FIG. 7).

Figure 8:
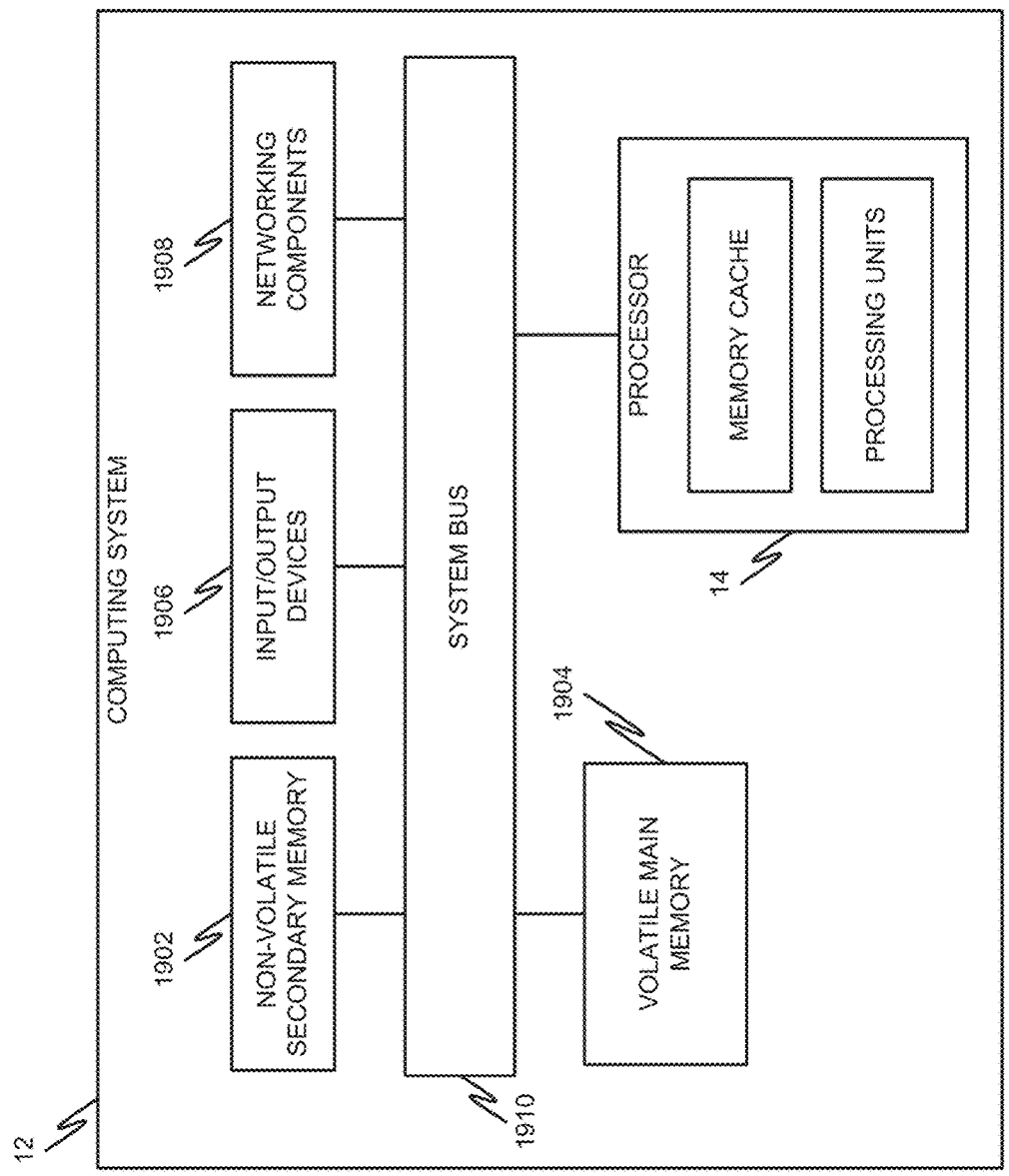
FIG. 8 depicts an example diagram showing a computing system for predicting regimen-related outcomes.

FIG. 8 depicts an example diagram showing a computing system for predicting regimen-related outcomes. As shown in FIG. 8, the computing system 12 includes a processor 14, memory devices 1902 and 1904, one or more input/output devices 1906, one or more networking components 1908, and a system bus 1910. In some embodiments, the computing system 12 includes the regimen-related outcome prediction module 18, and provides access to the regimen-related outcome prediction module 18 to a user as a stand-alone computer.

6. Exemplary Embodiment

This embodiment is merely an example, which should not unduly limit the scope of the claims. One of ordinary skill in the art would recognize many variations, alternatives, and modifications. For example, an endpoint for evaluation in this embodiment is binary severity classification of chemotherapy induced peripheral neuropathy (CIPN). The objectives for the endpoint are to:
1. Build and evaluate predictive models based on a biased predictor selection approach; and
2. Build and evaluate predictive models based on an unbiased predictor selection approach.

It should be understood that the systems and methods described herein can be configured to adopt other endpoints and related objectives for model building/evaluation and outcome prediction.

As an example, predictive models are built and evaluated based on an unbiased predictor selection approach for the endpoint (CIPN) and contains the following processes: data handling, descriptive analyses, and predictive modeling of classification outcomes.

6.1 Data Handling

A clinical dataset is created through one or more of the following steps:
1. importing patient level covariates and the CIPN endpoint;
2. splitting a diagnosis factor into individual binary predictors for modeling (e.g. breast=1 for breast cancer, 0 otherwise, etc.);
3. splitting a stage factor into individual binary predictors for modeling (e.g. stage1=1 for stage 1 patients, 0 otherwise, etc.);
4. splitting a regimen factor into individual binary predictors for modeling (e.g. CIPNreg1=1 if CIPNreg n=1, 0 otherwise, etc.);
5. keeping subjects with quality values of 0 (e.g., data of decent quality with no major problems) or 1 (high neuropathy scores immediately prior to the first cycle of treatment);
6. using CIPN score data (e.g., maximum neuropathy score during the first 9 cycles) as the endpoint and categorizing the data into unaffected (e.g., <4) or affected (e.g., ≥4). If CIPN score data is missing, then it is imputed only if the patient exceeded the criterion in the previous time period; and
7. splitting data into a training set (75%) and test set (25%) using a stratified random approach using a numeric regimen categorization and response category in order to ensure that regimens for affected subjects are proportionally represented in training and testing sets.

The original SNP data contains approximately 2.3 million unique SNPs. The following pre-processing steps and the data filtering process are taken prior to predictive modeling:
1. The following ACORNNO are removed due to too much missing data across SNPs: 38, 102, 211, and 320.
2. Highly associated SNPs (contingency table agreement≥0.7) are removed. If a pair of SNPs have high association, then the first SNP is kept and the second is removed. The number of SNPs after this process is approximately 620 K.
3. Less than 0.1% of the data is missing (e.g., labeled as "U"). Because the percentage of missing values is very small, the values are imputed to label "H" in order to prevent computational errors in the model training process.
4. Using only the subjects in the training data, recursive partitioning models using 10-fold cross-validation are trained. Any SNP that is used in any of the recursive partitioning models is kept. This process identifies approximately 4300 SNPs as relevant to the response.

The resulting SNPs are referred to as "Filtered SNPs" in the predictive modeling below (e.g., Section 6.3). The training set has 152 samples and the test set has 48 samples. The distribution of affected/unaffected subjects by training/test set is presented in Table 1.

TABLE 1

|  | Affected | Unaffected |
| --- | --- | --- |
| Test | 35 | 13 |
| Training | 110 | 42 |

6.2 Descriptive Analysis

Figure 9:
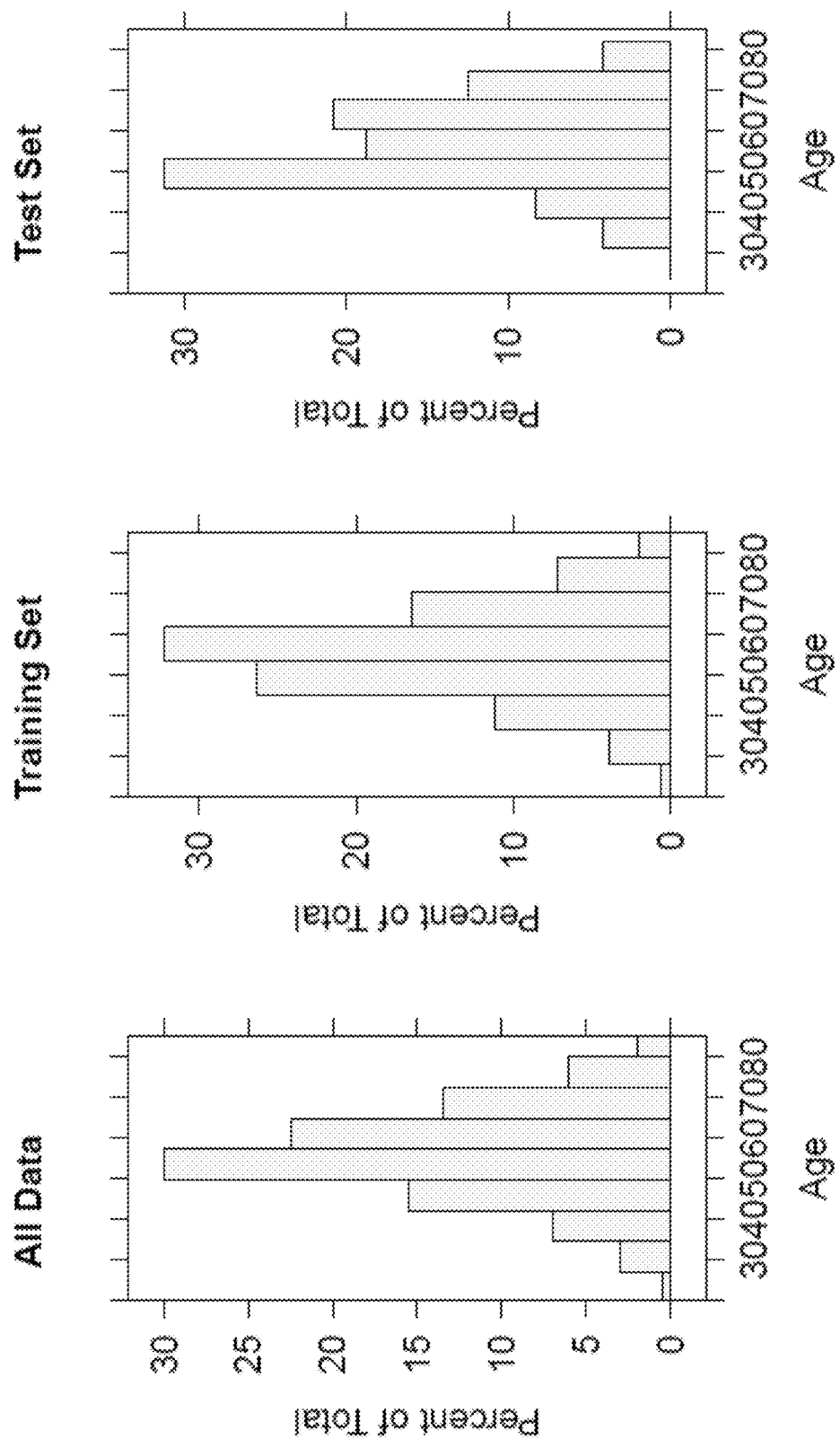
FIG. 9-FIG. 48 depict example diagrams showing model building and evaluation in one embodiment.

FIG. 9 depicts an example diagram showing the distribution of age for the entire data set, and within the training and test splits. The average age for all data and within the training and test sets is 56, 55.8, and 56.6, respectively. Overall, the distribution of age is similar across the sets, indicating no bias in age in the selection process between training and test sets.

Tables 2 and 3 provide the counts and percents for the remaining demographic variables and regimens for all data and within the training and test sets. The denominators for computing the percents in these tables are 200 (All), 152 (Train), and 48 (Test). Similar to age, the percent of patients in the training and test sets are similar across the demographic variables and regimens indicating no bias in the randomization process. Table 4 provides the counts and percents of subjects who were affected within each regimen for all data and within the training and test sets. The denominators for computing the percents in these tables are 200 (All), 152 (Train), and 48 (Test).

TABLE 2

|  | All (n) | All (%) | Training (n) | Training (%) | Test (n) | Test (%) |
|---|---|---|---|---|---|---|
| male | 40 | 20.0 | 30 | 19.7 | 10 | 20.8 |
| diabetes | 36 | 18.0 | 28 | 18.4 | 8 | 16.7 |
| breast | 95 | 47.5 | 73 | 48.0 | 22 | 45.8 |
| colorectal | 58 | 29.0 | 45 | 29.6 | 13 | 27.1 |
| nsclc | 16 | 8.0 | 11 | 7.2 | 5 | 10.4 |
| ovarian | 26 | 13.0 | 20 | 13.2 | 6 | 12.5 |
| prostate | 5 | 2.5 | 3 | 2.0 | 2 | 4.2 |
| Stage1 | 33 | 16.5 | 24 | 15.8 | 9 | 18.8 |
| Stage2 | 61 | 30.5 | 49 | 32.2 | 12 | 25.0 |
| Stage3 | 60 | 30.0 | 48 | 31.6 | 12 | 25.0 |
| Stage4 | 40 | 20.0 | 26 | 17.1 | 14 | 29.2 |
| Stage5 | 6 | 3.0 | 5 | 3.3 | 1 | 2.1 |

TABLE 3

| Regimen | All (n) | All (%) | Training (n) | Training (%) | Test (n) | Test (%) |
|---|---|---|---|---|---|---|
| Alimta +/− Avastin | 1 | 0.5 | 1 | 0.7 | 0 | 0.0 |
| Carbo/Alimta +/− Avastin | 3 | 1.5 | 2 | 1.3 | 1 | 2.1 |
| Carbo/Docetaxel +/− Herceptin | 12 | 6.0 | 10 | 6.6 | 2 | 4.2 |
| Carbo/Gem | 1 | 0.5 | 1 | 0.7 | 0 | 0.0 |
| Carbo/Taxol +/− Biologic | 30 | 15.0 | 22 | 14.5 | 8 | 16.7 |
| Cisplt + Alimta | 2 | 1.0 | 2 | 1.3 | 0 | 0.0 |
| Docetaxel + Cytoxan +/− Herceptin | 16 | 8.0 | 12 | 7.0 | 4 | 8.3 |
| Docetaxel + Pred q21 | 5 | 2.5 | 3 | 2.0 | 2 | 4.2 |
| Dose Dense AC + Taxol | 68 | 34.0 | 51 | 33.6 | 17 | 35.4 |
| FOLFIRI +/− Avastin | 4 | 2.0 | 4 | 2.6 | 0 | 0.0 |
| FOLFOX4 +/− Avastin | 1 | 0.5 | 1 | 0.7 | 0 | 0.0 |
| FOLFOX6 | 12 | 6.0 | 10 | 6.6 | 2 | 4.2 |
| MFOLFOX6 +/− Avastin | 41 | 20.5 | 30 | 19.7 | 11 | 22.9 |
| TC/Tykerb | 1 | 0.5 | 1 | 0.7 | 0 | 0.0 |
| TCH +/− Tykerb | 1 | 0.5 | 1 | 0.7 | 0 | 0.0 |
| Wkly Taxol/Carbo +/− Avastin | 2 | 1.0 | 1 | 0.7 | 1 | 2.1 |

TABLE 4

| Regimen | All (n) | All (%) | Training (n) | Training (%) | Test (n) | Test (%) |
|---|---|---|---|---|---|---|
| Alimta +/− Avastin | 1 | 0.5 | 1 | 0.7 | 0 | 0.0 |
| Carbo/Docetaxel +/− Herceptin | 10 | 5.0 | 8 | 5.3 | 2 | 4.2 |
| Carbo/Gem | 1 | 0.5 | 1 | 0.7 | 0 | 0.0 |
| Carbo/Taxol +/− Biologic | 23 | 11.5 | 18 | 11.8 | 5 | 10.4 |
| Cisplt + Alimta | 2 | 1.0 | 2 | 1.3 | 0 | 0.0 |
| Docetaxel + Cytoxan +/− Herceptin | 15 | 7.5 | 11 | 7.2 | 4 | 8.3 |
| Docetaxel + Pred q21 | 1 | 0.5 | 1 | 0.7 | 0 | 0.0 |
| Dose Dense AC + Taxol | 49 | 24.5 | 36 | 23.7 | 13 | 27.1 |
| FOLFIRI +/− Avastin | 2 | 1.0 | 2 | 1.3 | 0 | 0.0 |
| FOLFOX4 +/− Avastin | 1 | 0.5 | 1 | 0.7 | 0 | 0.0 |
| FOLFOX6 | 11 | 5.5 | 9 | 5.9 | 2 | 4.2 |
| MFOLFOX6 +/− Avastin | 27 | 13.5 | 19 | 12.5 | 8 | 16.7 |
| TC/Tykerb | 1 | 0.5 | 1 | 0.7 | 0 | 0.0 |
| Wkly Taxol/Carbo +/− Avastin | 1 | 0.5 | 0 | 0.0 | 1 | 2.1 |

6.3 Predictive Modeling of Classification Outcomes

The predictive ability for three distinct predictors sets is investigated:
1. Clinical predictors
2. Selected SNPs
3. Filtered SNPs For example, the selected SNPs are determined as SNPs identified in three manuscripts (i.e., Jean E. Abraham et al., Clinical Cancer Research 20(9), May 1, 2014; McWhinney-Glass et al., Clinical Cancer Research 19(20), Oct. 15, 2013; Won et al., Cancer, 118:2828-36, 2012) as being related to the endpoint of interest. In total, 24 SNPs were identified in these manuscripts. 14 of these 24 SNPs are used for the analysis herein. Many predictive models are explored for this analysis. In the process of building models, imbalance in the response influences models that place samples into the majority class. To adjust for imbalance, both up-sampling (selecting additional minority class subjects with replacement to increase the minority class size) and down-sampling (sampling the majority class to create balance with the minority class) are explored. In the data of this embodiment, down-sampling yielded better models than up-sampling. This is likely due to the small training set size.

For all models, 5 repeats of 10-fold cross-validation are used on the training set to determine the optimal tuning parameter setting. For the down-sampled data, many models are explored. The three models to be described in detail herein are penalized logistic regression, random forests (RF), and C5.0. A brief explanation of each method has been provided in Section 5.

The results from each of these models are obtained for the following subsets of data: clinical predictors, selected SNPs, and filtered SNPs. To give equal weight to each of these predictor subsets, a simple ensemble and a model-based ensemble are constructed for the following combinations: clinical predictors and selected SNPs; and clinical predictors, selected SNPs, and filtered SNPs. The simple ensemble approach takes the average of the model predictions, while the model-based approach uses a logistic regression model to combine the predictions across models.

The three modeling techniques have similar predictive performance, but C5.0 is computationally more efficient, in some circumstances. For example, C5.0 performs better than the other two models on the selected SNP subset, while RF performs slightly better than the other two models on the filtered SNP subset. The penalized logistic regression model performs better than the other two models on the model-based ensemble across the clinical, selected SNPs, and filtered SNPs predictors.

6.3.1 C5.0
6.3.1.1 Clinical Predictors

Figure 10:
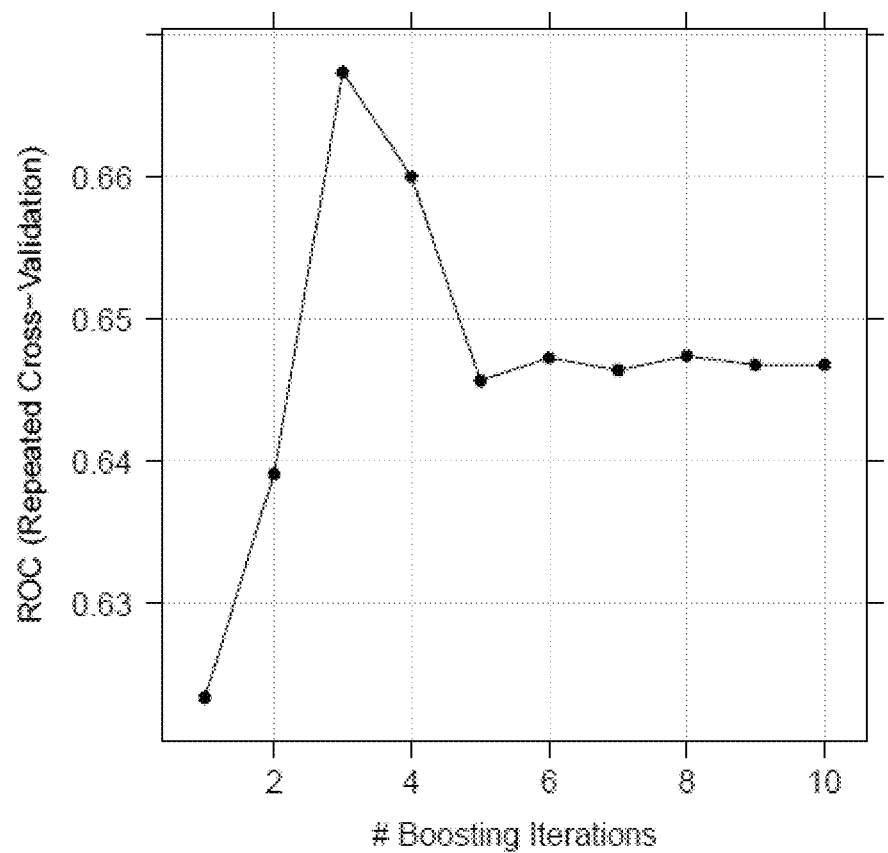
Figure 11:
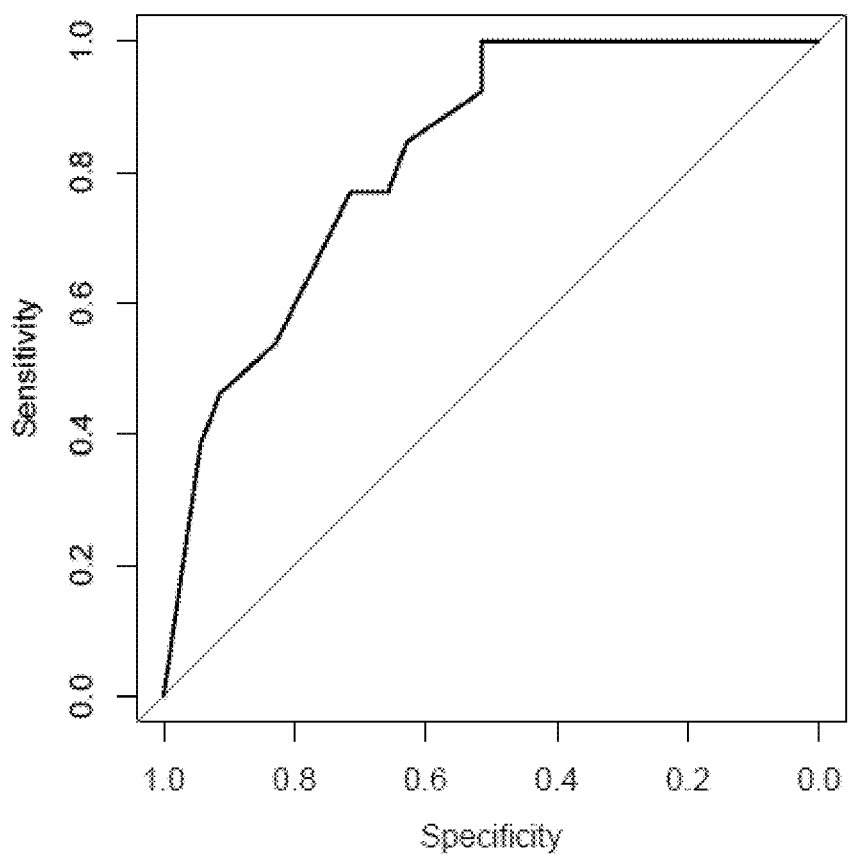
Figure 12:
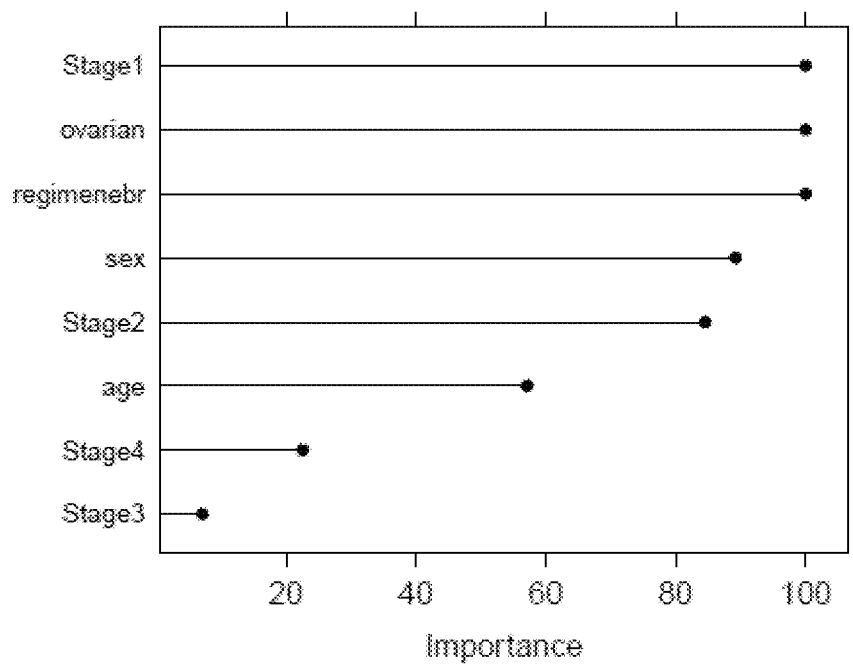

FIG. 10 depicts an example diagram showing the tuning parameter profile for the C5.0 model related to clinical predictors. The optimal number of trials (iterations) for this data is 3. The distribution of affected/unaffected subjects based on the clinical predictors is presented in Table 5, where Y-axis indicates predicted affected/unaffected subjects and X-axis indicates observed affected/unaffected subjects. FIG. 11 depicts an example diagram showing a receiver-operating-characteristic (ROC) curve related to the clinical predictors. FIG. 12 depicts an example diagram showing top important predictors among the clinical predictors.

TABLE 5

|  | Affected | Unaffected |
|---|---|---|
| Affected | 22 | 2 |
| Unaffected | 13 | 11 |

6.3.1.2 Selected SNPs

Figure 13:
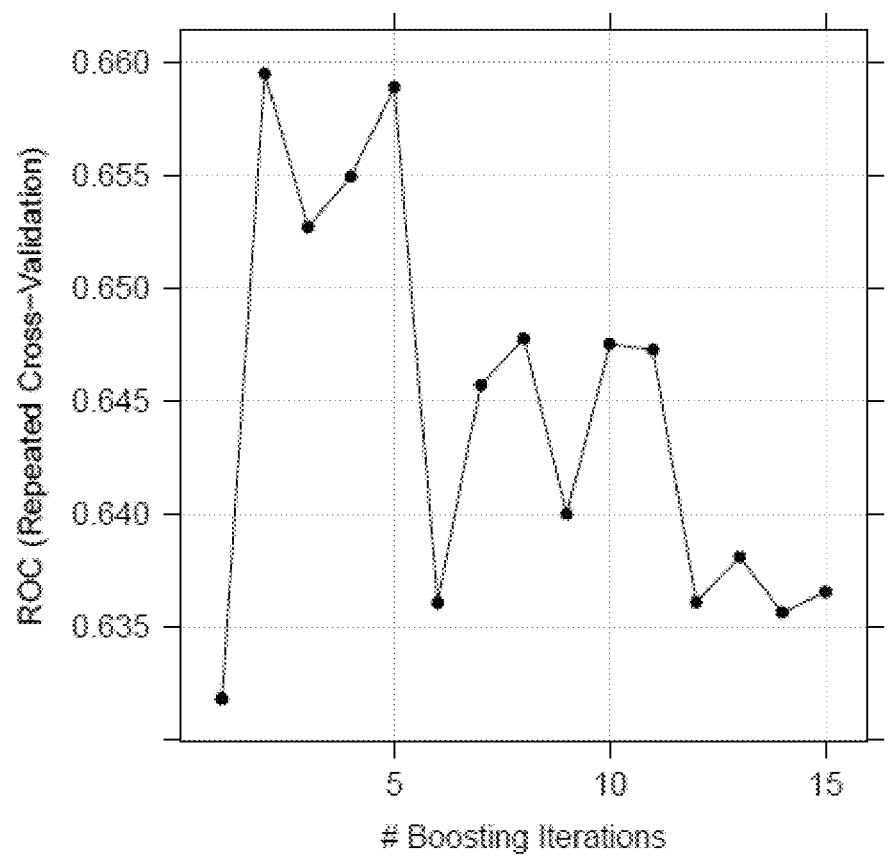
Figure 14:
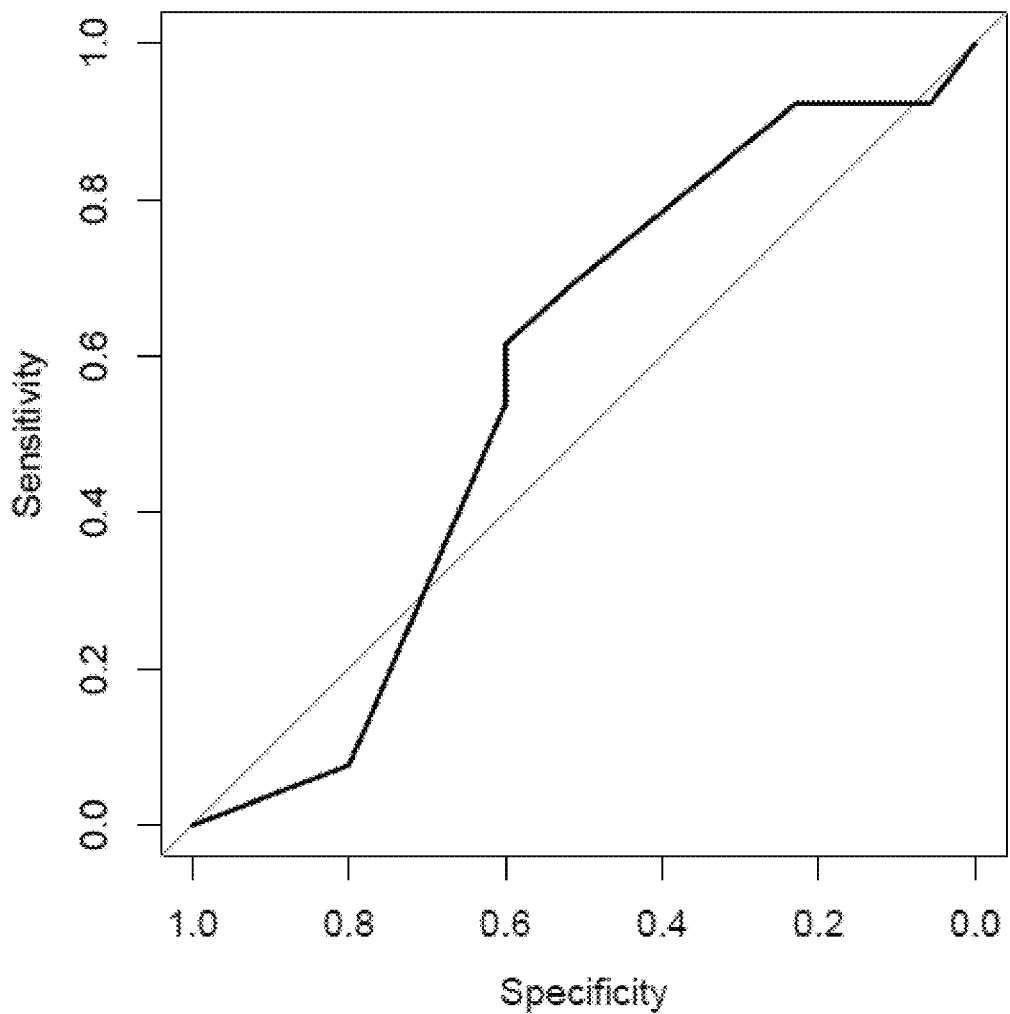
Figure 15:
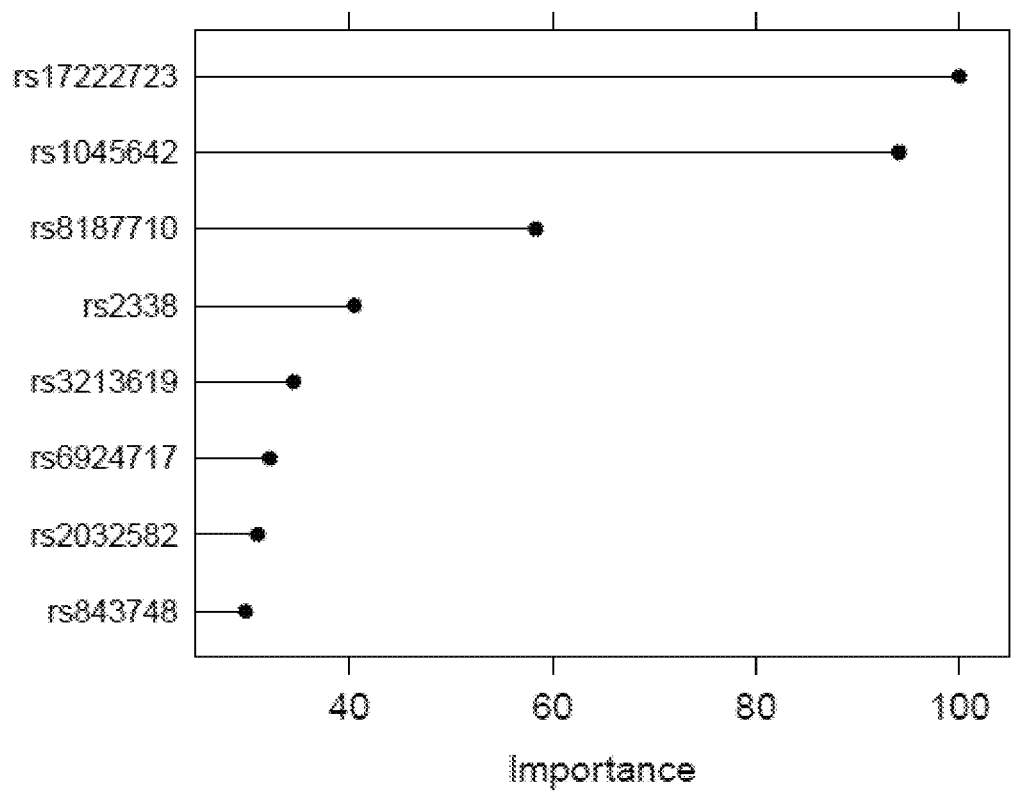

FIG. 13 depicts an example diagram showing the tuning parameter profile for the C5.0 model related to the selected SNPs. The optimal number of trials (iterations) for this data is 2. The distribution of affected/unaffected subjects based on the selected SNPs is presented in Table 6, where Y-axis indicates predicted affected/unaffected subjects and X-axis indicates observed affected/unaffected subjects. FIG. 14 depicts an example diagram showing a ROC curve related to the selected SNPs. FIG. 15 depicts an example diagram showing the top important predictors among the selected SNPs.

TABLE 6

|  | Affected | Unaffected |
|---|---|---|
| Affected | 21 | 6 |
| Unaffected | 14 | 7 |

Figure 16:
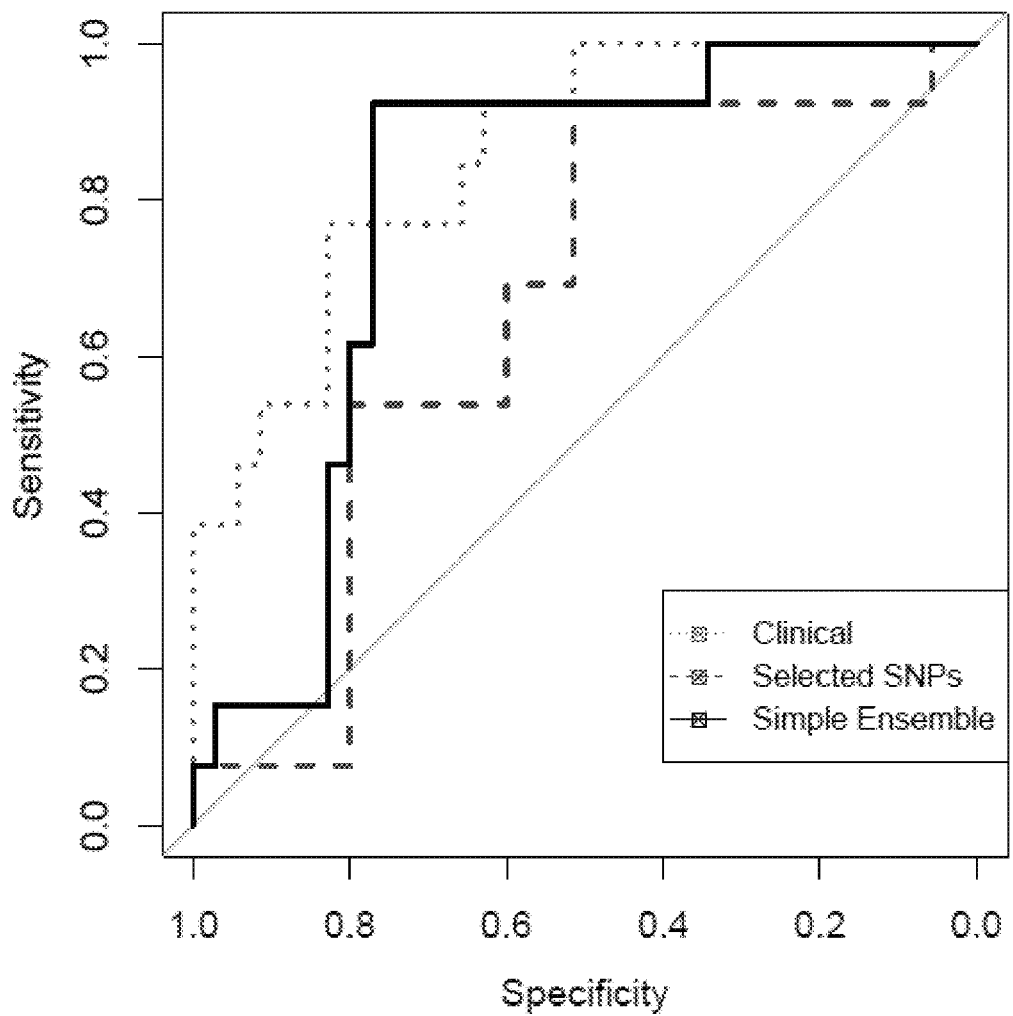

6.3.1.3 Simple Ensemble Approach: Clinical Predictions and Selected SNPs Predictions A simple ensemble approach is applied to determine a simple average of test set predicted probabilities to classify subjects into the affected and unaffected categories. FIG. 16 depicts an example diagram showing a ROC curve based on the average of clinical predictions and selected SNPs predictions. The distribution of affected/unaffected subjects based on the simple ensemble approach is presented in Table 7, where Y-axis indicates predicted affected/unaffected subjects and X-axis indicates observed affected/unaffected subjects. Table 8 includes prediction data of the simple ensemble approach from calculation based on an average of the model probabilities.

TABLE 7

|  | Affected | Unaffected |
|---|---|---|
| Affected | 27 | 3 |
| Unaffected | 8 | 10 |

TABLE 8

| Observed | Clinical | Selected | Ensemble | Ensemble Pred |
|---|---|---|---|---|
| Affected | 0.32 | 0.27 | 0.29 | Unaffected |
| Affected | 1.00 | 0.12 | 0.56 | Affected |
| Affected | 1.00 | 0.75 | 0.88 | Affected |
| Affected | 0.33 | 0.70 | 0.56 | Affected |
| Affected | 0.33 | 0.12 | 0.23 | Unaffected |
| Affected | 1.00 | 0.27 | 0.64 | Affected |
| Affected | 0.00 | 0.70 | 0.40 | Unaffected |
| Affected | 0.32 | 0.12 | 0.22 | Unaffected |
| Unaffected | 0.00 | 0.70 | 0.35 | Unaffected |
| Unaffected | 0.00 | 0.75 | 0.38 | Unaffected |
| Affected | 0.40 | 0.27 | 0.33 | Unaffected |
| Unaffected | 0.00 | 0.90 | 0.45 | Unaffected |
| Affected | 0.71 | 0.78 | 0.75 | Affected |
| Unaffected | 0.32 | 0.78 | 0.55 | Affected |
| Unaffected | 0.40 | 0.27 | 0.33 | Unaffected |
| Affected | 0.66 | 0.79 | 0.73 | Affected |
| Affected | 0.71 | 0.79 | 0.75 | Affected |
| Affected | 0.40 | 0.12 | 0.26 | Unaffected |
| Unaffected | 0.29 | 0.78 | 0.54 | Affected |
| Affected | 1.00 | 0.12 | 0.56 | Affected |
| Affected | 0.66 | 0.78 | 0.72 | Affected |
| Affected | 1.00 | 0.75 | 0.88 | Affected |
| Affected | 0.22 | 0.78 | 0.56 | Affected |
| Affected | 1.00 | 0.78 | 0.80 | Affected |
| Unaffected | 0.33 | 0.27 | 0.30 | Unaffected |
| Affected | 0.32 | 0.78 | 0.55 | Affected |
| Unaffected | 0.33 | 0.27 | 0.30 | Unaffected |
| Affected | 0.70 | 0.78 | 0.74 | Affected |
| Affected | 0.66 | 0.78 | 0.72 | Affected |
| Affected | 0.70 | 0.78 | 0.74 | Affected |
| Affected | 1.00 | 0.70 | 0.90 | Affected |
| Affected | 1.00 | 0.27 | 0.64 | Affected |
| Affected | 1.00 | 0.27 | 0.64 | Affected |

TABLE 8-continued

| Observed | Clinical | Selected | Ensemble | Ensemble Pred |
|---|---|---|---|---|
| Unaffected | 0.00 | 0.27 | 0.14 | Unaffected |
| Affected | 1.00 | 0.70 | 0.90 | Affected |
| Affected | 0.66 | 0.00 | 0.78 | Affected |
| Affected | 1.00 | 0.78 | 0.89 | Affected |
| Affected | 0.33 | 0.78 | 0.56 | Affected |
| Affected | 1.00 | 0.12 | 0.56 | Affected |
| Unaffected | 0.66 | 0.27 | 0.47 | Unaffected |
| Unaffected | 0.69 | 0.78 | 0.74 | Affected |
| Unaffected | 0.00 | 0.12 | 0.06 | Unaffected |
| Unaffected | 0.33 | 0.27 | 0.30 | Unaffected |
| Affected | 0.29 | 0.27 | 0.28 | Unaffected |
| Affected | 0.00 | 0.12 | 0.06 | Unaffected |
| Affected | 1.00 | 0.75 | 0.88 | Affected |
| Affected | 1.00 | 0.27 | 0.64 | Affected |
| Affected | 0.36 | 0.90 | 0.03 | Affected |

Figure 17:
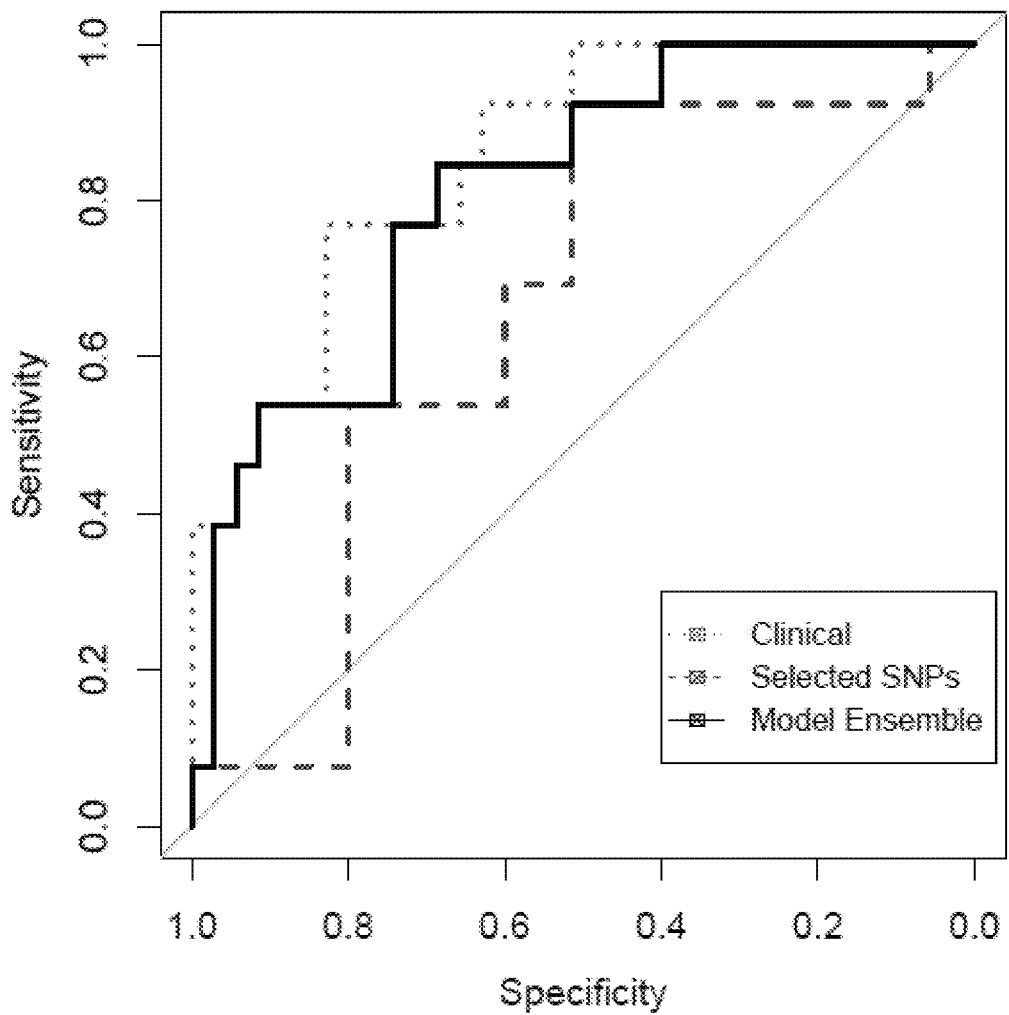

6.3.1.4 Model-Based Ensemble Approach: Clinical Predictions and Selected SNPs Predictions A logistic regression model is built on the hold-out datasets in the previous training step using the optimal tuning parameters. The logistic regression model is then applied to the test set. The distribution of affected/unaffected subjects based on a cross-validated model using the clinical predictions and selected SNPs predictions is presented in Table 9, where Y-axis indicates predicted affected/unaffected subjects and X-axis indicates observed affected/unaffected subjects. FIG. 17 depicts an example diagram showing a ROC curve based on clinical predictions and selected SNPs predictions using a model. Table 10 includes prediction data of the mode-based ensemble approach from calculation based on a model of the model probabilities.

TABLE 9

|  | Affected | Unaffected |
|---|---|---|
| Affected | 12 | 11 |
| Unaffected | 23 | 2 |

TABLE 10

| Observed | Clinical | Selected | Model | Model Pred |
|---|---|---|---|---|
| Affected | 0.32 | 0.27 | 0.52 | Affected |
| Affected | 1.00 | 0.12 | 0.40 | Unaffected |
| Affected | 1.00 | 0.75 | 0.43 | Unaffected |
| Affected | 0.33 | 0.79 | 0.54 | Affected |
| Affected | 0.33 | 0.12 | 0.50 | Affected |
| Affected | 1.00 | 0.27 | 0.41 | Unaffected |
| Affected | 0.00 | 0.79 | 0.60 | Affected |
| Affected | 0.32 | 0.12 | 0.51 | Affected |
| Unaffected | 0.00 | 0.70 | 0.59 | Affected |
| Unaffected | 0.00 | 0.75 | 0.59 | Affected |
| Affected | 0.40 | 0.27 | 0.50 | Affected |
| Unaffected | 0.00 | 0.00 | 0.60 | Affected |
| Affected | 0.71 | 0.78 | 0.48 | Unaffected |
| Unaffected | 0.32 | 0.78 | 0.55 | Affected |
| Unaffected | 0.40 | 0.27 | 0.50 | Affected |
| Affected | 0.66 | 0.79 | 0.49 | Unaffected |
| Affected | 0.71 | 0.79 | 0.48 | Unaffected |
| Affected | 0.39 | 0.12 | 0.49 | Unaffected |
| Unaffected | 0.29 | 0.78 | 0.55 | Affected |
| Affected | 1.00 | 0.12 | 0.40 | Unaffected |
| Affected | 0.66 | 0.78 | 0.49 | Unaffected |
| Affected | 1.00 | 0.75 | 0.42 | Unaffected |
| Affected | 0.33 | 0.78 | 0.54 | Affected |
| Affected | 1.00 | 0.78 | 0.44 | Unaffected |
| Unaffected | 0.33 | 0.27 | 0.51 | Affected |
| Affected | 0.32 | 0.78 | 0.55 | Affected |

TABLE 10-continued

| Observed | Clinical | Selected | Model | Model Pred |
|---|---|---|---|---|
| Unaffected | 0.33 | 0.27 | 0.51 | Affected |
| Affected | 0.70 | 0.78 | 0.48 | Unaffected |
| Affected | 0.66 | 0.78 | 0.49 | Unaffected |
| Affected | 0.70 | 0.78 | 0.48 | Unaffected |
| Affected | 1.00 | 0.79 | 0.44 | Unaffected |
| Affected | 1.00 | 0.27 | 0.41 | Unaffected |
| Affected | 1.00 | 0.27 | 0.41 | Unaffected |
| Unaffected | 0.00 | 0.27 | 0.57 | Affected |
| Affected | 1.00 | 0.79 | 0.44 | Unaffected |
| Affected | 0.66 | 0.90 | 0.50 | Unaffected |
| Affected | 1.00 | 0.78 | 0.44 | Unaffected |
| Affected | 0.33 | 0.78 | 0.54 | Affected |
| Affected | 1.00 | 0.12 | 0.40 | Unaffected |
| Unaffected | 0.66 | 0.27 | 0.46 | Unaffected |
| Unaffected | 0.69 | 0.78 | 0.49 | Unaffected |
| Unaffected | 0.00 | 0.12 | 0.56 | Affected |
| Unaffected | 0.33 | 0.27 | 0.51 | Affected |
| Affected | 0.29 | 0.27 | 0.52 | Affected |
| Affected | 0.00 | 0.12 | 0.56 | Affected |
| Affected | 1.00 | 0.75 | 0.43 | Unaffected |
| Affected | 1.00 | 0.27 | 0.41 | Unaffected |
| Affected | 0.36 | 0.00 | 0.55 | Affected |

6.3.1.5 Filtered SNPs

As described in Section 6.1, SNPs are identified as potentially important using a cross-validated recursive partitioning approach. In total, 4368 SNPs are identified in this process. The top 200 SNPs based on variable importance ranking are presented in Table 11.

TABLE 11

| C1 | C2 | C3 | C4 | C5 |
|---|---|---|---|---|
| rs1000701 | rs9530263 | rs6973851 | kgp11276660 | kgp4822821 |
| rs10250195 | rs978854 | rs7152412 | kgp11249675 | kgp5013508 |
| rs10491984 | kgp12147164 | rs7204751 | kgp1152452 | kgp5154577 |
| rs10511271 | kgp6857690 | rs741339 | kgp11590177 | kgp5322406 |
| rs10853124 | rs12186512 | rs7639756 | kgp1171450 | kgp5666989 |
| rs10963188 | rs2131210 | rs7895805 | kgp11880615 | kgp5781005 |
| rs11157216 | rs6619 | rs7973103 | kgp12025888 | kgp5894054 |
| rs11257804 | rs7382146 | rs834767 | kgp12150323 | kgp6053642 |
| rs11898628 | rs10150423 | rs9333240 | kgp12187497 | kgp618023 |
| rs12185748 | rs10193760 | rs9530262 | kgp1232554 | kgp6253679 |
| rs1244791 | rs10489829 | rs9599040 | kgp12475652 | kgp6525677 |
| rs12645173 | rs10836174 | rs9938218 | kgp1296418 | kgp6704767 |
| rs13077887 | rs10904696 | rs13164140 | kgp1570784 | kgp6793080 |
| rs1284681 | rs1107773 | rs1982002 | kgp16905 | kgp6846921 |
| rs1464205 | rs1158602 | rs6437137 | kgp176973 | kgp7014989 |
| rs1478926 | rs11689427 | rs7204283 | kgp1849314 | kgp7125852 |
| rs1567083 | rs12443665 | rs4858533 | kgp19569551 | kgp7250912 |
| rs1707113 | rs12718026 | kgp4494086 | kgp2122064 | kgp7342509 |
| rs1719480 | rs1322231 | kgp1124966 | kgp2248463 | kgp7455196 |
| rs1815811 | rs141748 | kgp10379506 | kgp22760805 | kgp7596010 |
| rs2014450 | rs1551858 | kgp1776634 | kgp2292414 | kgp7689305 |
| rs2159766 | rs1695770 | kgp2206685 | kgp2411366 | kgp7795918 |
| rs2291742 | rs17045 | kgp428005 | kgp2521934 | kgp7886970 |
| rs2327338 | rs17258415 | kgp5395007 | kgp2622558 | kgp8083724 |
| rs2646357 | rs1883575 | kgp8585564 | kgp2665310 | kgp8184668 |
| rs2829703 | rs2039241 | kgp9237973 | kgp2806942 | kgp8294104 |
| rs3008855 | rs2072941 | kgp7684428 | kgp2894693 | kgp934592 |
| rs404005 | rs2317951 | kgp12355117 | kgp3100977 | kgp8579484 |
| rs4441186 | rs2413786 | kgp544458 | kgp3195305 | kgp8653740 |
| rs4784351 | rs2604913 | kgp7982313 | kgp3325689 | kgp880912 |
| rs4851522 | rs2826121 | kgp10056938 | kgp345319 | kgp891139 |
| rs4976032 | rs3744350 | kgp10225481 | kgp3486275 | kgp9046560 |
| rs6129182 | rs384105 | kgp10278880 | kgp3680788 | kgp9130134 |
| rs6537704 | rs4509646 | kgp10446645 | kgp3938095 | kgp9488489 |
| rs7302922 | rs4912314 | kgp10545153 | kgp4007968 | kgp955389 |
| rs7483731 | rs4953915 | kgp10648217 | kgp4001783 | kgp97489 |
| rs7761747 | rs6025645 | kgp10683029 | kgp4237644 | kgp9882080 |
| rs8070676 | rs6558873 | kgp10838843 | kgp4403116 | kgp1429225 |
| rs876964 | rs6582013 | kgp10923162 | kgp4572570 | kgp1645939 |
| rs9396802 | rs6757976 | kgp1110184 | kgp4679901 | rs1386253 |

Figure 18:
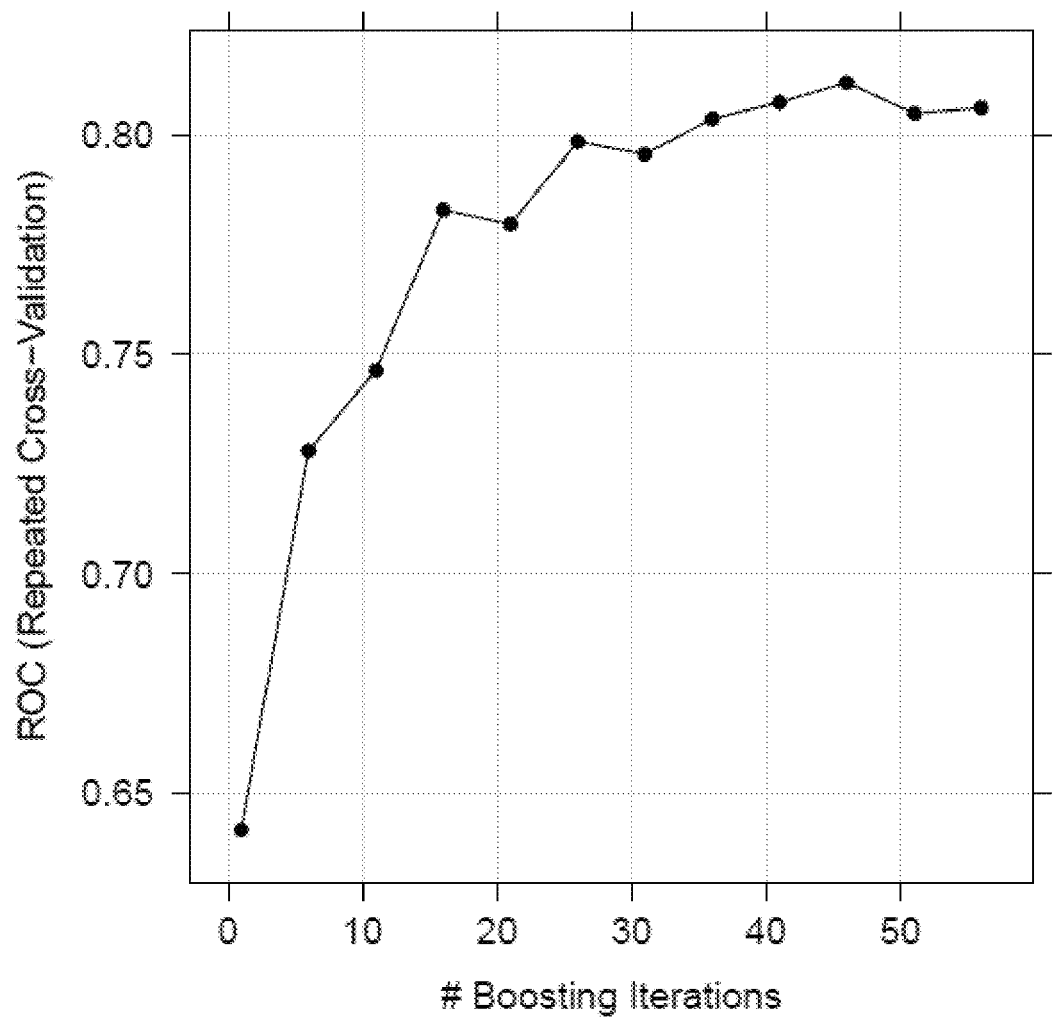
Figure 19:
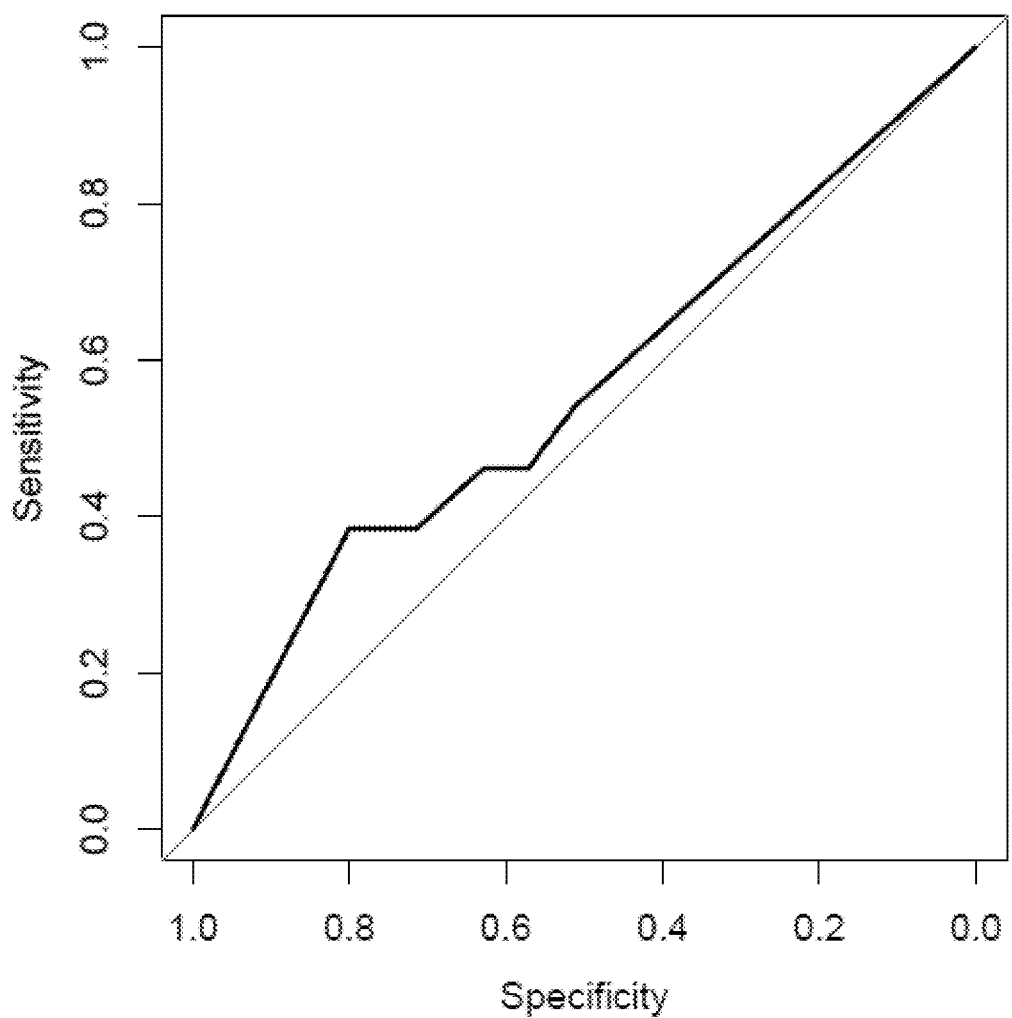
Figure 20:
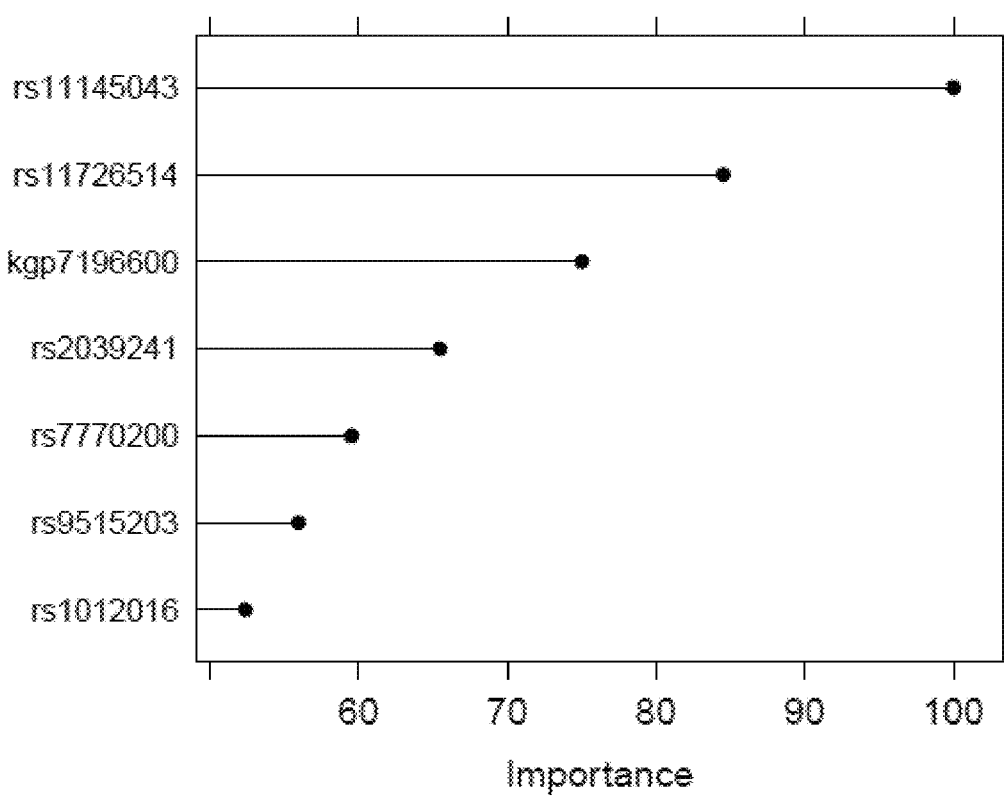

FIG. 18 depicts an example diagram showing the tuning parameter profile for the C5.0 model related to the filtered SNPs. The optimal number of trials (iterations) for this data is 46. The distribution of affected/unaffected subjects based on the filtered SNPs is presented in Table 12, where Y-axis indicates predicted affected/unaffected subjects and X-axis indicates observed affected/unaffected subjects. FIG. 19 depicts an example diagram showing a ROC curve related to the filtered SNPs. FIG. 20 depicts an example diagram showing top important predictors among the filtered SNPs.

TABLE 12

| | Affected | Unaffected |
|---|---|---|
| Affected | 18 | 6 |
| Unaffected | 17 | 7 |

6.3.1.6 Simple Ensemble Approach: Clinical Predictions, Selected and Filtered SNPs Predictions A simple ensemble approach is applied to determine a simple average of test set predicted probabilities to classify subjects into the affected and unaffected categories. The distribution of affected/unaffected subjects based on the simple ensemble approach is presented in Table 13, where Y-axis indicates predicted affected/unaffected subjects and X-axis indicates observed affected/unaffected subjects.

TABLE 13

|  | Affected | Unaffected |
|---|---|---|
| Affected | 24 | 6 |
| Unaffected | 11 | 7 |

Figure 21:
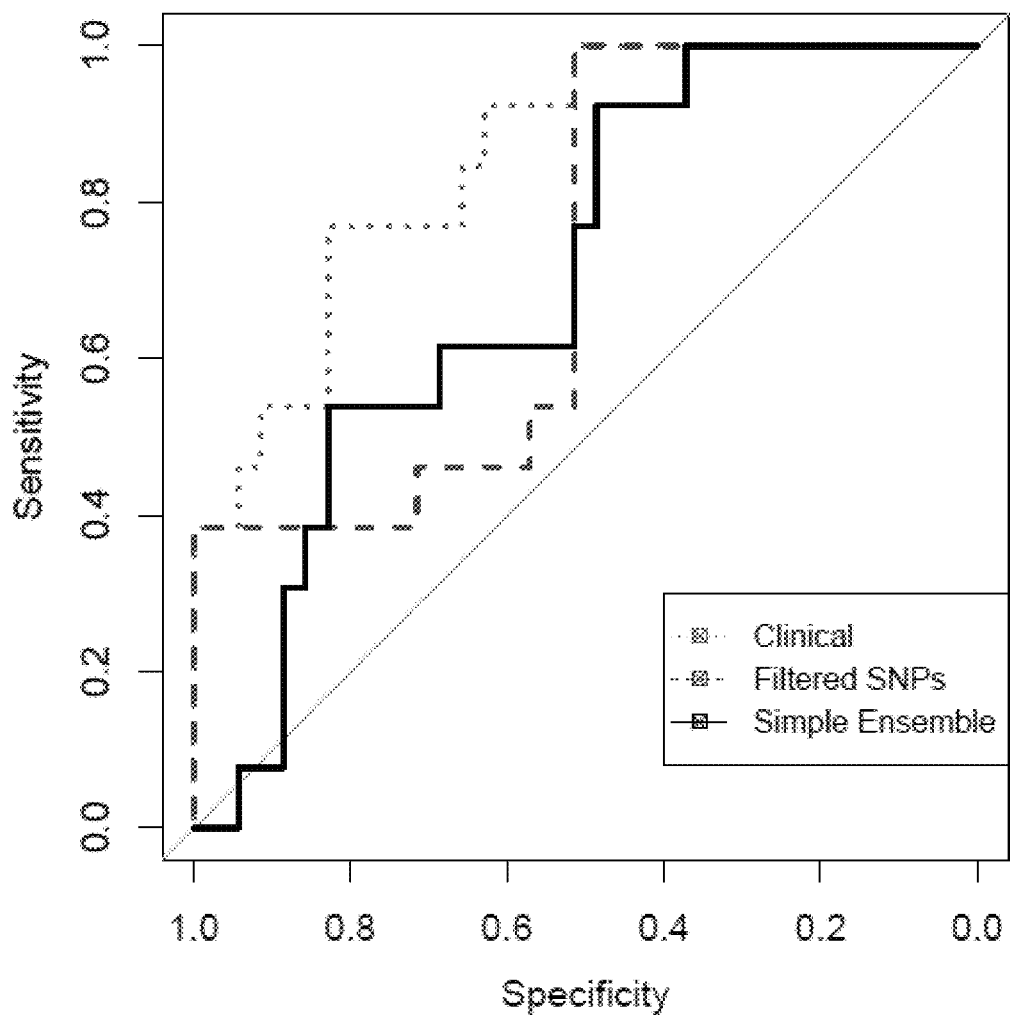

FIG. 21 depicts an example diagram showing a ROC curve based on the average of clinical predictions and selected and filtered SNPs predictions. Table 14 includes prediction data of the simple ensemble approach from calculation based on an average of the model probabilities.

TABLE 14

| Observed | Clinical | Selected | Filtered | Ensemble | Ensemble Pred |
|---|---|---|---|---|---|
| Affected | 0.32 | 0.27 | 0.08 | 0.22 | Unaffected |
| Affected | 1.00 | 0.12 | 0.17 | 0.43 | Unaffected |
| Affected | 1.00 | 0.75 | 0.08 | 0.61 | Affected |
| Affected | 0.33 | 0.79 | 0.04 | 0.39 | Unaffected |
| Affected | 0.33 | 0.12 | 0.06 | 0.17 | Unaffected |
| Affected | 1.00 | 0.27 | 0.99 | 0.75 | Affected |
| Affected | 0.00 | 0.79 | 0.99 | 0.59 | Affected |
| Affected | 0.32 | 0.12 | 0.99 | 0.48 | Unaffected |
| Unaffected | 0.00 | 0.70 | 0.08 | 0.26 | Unaffected |
| Unaffected | 0.00 | 0.75 | 0.99 | 0.58 | Affected |
| Affected | 0.40 | 0.27 | 0.04 | 0.23 | Unaffected |
| Unaffected | 0.00 | 0.90 | 0.90 | 0.63 | Affected |
| Affected | 0.71 | 0.78 | 0.04 | 0.51 | Affected |
| Unaffected | 0.32 | 0.78 | 0.04 | 0.38 | Unaffected |
| Unaffected | 0.40 | 0.27 | 0.99 | 0.55 | Affected |
| Affected | 0.66 | 0.79 | 0.08 | 0.51 | Affected |
| Affected | 0.71 | 0.79 | 0.04 | 0.51 | Affected |
| Affected | 0.40 | 0.12 | 0.99 | 0.50 | Affected |
| Unaffected | 0.29 | 0.78 | 0.12 | 0.40 | Unaffected |
| Affected | 1.00 | 0.12 | 0.99 | 0.70 | Affected |
| Affected | 0.60 | 0.78 | 0.99 | 0.81 | Affected |
| Affected | 1.00 | 0.75 | 0.04 | 0.59 | Affected |
| Affected | 0.33 | 0.78 | 0.99 | 0.70 | Affected |
| Affected | 1.00 | 0.78 | 0.99 | 0.92 | Affected |
| Unaffected | 0.33 | 0.27 | 0.99 | 0.53 | Affected |
| Affected | 0.32 | 0.78 | 0.17 | 0.42 | Unaffected |
| Unaffected | 0.33 | 0.27 | 0.99 | 0.53 | Affected |
| Affected | 0.70 | 0.78 | 0.99 | 0.82 | Affected |
| Affected | 0.66 | 0.78 | 0.12 | 0.52 | Affected |
| Affected | 0.70 | 0.78 | 0.06 | 0.51 | Affected |
| Affected | 1.00 | 0.79 | 0.99 | 0.93 | Affected |
| Affected | 1.00 | 0.27 | 0.99 | 0.75 | Affected |
| Affected | 1.00 | 0.27 | 0.04 | 0.44 | Unaffected |
| Unaffected | 0.00 | 0.27 | 0.99 | 0.42 | Unaffected |
| Affected | 1.00 | 0.79 | 0.06 | 0.62 | Affected |
| Affected | 0.66 | 0.90 | 0.04 | 0.53 | Affected |
| Affected | 1.00 | 0.78 | 0.99 | 0.92 | Affected |
| Affected | 0.33 | 0.78 | 0.17 | 0.43 | Unaffected |
| Affected | 1.00 | 0.12 | 0.99 | 0.70 | Affected |
| Unaffected | 0.66 | 0.27 | 0.04 | 0.32 | Unaffected |
| Unaffected | 0.69 | 0.78 | 0.04 | 0.50 | Affected |
| Unaffected | 0.00 | 0.12 | 0.99 | 0.37 | Unaffected |
| Unaffected | 0.32 | 0.27 | 0.04 | 0.21 | Unaffected |
| Affected | 0.29 | 0.27 | 0.04 | 0.20 | Unaffected |
| Affected | 0.00 | 0.12 | 0.99 | 0.37 | Unaffected |
| Affected | 1.00 | 0.75 | 0.99 | 0.91 | Affected |
| Affected | 1.00 | 0.27 | 0.99 | 0.75 | Affected |
| Affected | 0.36 | 0.90 | 0.99 | 0.75 | Affected |

Figure 22:
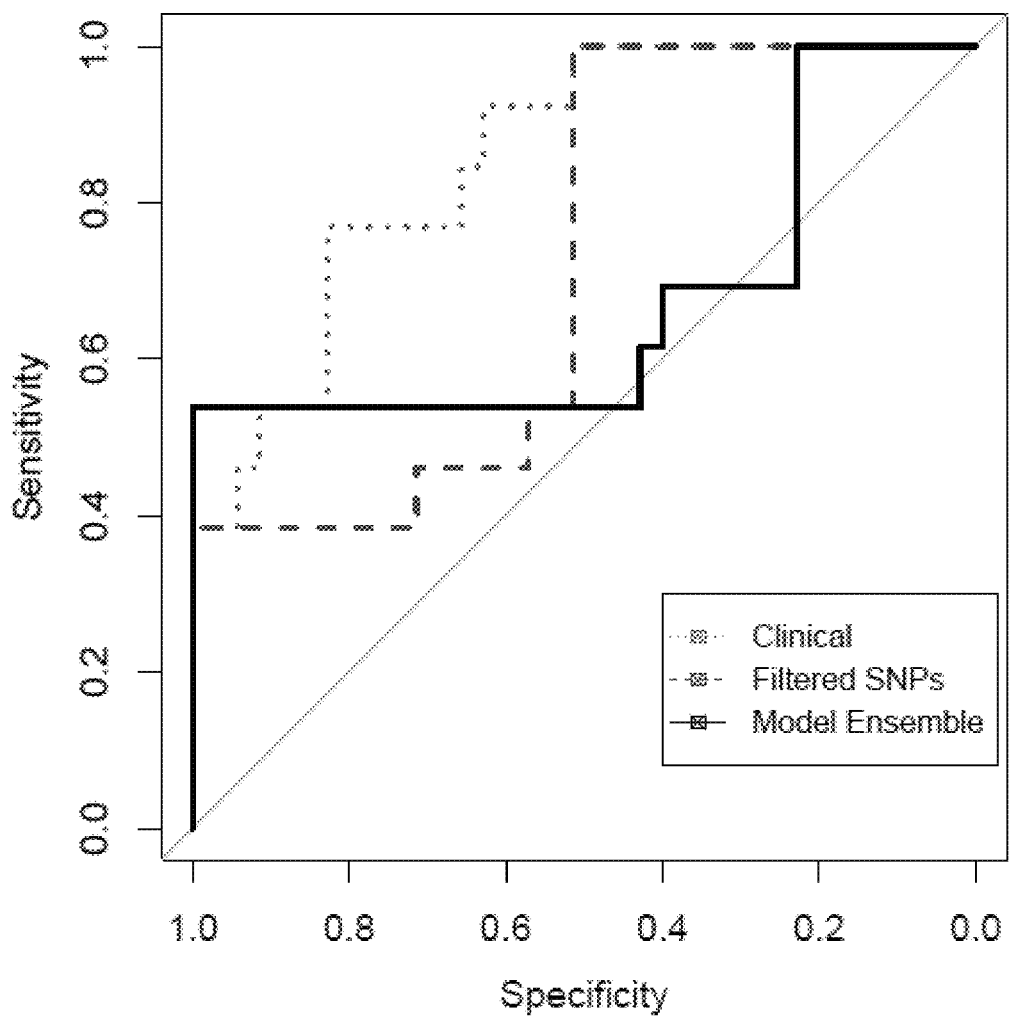

6.3.1.7 Model-Based Ensemble Approach: Clinical Predictions, Selected and Filtered SNPs Predictions A logistic regression model is built on the hold-out datasets in the previous training step using the optimal tuning parameters. The logistic regression model is then applied to the test set. The distribution of affected/unaffected subjects based on a cross-validated model using the clinical predictions and selected and filtered SNPs predictions is presented in Table 15, where Y-axis indicates predicted affected/unaffected subjects and X-axis indicates observed affected/unaffected subjects. FIG. 22 depicts an example diagram showing a ROC curve based on clinical predictions and selected and filtered SNPs predictions using a model. Table 16 includes prediction data of the mode-based ensemble approach from calculation based on a model of the model probabilities.

TABLE 15

|  | Affected | Unaffected |
|---|---|---|
| Affected | 17 | 7 |
| Unaffected | 18 | 6 |

TABLE 16

| Observed | Clinical | Selected | Filtered | Model | Model Pred |
|---|---|---|---|---|---|
| Affected | 0.32 | 0.27 | 0.08 | 0.49 | Unaffected |
| Affected | 1.00 | 0.12 | 0.17 | 0.50 | Unaffected |
| Affected | 1.00 | 0.75 | 0.08 | 0.49 | Unaffected |
| Affected | 0.33 | 0.79 | 0.04 | 0.49 | Unaffected |
| Affected | 0.33 | 0.12 | 0.06 | 0.49 | Unaffected |
| Affected | 1.00 | 0.27 | 0.99 | 0.51 | Affected |
| Affected | 0.00 | 0.79 | 0.99 | 0.51 | Affected |
| Affected | 0.32 | 0.12 | 0.99 | 0.51 | Affected |
| Unaffected | 0.00 | 0.70 | 0.08 | 0.49 | Unaffected |
| Unaffected | 0.00 | 0.75 | 0.99 | 0.51 | Affected |
| Affected | 0.40 | 0.27 | 0.04 | 0.49 | Unaffected |
| Unaffected | 0.00 | 0.90 | 0.99 | 0.51 | Affected |
| Affected | 0.71 | 0.78 | 0.04 | 0.49 | Unaffected |
| Unaffected | 0.32 | 0.78 | 0.04 | 0.49 | Unaffected |
| Unaffected | 0.40 | 0.27 | 0.99 | 0.51 | Affected |
| Affected | 0.66 | 0.79 | 0.08 | 0.49 | Unaffected |
| Affected | 0.71 | 0.79 | 0.04 | 0.49 | Unaffected |
| Affected | 0.39 | 0.12 | 0.99 | 0.51 | Affected |
| Unaffected | 0.29 | 0.78 | 0.12 | 0.49 | Unaffected |
| Affected | 1.00 | 0.12 | 0.99 | 0.51 | Affected |
| Affected | 0.66 | 0.78 | 0.99 | 0.51 | Affected |
| Affected | 1.00 | 0.75 | 0.04 | 0.49 | Unaffected |
| Affected | 0.33 | 0.78 | 0.99 | 0.51 | Affected |
| Affected | 1.00 | 0.78 | 0.99 | 0.51 | Affected |
| Unaffected | 0.33 | 0.27 | 0.99 | 0.51 | Affected |
| Affected | 0.32 | 0.78 | 0.17 | 0.50 | Unaffected |
| Unaffected | 0.33 | 0.27 | 0.99 | 0.51 | Affected |
| Affected | 0.70 | 0.78 | 0.99 | 0.51 | Affected |
| Affected | 0.66 | 0.78 | 0.12 | 0.49 | Unaffected |
| Affected | 0.70 | 0.78 | 0.06 | 0.49 | Unaffected |
| Affected | 1.00 | 0.79 | 0.99 | 0.51 | Affected |
| Affected | 1.00 | 0.27 | 0.99 | 0.51 | Affected |
| Affected | 1.00 | 0.27 | 0.04 | 0.49 | Unaffected |
| Unaffected | 0.00 | 0.27 | 0.99 | 0.51 | Affected |
| Affected | 1.00 | 0.79 | 0.06 | 0.49 | Unaffected |
| Affected | 0.66 | 0.90 | 0.04 | 0.49 | Unaffected |
| Affected | 1.00 | 0.78 | 0.99 | 0.51 | Affected |
| Affected | 0.33 | 0.78 | 0.17 | 0.50 | Unaffected |
| Affected | 1.00 | 0.12 | 0.99 | 0.51 | Affected |
| Unaffected | 0.66 | 0.27 | 0.04 | 0.49 | Unaffected |
| Unaffected | 0.69 | 0.78 | 0.04 | 0.49 | Unaffected |
| Unaffected | 0.00 | 0.12 | 0.99 | 0.51 | Affected |
| Unaffected | 0.33 | 0.27 | 0.04 | 0.49 | Unaffected |
| Affected | 0.29 | 0.27 | 0.04 | 0.49 | Unaffected |
| Affected | 0.00 | 0.12 | 0.99 | 0.51 | Affected |
| Affected | 1.00 | 0.75 | 0.99 | 0.51 | Affected |
| Affected | 1.00 | 0.27 | 0.99 | 0.51 | Affected |
| Affected | 0.36 | 0.90 | 0.99 | 0.51 | Affected |

6.3.2 Random Forests
6.3.2.1 Clinical Predictors

Figure 23:
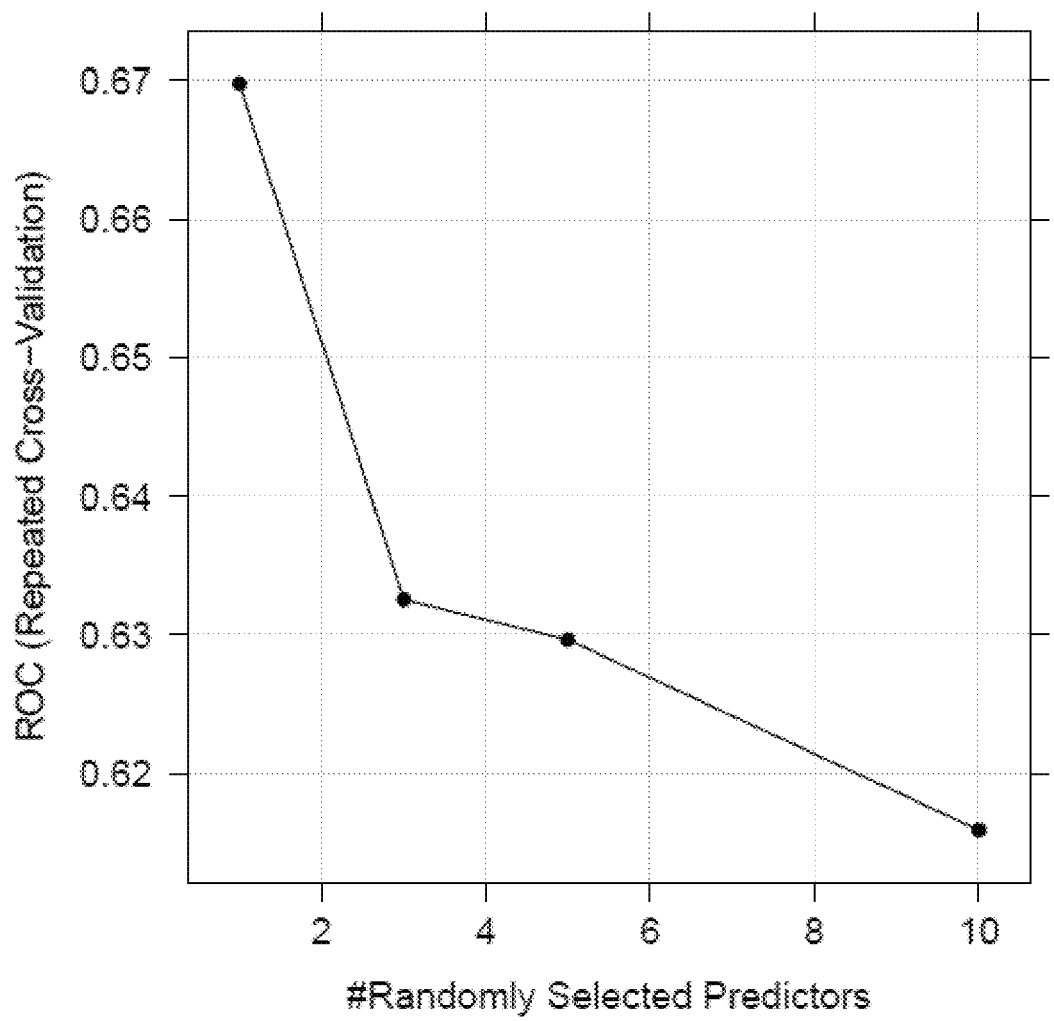

FIG. 23 depicts an example diagram showing the tuning parameter profile for the random forests model related to clinical predictors. The optimal number of predictors randomly selected at each split for this data is 1. The distribution of affected/unaffected subjects based on the clinical predictors is presented in Table 17, where Y-axis indicates predicted affected/unaffected subjects and X-axis indicates observed affected/unaffected subjects.

TABLE 17

|  | Affected | Unaffected |
| --- | --- | --- |
| Affected | 20 | 3 |
| Unaffected | 15 | 10 |

Figure 24:
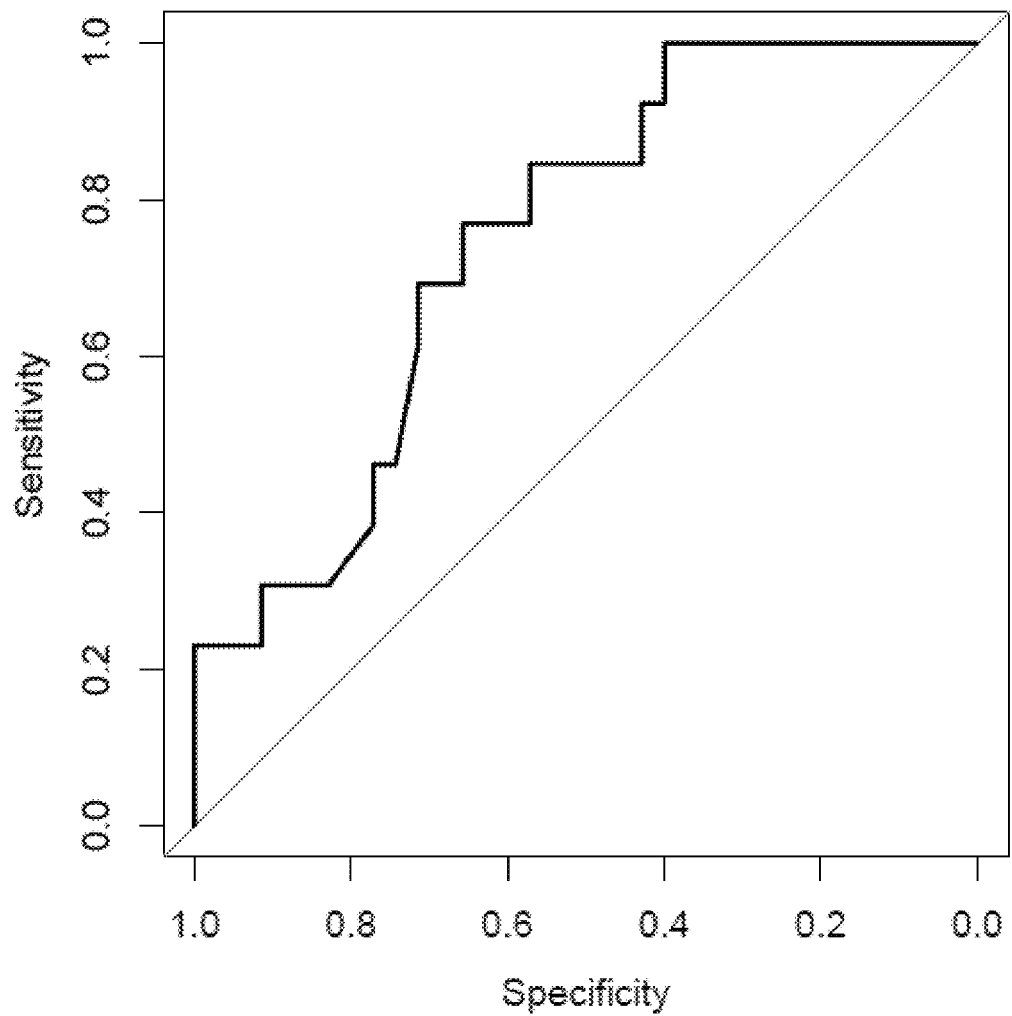
Figure 25:
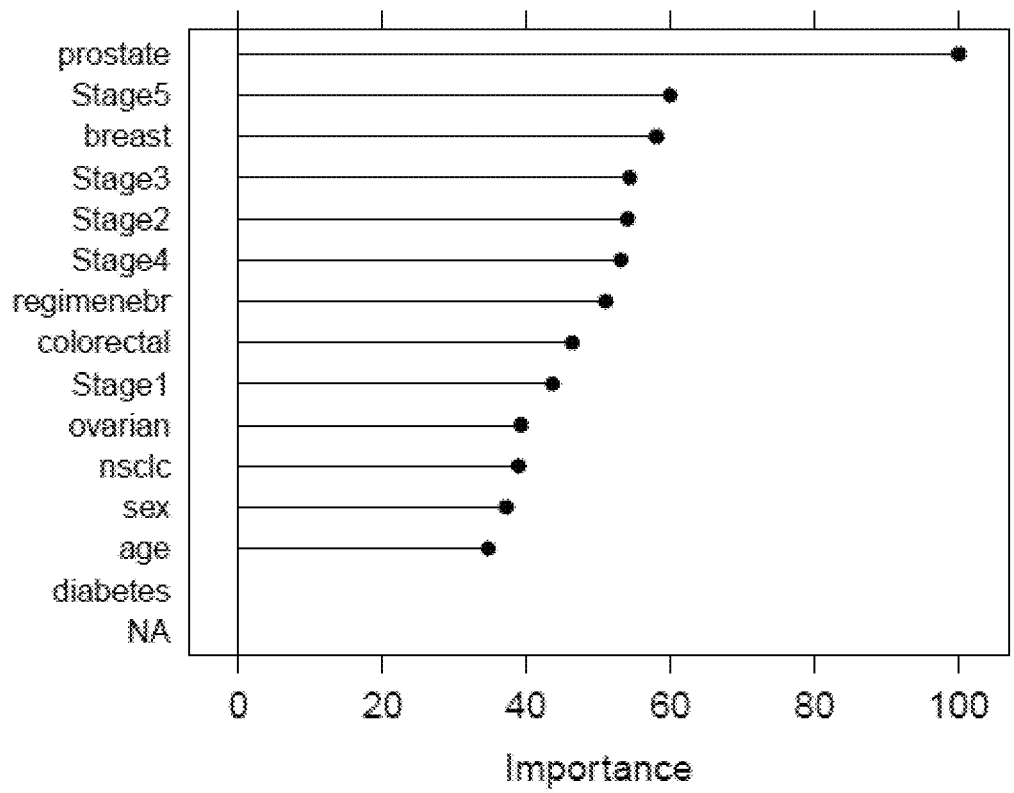

FIG. 24 depicts an example diagram showing a random forest test set ROC curve related to the clinical predictors. FIG. 25 depicts an example diagram showing random forest top important predictors among the clinical predictors.

6.3.2.2 Selected SNPs

Figure 26:
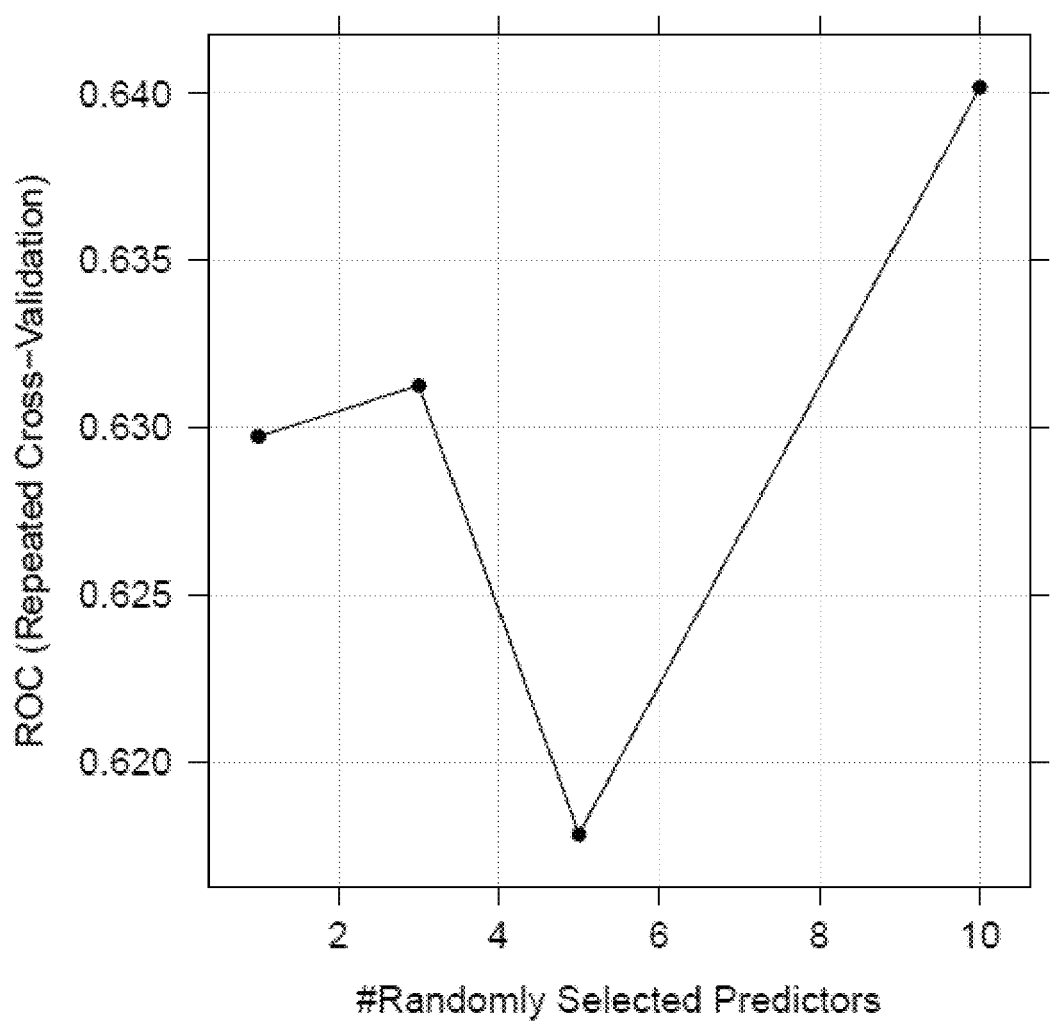

FIG. 26 depicts an example diagram showing the tuning parameter profile for the random forests model related to the selected SNPs. The optimal number of predictors randomly selected at each iteration for this data is 10. The distribution of affected/unaffected subjects based on the selected SNPs is presented in Table 18, where Y-axis indicates predicted affected/unaffected subjects and X-axis indicates observed affected/unaffected subjects.

TABLE 18

|  | Affected | Unaffected |
| --- | --- | --- |
| Affected | 16 | 7 |
| Unaffected | 19 | 6 |

Figure 27:
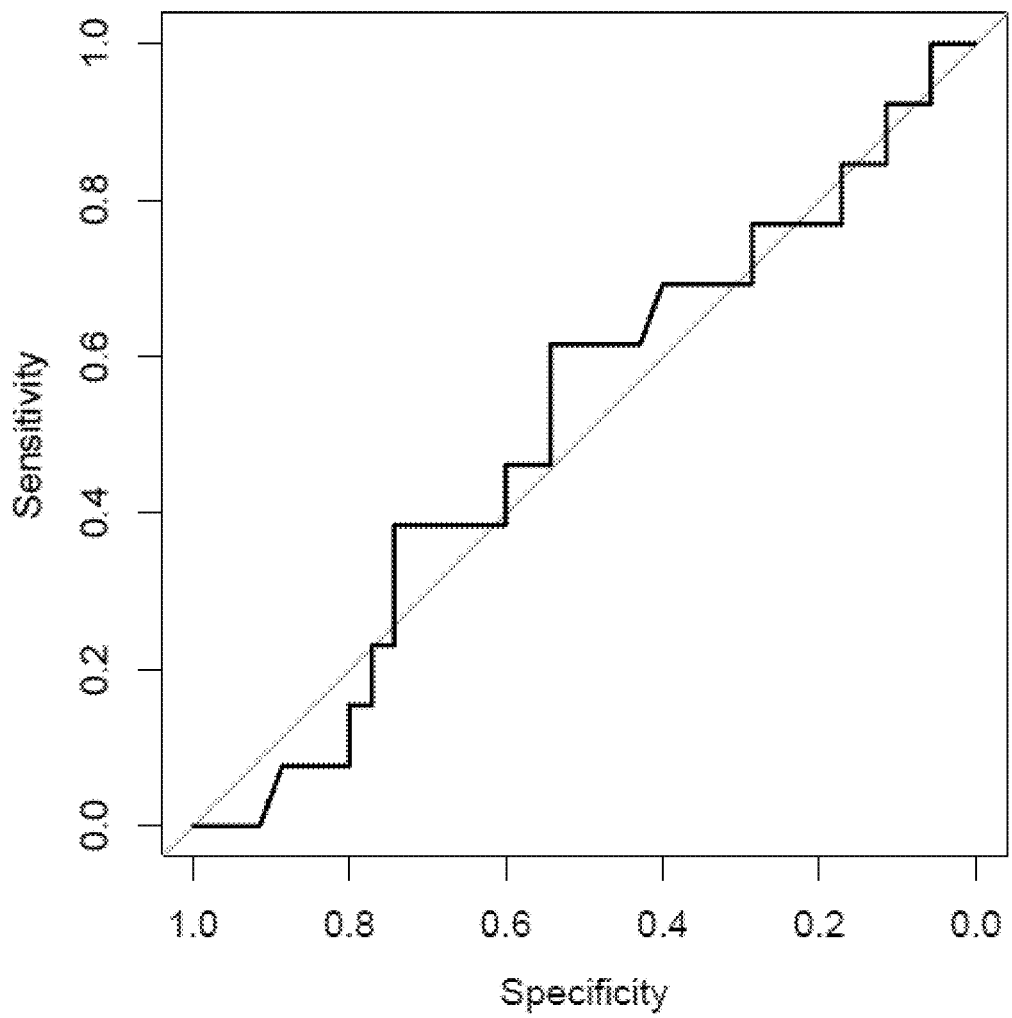
Figure 28:
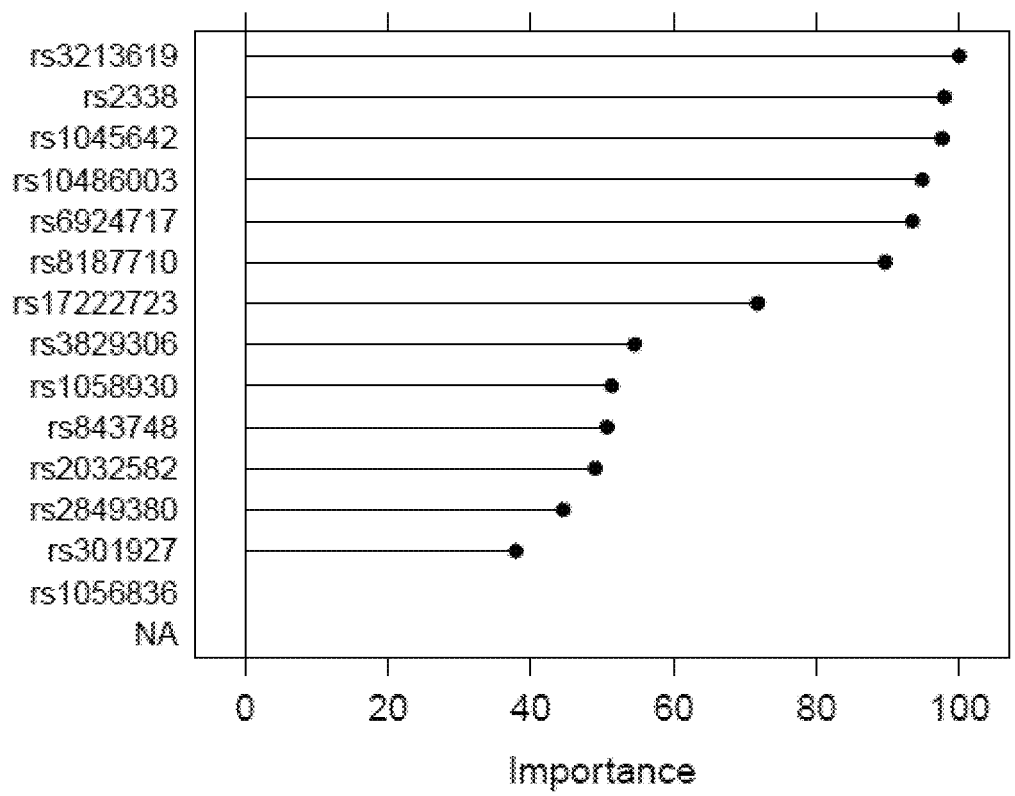

FIG. 27 depicts an example diagram showing a random forest test set ROC curve related to the selected SNPs. FIG. 28 depicts an example diagram showing random forest top important predictors among the selected SNPs.

Figure 29:
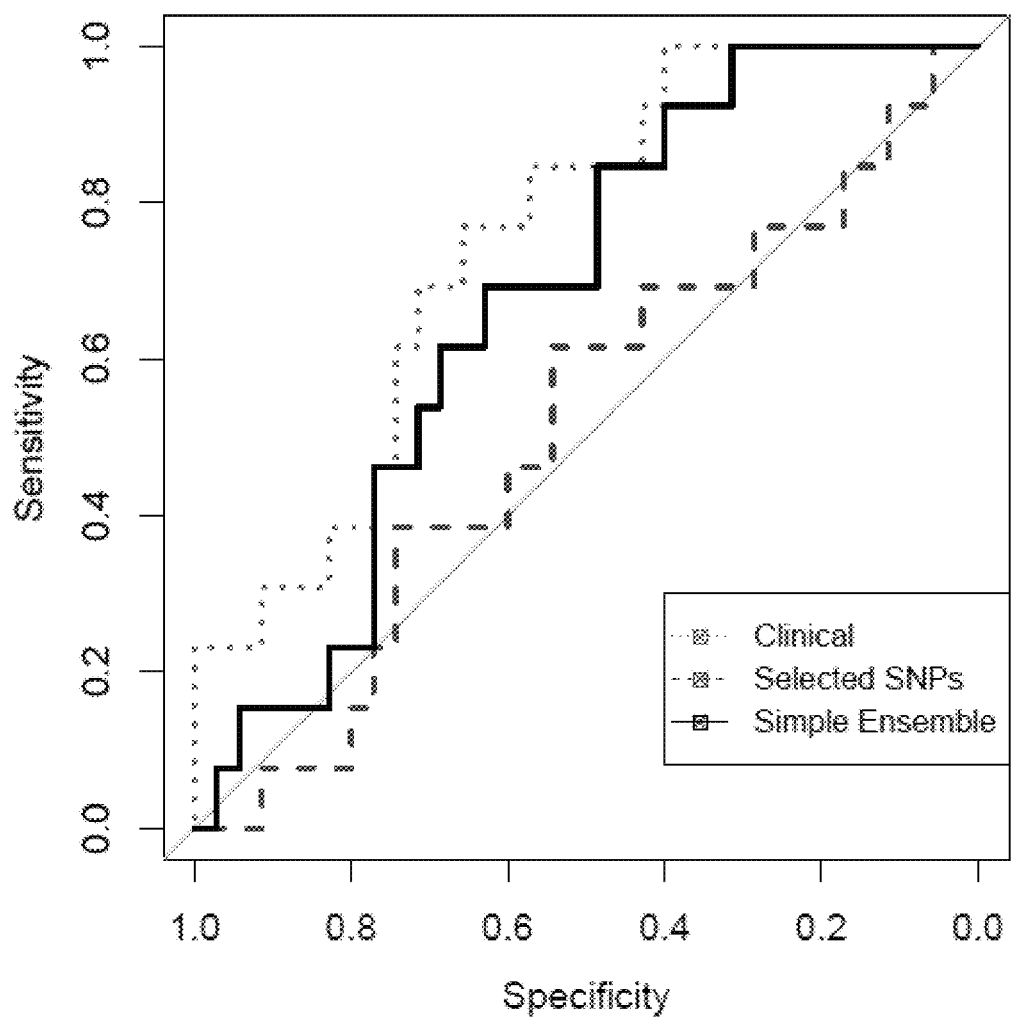

6.3.2.3 Simple Ensemble Approach: Clinical Predictions and Selected SNPs Predictions A simple ensemble approach is applied to determine a simple average of test set predicted probabilities to classify subjects into the affected and unaffected categories. FIG. 29 depicts an example diagram showing a ROC curve based on the average of clinical predictions and selected SNPs predictions. The distribution of affected/unaffected subjects based on the simple ensemble approach for the random forest model is presented in Table 19, where Y-axis indicates predicted affected/unaffected subjects and X-axis indicates observed affected/unaffected subjects. Table 20 includes prediction data of the simple ensemble approach from calculation based on an average of the model probabilities for random forest models.

TABLE 19

|  | Affected | Unaffected |
| --- | --- | --- |
| Affected | 21 | 4 |
| Unaffected | 14 | 9 |

TABLE 20

| Observed | Clinical | Selected | Ensemble | Ensemble Pred |
| --- | --- | --- | --- | --- |
| Affected | 0.36 | 0.39 | 0.38 | Unaffected |
| Affected | 0.84 | 0.45 | 0.64 | Affected |
| Affected | 0.82 | 0.22 | 0.52 | Affected |
| Affected | 0.49 | 0.59 | 0.54 | Affected |
| Affected | 0.58 | 0.45 | 0.52 | Affected |
| Affected | 0.62 | 0.26 | 0.44 | Unaffected |
| Affected | 0.33 | 0.49 | 0.41 | Unaffected |
| Affected | 0.38 | 0.10 | 0.24 | Unaffected |
| Unaffected | 0.26 | 0.72 | 0.49 | Unaffected |
| Unaffected | 0.26 | 0.56 | 0.41 | Unaffected |
| Affected | 0.39 | 0.49 | 0.44 | Unaffected |
| Unaffected | 0.28 | 0.62 | 0.46 | Unaffected |

TABLE 20-continued

| Observed | Clinical | Selected | Ensemble | Ensemble Pred |
| --- | --- | --- | --- | --- |
| Affected | 0.36 | 0.55 | 0.46 | Unaffected |
| Unaffected | 0.42 | 0.51 | 0.46 | Unaffected |
| Unaffected | 0.30 | 0.33 | 0.36 | Unaffected |
| Affected | 0.69 | 0.76 | 0.72 | Affected |
| Affected | 0.42 | 0.31 | 0.36 | Unaffected |
| Affected | 0.36 | 0.38 | 0.37 | Unaffected |
| Unaffected | 0.34 | 0.79 | 0.56 | Affected |
| Affected | 0.73 | 0.43 | 0.58 | Affected |
| Affected | 0.73 | 0.79 | 0.76 | Affected |
| Affected | 0.73 | 0.57 | 0.65 | Affected |
| Affected | 0.49 | 0.59 | 0.54 | Affected |
| Affected | 0.57 | 0.61 | 0.59 | Affected |
| Unaffected | 0.55 | 0.69 | 0.62 | Affected |
| Affected | 0.34 | 0.71 | 0.53 | Affected |
| Unaffected | 0.48 | 0.40 | 0.44 | Unaffected |
| Affected | 0.46 | 0.54 | 0.50 | Unaffected |
| Affected | 0.66 | 0.81 | 0.74 | Affected |
| Affected | 0.56 | 0.41 | 0.48 | Unaffected |
| Affected | 0.46 | 0.33 | 0.39 | Unaffected |
| Affected | 0.72 | 0.24 | 0.48 | Unaffected |
| Affected | 0.83 | 0.73 | 0.78 | Affected |
| Unaffected | 0.44 | 0.30 | 0.37 | Unaffected |
| Affected | 0.57 | 0.84 | 0.71 | Affected |
| Affected | 0.67 | 0.78 | 0.72 | Affected |
| Affected | 0.74 | 0.66 | 0.70 | Affected |
| Affected | 0.40 | 0.90 | 0.70 | Affected |
| Affected | 0.72 | 0.39 | 0.56 | Affected |
| Unaffected | 0.65 | 0.23 | 0.44 | Unaffected |
| Unaffected | 0.42 | 0.64 | 0.53 | Affected |
| Unaffected | 0.38 | 0.50 | 0.44 | Unaffected |
| Unaffected | 0.58 | 0.47 | 0.53 | Affected |
| Affected | 0.34 | 0.47 | 0.40 | Unaffected |
| Affected | 0.38 | 0.48 | 0.43 | Unaffected |
| Affected | 0.68 | 0.56 | 0.62 | Affected |
| Affected | 0.83 | 0.35 | 0.59 | Affected |
| Affected | 0.56 | 0.47 | 0.52 | Affected |

Figure 30:
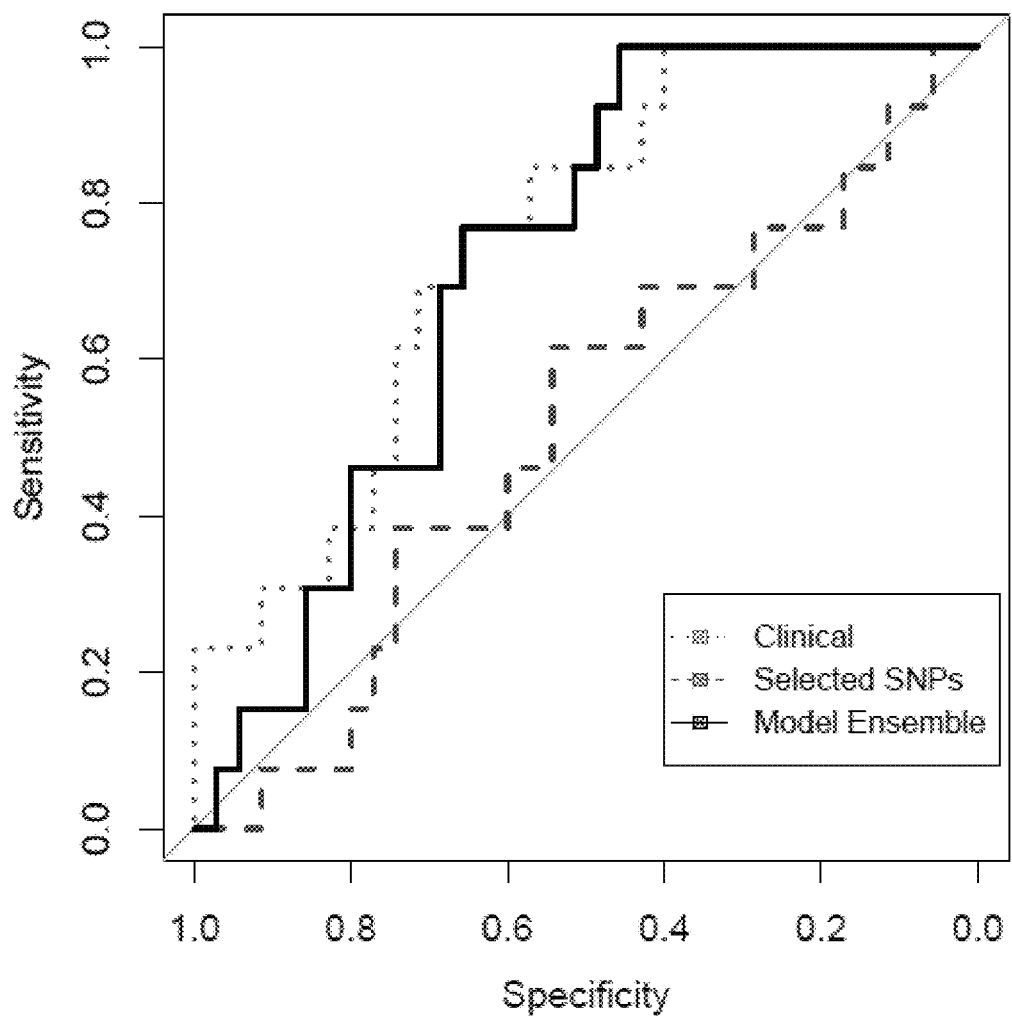

6.3.2.4 Model-Based Ensemble Approach: Clinical Predictions and Selected SNPs Predictions A logistic regression model is built on the hold-out datasets in the previous training step using the optimal tuning parameters. The logistic regression model is then applied to the test set. The distribution of affected/unaffected subjects based on a cross-validated model using the clinical predictions and selected SNPs predictions from random forest models is presented in Table 21, where Y-axis indicates predicted affected/unaffected subjects and X-axis indicates observed affected/unaffected subjects. FIG. 30 depicts an example diagram showing a ROC curve based on clinical predictions and selected SNPs predictions using a model based on the random forest models. Table 22 includes prediction data of the mode-based ensemble approach from calculation based on a model of the model probabilities for the random forest models.

TABLE 21

|  | Affected | Unaffected |
| --- | --- | --- |
| Affected | 12 | 10 |
| Unaffected | 23 | 3 |

TABLE 22

| Observed | Clinical | Selected | Model | Model Pred |
| --- | --- | --- | --- | --- |
| Affected | 0.36 | 0.39 | 0.56 | Affected |
| Affected | 0.84 | 0.44 | 0.40 | Unaffected |
| Affected | 0.82 | 0.22 | 0.43 | Unaffected |
| Affected | 0.49 | 0.59 | 0.50 | Unaffected |
| Affected | 0.58 | 0.45 | 0.48 | Unaffected |

TABLE 22-continued

| Observed | Clinical | Selected | Model | Model Pred |
|---|---|---|---|---|
| Affected | 0.62 | 0.26 | 0.49 | Unaffected |
| Affected | 0.33 | 0.50 | 0.56 | Affected |
| Affected | 0.38 | 0.10 | 0.59 | Affected |
| Unaffected | 0.26 | 0.72 | 0.56 | Affected |
| Unaffected | 0.26 | 0.56 | 0.58 | Affected |
| Affected | 0.39 | 0.50 | 0.54 | Affected |
| Unaffected | 0.28 | 0.62 | 0.56 | Affected |
| Affected | 0.36 | 0.55 | 0.54 | Affected |
| Unaffected | 0.42 | 0.50 | 0.53 | Affected |
| Unaffected | 0.38 | 0.33 | 0.56 | Affected |
| Affected | 0.70 | 0.76 | 0.41 | Unaffected |
| Affected | 0.42 | 0.31 | 0.55 | Affected |
| Affected | 0.36 | 0.38 | 0.56 | Affected |
| Unaffected | 0.34 | 0.78 | 0.52 | Affected |
| Affected | 0.74 | 0.43 | 0.43 | Unaffected |
| Affected | 0.74 | 0.78 | 0.39 | Unaffected |
| Affected | 0.73 | 0.57 | 0.42 | Unaffected |
| Affected | 0.49 | 0.59 | 0.50 | Unaffected |
| Affected | 0.57 | 0.62 | 0.46 | Unaffected |
| Unaffected | 0.55 | 0.69 | 0.46 | Unaffected |
| Affected | 0.34 | 0.71 | 0.53 | Affected |
| Unaffected | 0.48 | 0.40 | 0.52 | Affected |
| Affected | 0.46 | 0.54 | 0.51 | Affected |
| Affected | 0.66 | 0.82 | 0.41 | Unaffected |
| Affected | 0.56 | 0.41 | 0.50 | Unaffected |
| Affected | 0.46 | 0.32 | 0.54 | Affected |
| Affected | 0.72 | 0.24 | 0.46 | Unaffected |
| Affected | 0.84 | 0.73 | 0.37 | Unaffected |
| Unaffected | 0.44 | 0.30 | 0.55 | Affected |
| Affected | 0.57 | 0.84 | 0.44 | Unaffected |
| Affected | 0.67 | 0.78 | 0.41 | Unaffected |
| Affected | 0.74 | 0.66 | 0.41 | Unaffected |
| Affected | 0.50 | 0.90 | 0.46 | Unaffected |
| Affected | 0.72 | 0.39 | 0.44 | Unaffected |
| Unaffected | 0.65 | 0.23 | 0.49 | Unaffected |
| Unaffected | 0.42 | 0.64 | 0.51 | Affected |
| Unaffected | 0.38 | 0.50 | 0.55 | Affected |
| Unaffected | 0.58 | 0.47 | 0.48 | Unaffected |
| Affected | 0.34 | 0.47 | 0.56 | Affected |
| Affected | 0.38 | 0.48 | 0.55 | Affected |
| Affected | 0.68 | 0.56 | 0.44 | Unaffected |
| Affected | 0.84 | 0.36 | 0.41 | Unaffected |
| Affected | 0.56 | 0.48 | 0.49 | Unaffected |

6.3.2.5 Filtered SNPs

Figure 31:
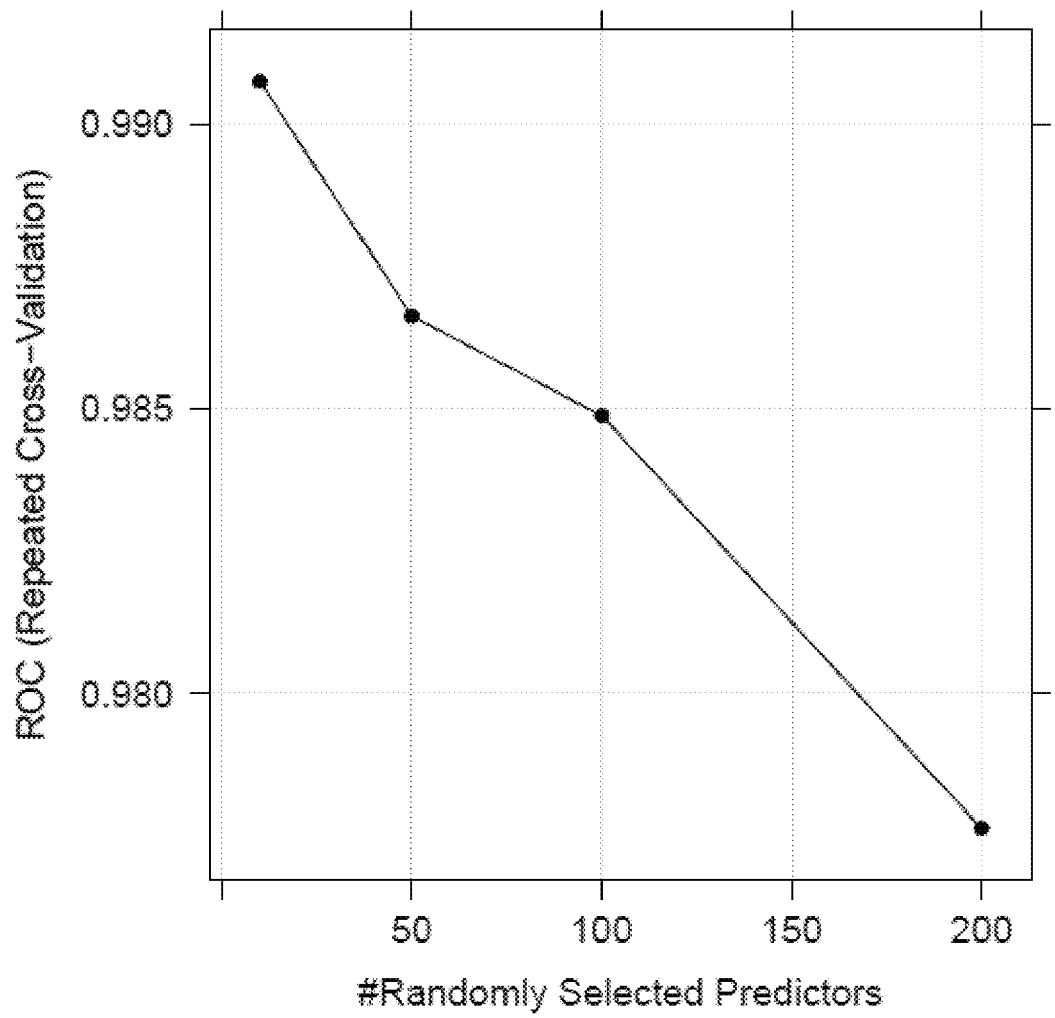
Figure 32:
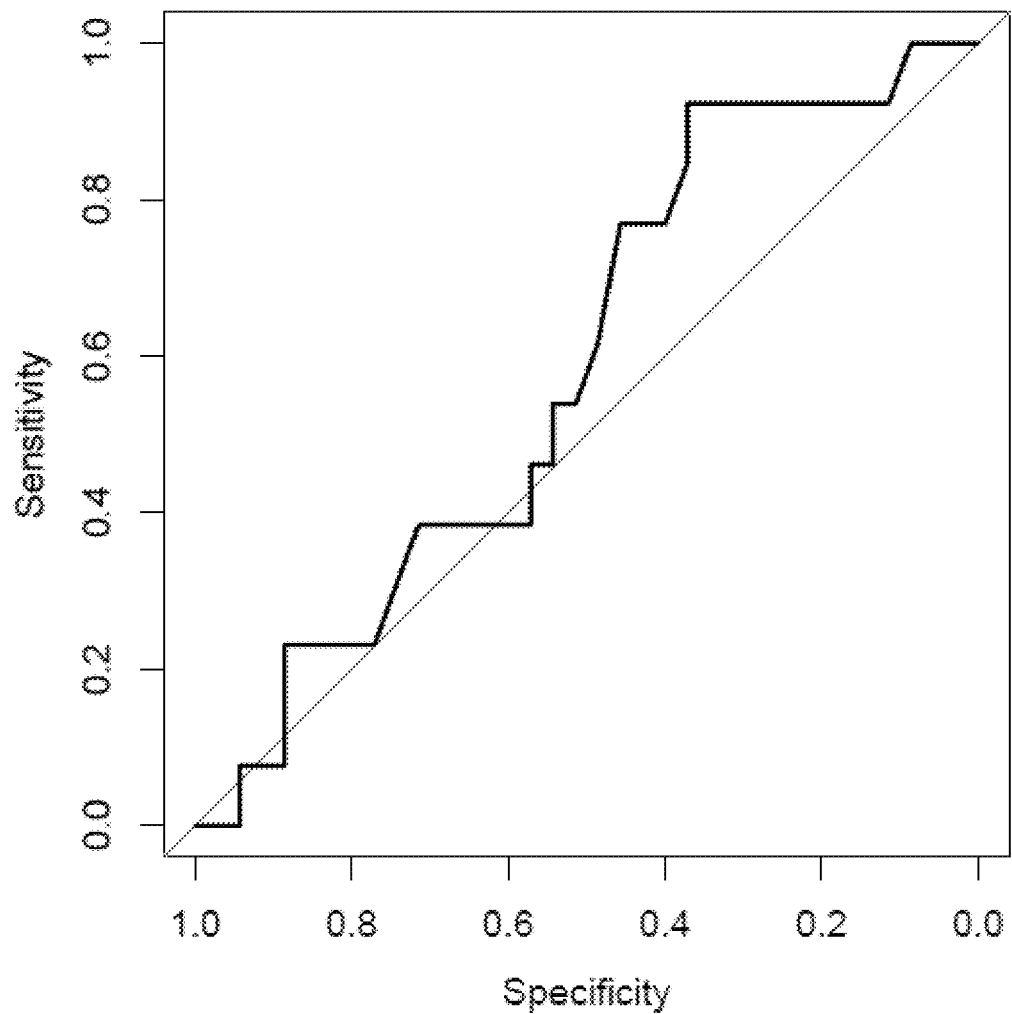
Figure 33:
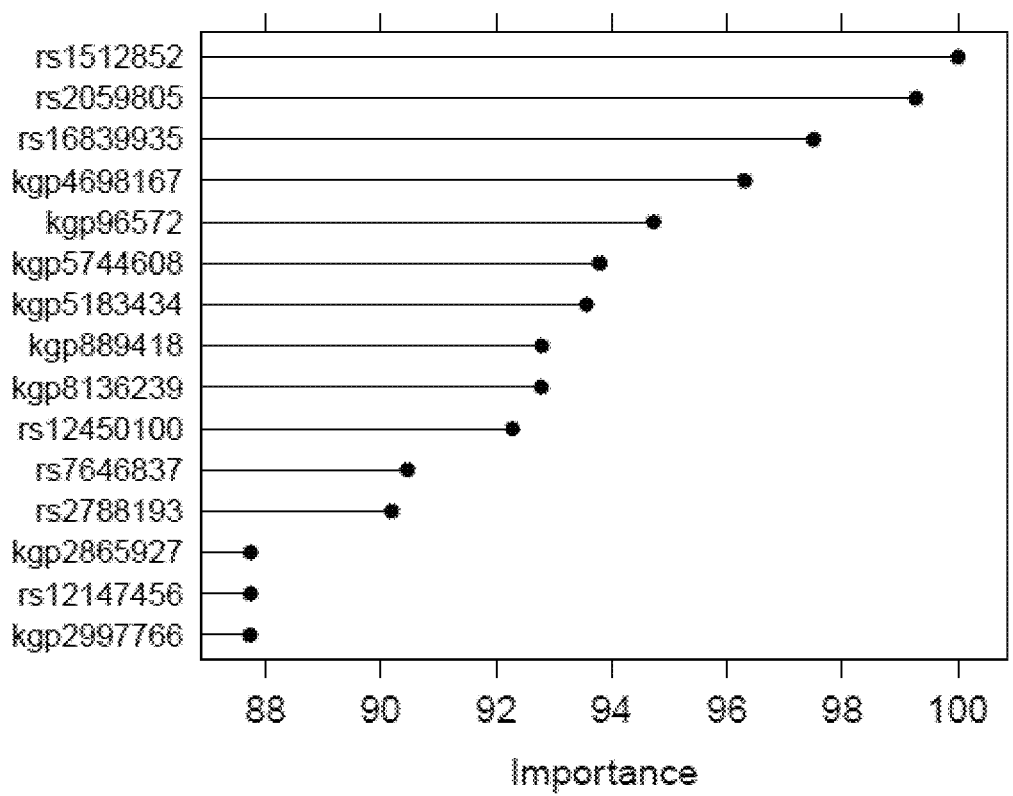

FIG. 31 depicts an example diagram showing the tuning parameter profile for the random forest model related to the filtered SNPs. The cross-validated ROC is high in FIG. 31, indicating that it may be over-fitting, likely due to a high proportion of irrelevant predictors. The optimal number of trials (iterations) for this data is 10. The distribution of affected/unaffected subjects based on the filtered SNPs is presented in Table 23, where Y-axis indicates predicted affected/unaffected subjects and X-axis indicates observed affected/unaffected subjects. FIG. 32 depicts an example diagram showing a random forest test set ROC curve related to the filtered SNPs. FIG. 33 depicts an example diagram showing random forest top important predictors among the filtered SNPs.

TABLE 23

|  | Affected | Unaffected |
|---|---|---|
| Affected | 25 | 12 |
| Unaffected | 10 | 1 |

6.3.2.6 Simple Ensemble Approach: Clinical Predictions, Selected and Filtered SNPs Predictions A simple ensemble approach is applied to determine a simple average of test set predicted probabilities to classify subjects into the affected and unaffected categories. The distribution of affected/unaffected subjects based on the average of clinical predictions and selected and filtered SNPs predictions for random forest models is presented in Table 24, where Y-axis indicates predicted affected/unaffected subjects and X-axis indicates observed affected/unaffected subjects.

TABLE 24

|  | Affected | Unaffected |
|---|---|---|
| Affected | 23 | 7 |
| Unaffected | 12 | 6 |

Figure 34:
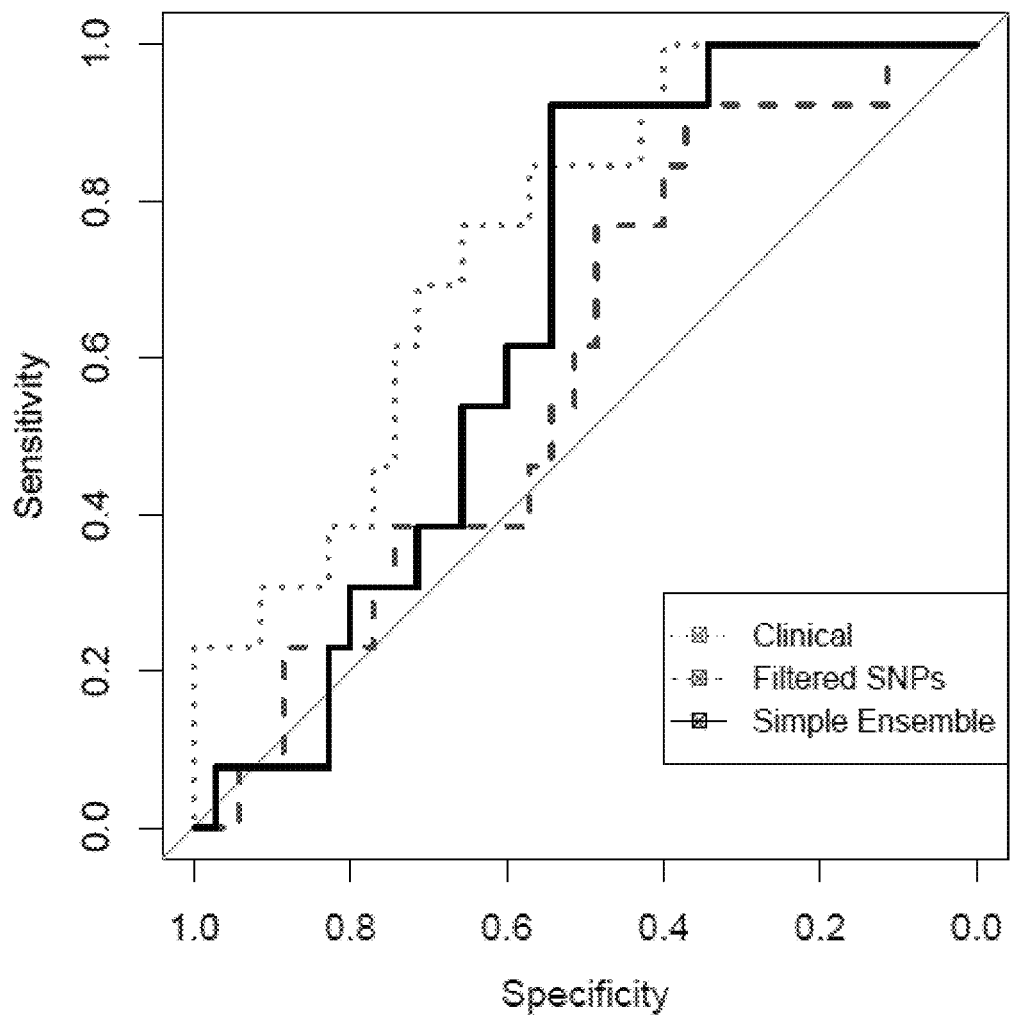

FIG. 34 depicts an example diagram showing a ROC curve based on the average of clinical predictions and selected and filtered SNPs predictions for random forest models. Table 25 includes prediction data of the simple ensemble approach from calculation based on an average of the model probabilities.

TABLE 25

| Observed | Clinical | Selected | Filtered | Ensemble | Ensemble Pred |
|---|---|---|---|---|---|
| Affected | 0.36 | 0.39 | 0.46 | 0.40 | Unaffected |
| Affected | 0.84 | 0.45 | 0.57 | 0.62 | Affected |
| Affected | 0.82 | 0.22 | 0.48 | 0.51 | Affected |
| Affected | 0.49 | 0.59 | 0.46 | 0.51 | Affected |
| Affected | 0.59 | 0.45 | 0.50 | 0.51 | Affected |
| Affected | 0.62 | 0.26 | 0.59 | 0.49 | Unaffected |
| Affected | 0.33 | 0.49 | 0.53 | 0.45 | Unaffected |
| Affected | 0.38 | 0.10 | 0.58 | 0.35 | Unaffected |
| Unaffected | 0.26 | 0.72 | 0.51 | 0.49 | Unaffected |
| Unaffected | 0.26 | 0.56 | 0.51 | 0.44 | Unaffected |
| Affected | 0.39 | 0.49 | 0.57 | 0.48 | Unaffected |
| Unaffected | 0.28 | 0.62 | 0.64 | 0.52 | Affected |
| Affected | 0.36 | 0.55 | 0.52 | 0.47 | Unaffected |
| Unaffected | 0.42 | 0.51 | 0.54 | 0.49 | Unaffected |
| Unaffected | 0.39 | 0.33 | 0.46 | 0.39 | Unaffected |
| Affected | 0.69 | 0.76 | 0.49 | 0.65 | Affected |
| Affected | 0.42 | 0.31 | 0.50 | 0.41 | Unaffected |
| Affected | 0.36 | 0.38 | 0.47 | 0.40 | Unaffected |
| Unaffected | 0.34 | 0.79 | 0.46 | 0.53 | Affected |
| Affected | 0.73 | 0.43 | 0.65 | 0.60 | Affected |
| Affected | 0.73 | 0.79 | 0.60 | 0.71 | Affected |
| Affected | 0.73 | 0.57 | 0.55 | 0.61 | Affected |
| Affected | 0.49 | 0.59 | 0.68 | 0.59 | Affected |
| Affected | 0.57 | 0.61 | 0.58 | 0.59 | Affected |
| Unaffected | 0.55 | 0.69 | 0.54 | 0.59 | Affected |
| Affected | 0.34 | 0.71 | 0.59 | 0.55 | Affected |
| Unaffected | 0.48 | 0.40 | 0.64 | 0.51 | Affected |
| Affected | 0.46 | 0.54 | 0.64 | 0.54 | Affected |
| Affected | 0.66 | 0.81 | 0.64 | 0.70 | Affected |
| Affected | 0.56 | 0.41 | 0.48 | 0.48 | Unaffected |
| Affected | 0.46 | 0.33 | 0.54 | 0.44 | Unaffected |
| Affected | 0.72 | 0.24 | 0.67 | 0.54 | Affected |
| Affected | 0.83 | 0.73 | 0.47 | 0.68 | Affected |
| Unaffected | 0.44 | 0.30 | 0.60 | 0.45 | Unaffected |
| Affected | 0.57 | 0.84 | 0.56 | 0.66 | Affected |
| Affected | 0.67 | 0.78 | 0.53 | 0.66 | Affected |
| Affected | 0.74 | 0.66 | 0.63 | 0.68 | Affected |
| Affected | 0.49 | 0.90 | 0.55 | 0.65 | Affected |
| Affected | 0.72 | 0.39 | 0.65 | 0.59 | Affected |
| Unaffected | 0.65 | 0.23 | 0.53 | 0.47 | Unaffected |
| Unaffected | 0.42 | 0.64 | 0.53 | 0.53 | Affected |
| Unaffected | 0.38 | 0.50 | 0.66 | 0.51 | Affected |
| Unaffected | 0.58 | 0.47 | 0.56 | 0.54 | Affected |
| Affected | 0.34 | 0.47 | 0.51 | 0.44 | Unaffected |
| Affected | 0.38 | 0.48 | 0.62 | 0.49 | Unaffected |
| Affected | 0.68 | 0.56 | 0.46 | 0.57 | Affected |
| Affected | 0.83 | 0.35 | 0.50 | 0.56 | Affected |
| Affected | 0.56 | 0.47 | 0.50 | 0.51 | Affected |

Figure 35:
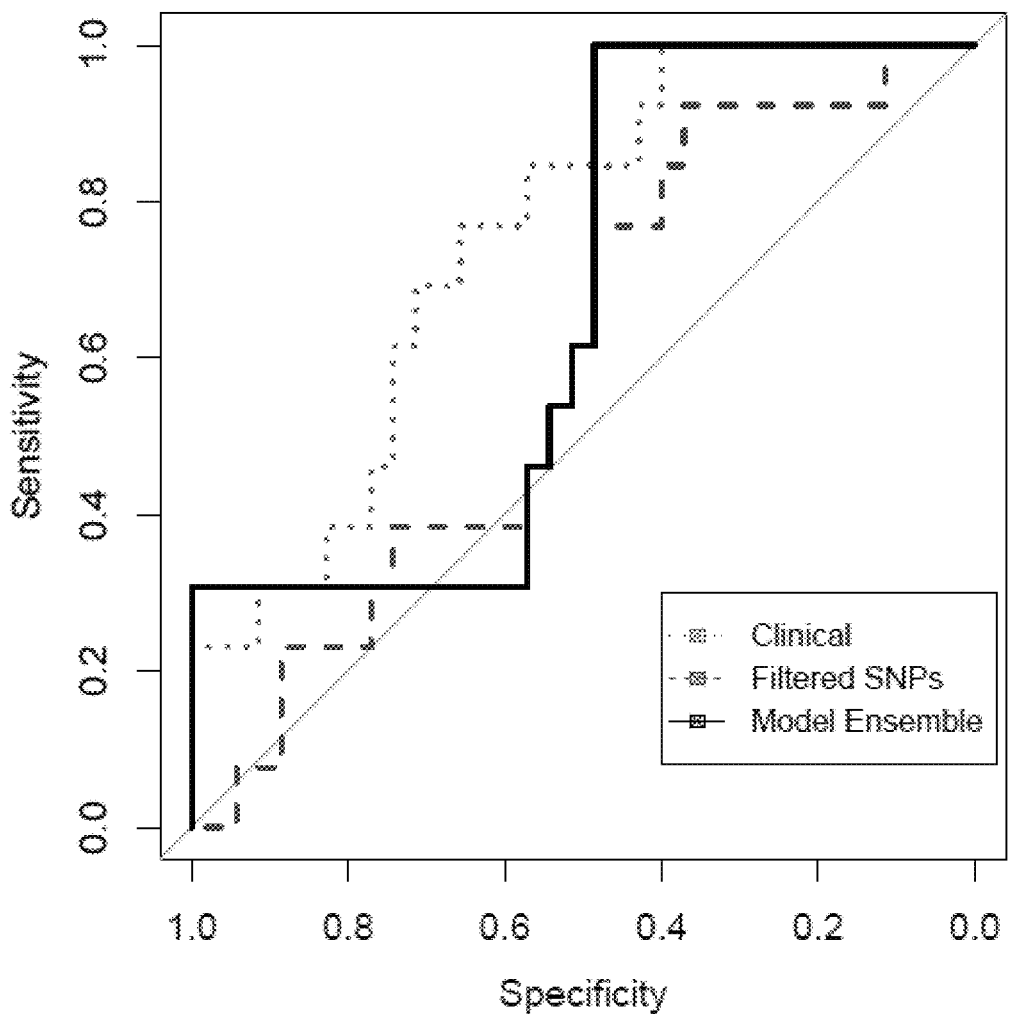

6.3.2.7 Model-Based Ensemble Approach: Clinical Predictions, Selected and Filtered SNPs Predictions A logistic regression model is built on the hold-out predictions in the previous training step using the optimal tuning parameters. The logistic regression model is then applied to the test set. The distribution of affected/unaffected subjects based on a cross-validated model using the clinical predictions and selected and filtered SNPs predictions for the random forest models is presented in Table 26, where Y-axis indicates predicted affected/unaffected subjects and X-axis indicates observed affected/unaffected subjects. FIG. 35 depicts an example diagram showing a ROC curve based on clinical predictions and selected and filtered SNPs predictions using a model for the random forest models. Table 27 includes prediction data of the mode-based ensemble approach from calculation based on a model of the model probabilities for the random forest models.

TABLE 26

|  | Affected | Unaffected |
| --- | --- | --- |
| Affected | 20 | 9 |
| Unaffected | 15 | 4 |

TABLE 27

| Observed | Clinical | Selected | Filtered | Model | Model Pred |
| --- | --- | --- | --- | --- | --- |
| Affected | 0.36 | 0.39 | 0.46 | 0.00 | Unaffected |
| Affected | 0.84 | 0.44 | 0.57 | 1.00 | Affected |
| Affected | 0.82 | 0.22 | 0.48 | 0.00 | Unaffected |
| Affected | 0.49 | 0.59 | 0.46 | 0.00 | Unaffected |
| Affected | 0.58 | 0.45 | 0.50 | 0.00 | Unaffected |
| Affected | 0.62 | 0.26 | 0.59 | 1.00 | Affected |
| Affected | 0.33 | 0.50 | 0.53 | 0.01 | Unaffected |
| Affected | 0.38 | 0.10 | 0.58 | 1.00 | Affected |
| Unaffected | 0.26 | 0.72 | 0.50 | 0.00 | Unaffected |
| Unaffected | 0.26 | 0.56 | 0.51 | 0.00 | Unaffected |
| Affected | 0.39 | 0.50 | 0.57 | 1.00 | Affected |
| Unaffected | 0.28 | 0.62 | 0.64 | 1.00 | Affected |
| Affected | 0.36 | 0.55 | 0.52 | 0.00 | Unaffected |
| Unaffected | 0.42 | 0.50 | 0.54 | 1.00 | Affected |
| Unaffected | 0.38 | 0.33 | 0.46 | 0.00 | Unaffected |
| Affected | 0.70 | 0.76 | 0.50 | 0.00 | Unaffected |
| Affected | 0.42 | 0.31 | 0.50 | 0.00 | Unaffected |
| Affected | 0.36 | 0.38 | 0.46 | 0.00 | Unaffected |
| Unaffected | 0.34 | 0.78 | 0.46 | 0.00 | Unaffected |
| Affected | 0.74 | 0.43 | 0.65 | 1.00 | Affected |
| Affected | 0.74 | 0.78 | 0.60 | 1.00 | Affected |
| Affected | 0.73 | 0.57 | 0.55 | 1.00 | Affected |
| Affected | 0.49 | 0.59 | 0.68 | 1.00 | Affected |
| Affected | 0.57 | 0.62 | 0.58 | 1.00 | Affected |
| Unaffected | 0.55 | 0.69 | 0.54 | 1.00 | Affected |
| Affected | 0.34 | 0.71 | 0.59 | 1.00 | Affected |
| Unaffected | 0.48 | 0.40 | 0.64 | 1.00 | Affected |
| Affected | 0.46 | 0.54 | 0.64 | 1.00 | Affected |
| Affected | 0.66 | 0.82 | 0.64 | 1.00 | Affected |
| Affected | 0.56 | 0.41 | 0.48 | 0.00 | Unaffected |
| Affected | 0.46 | 0.32 | 0.54 | 1.00 | Affected |
| Affected | 0.72 | 0.24 | 0.66 | 1.00 | Affected |
| Affected | 0.84 | 0.73 | 0.47 | 0.00 | Unaffected |
| Unaffected | 0.44 | 0.30 | 0.60 | 1.00 | Affected |
| Affected | 0.57 | 0.84 | 0.56 | 1.00 | Affected |
| Affected | 0.67 | 0.78 | 0.52 | 1.00 | Affected |
| Affected | 0.74 | 0.66 | 0.63 | 1.00 | Affected |
| Affected | 0.50 | 0.90 | 0.55 | 1.00 | Affected |
| Affected | 0.72 | 0.39 | 0.65 | 1.00 | Affected |
| Unaffected | 0.65 | 0.23 | 0.53 | 1.00 | Affected |
| Unaffected | 0.42 | 0.64 | 0.53 | 0.67 | Affected |
| Unaffected | 0.38 | 0.50 | 0.66 | 1.00 | Affected |
| Unaffected | 0.58 | 0.47 | 0.56 | 1.00 | Affected |
| Affected | 0.34 | 0.47 | 0.51 | 0.00 | Unaffected |
| Affected | 0.38 | 0.48 | 0.62 | 1.00 | Affected |
| Affected | 0.68 | 0.56 | 0.46 | 0.00 | Unaffected |
| Affected | 0.84 | 0.36 | 0.50 | 0.00 | Unaffected |
| Affected | 0.56 | 0.48 | 0.50 | 0.00 | Unaffected |

Figure 36:
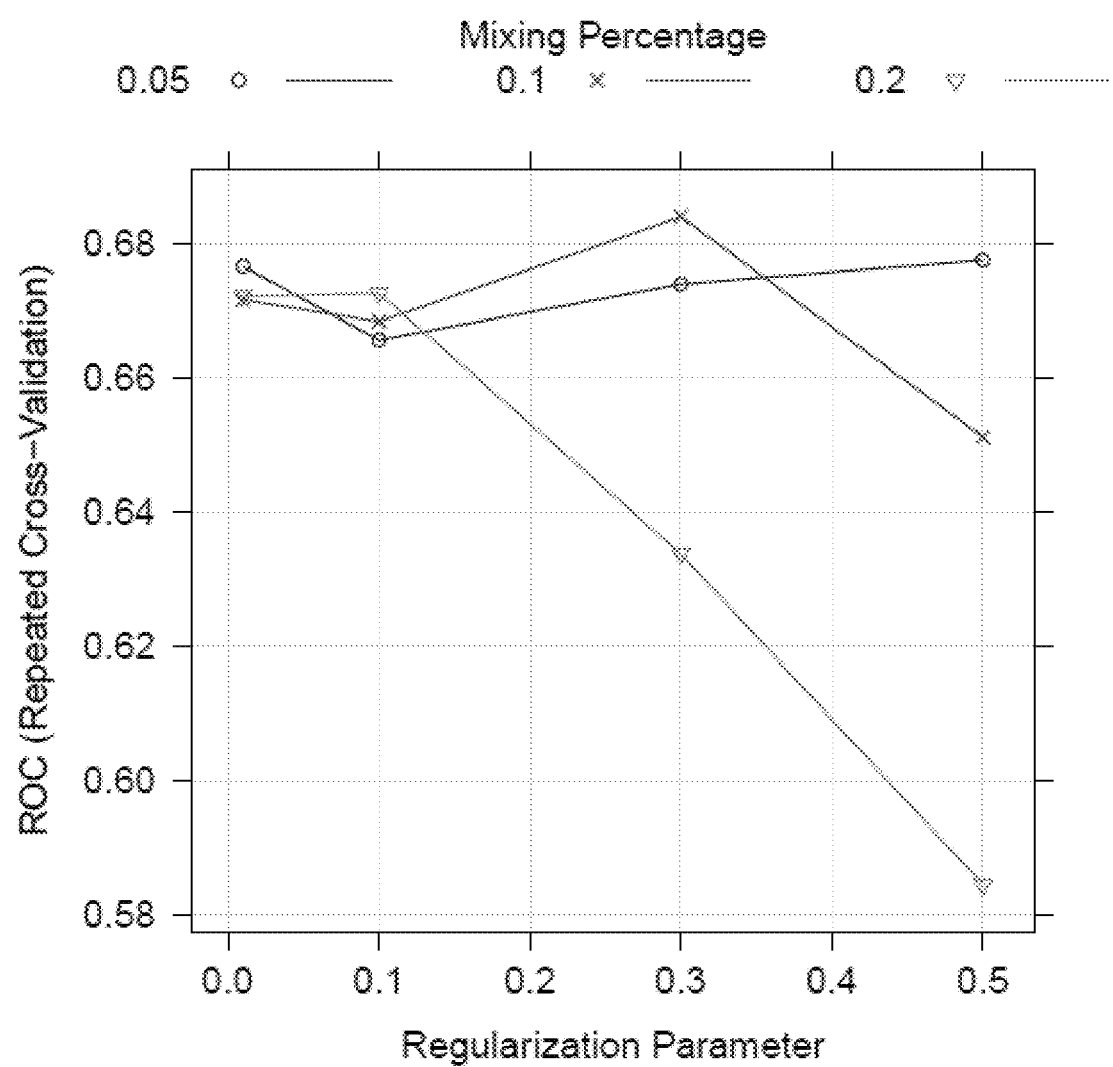

6.3.3 Penalized Logistic Regression
6.3.3.1 Clinical Predictors
FIG. 36 depicts an example diagram showing the tuning parameter profile for the penalized logistic model related to clinical predictors. The optimal mixing percentage for this data is 0.1 and the optimal regularization parameter is 0.3. The distribution of affected/unaffected subjects for the penalized logistic regression model is presented in Table 28, where Y-axis indicates predicted affected/unaffected subjects and X-axis indicates observed affected/unaffected subjects.

TABLE 28

|  | Affected | Unaffected |
| --- | --- | --- |
| Affected | 21 | 2 |
| Unaffected | 14 | 11 |

Figure 37:
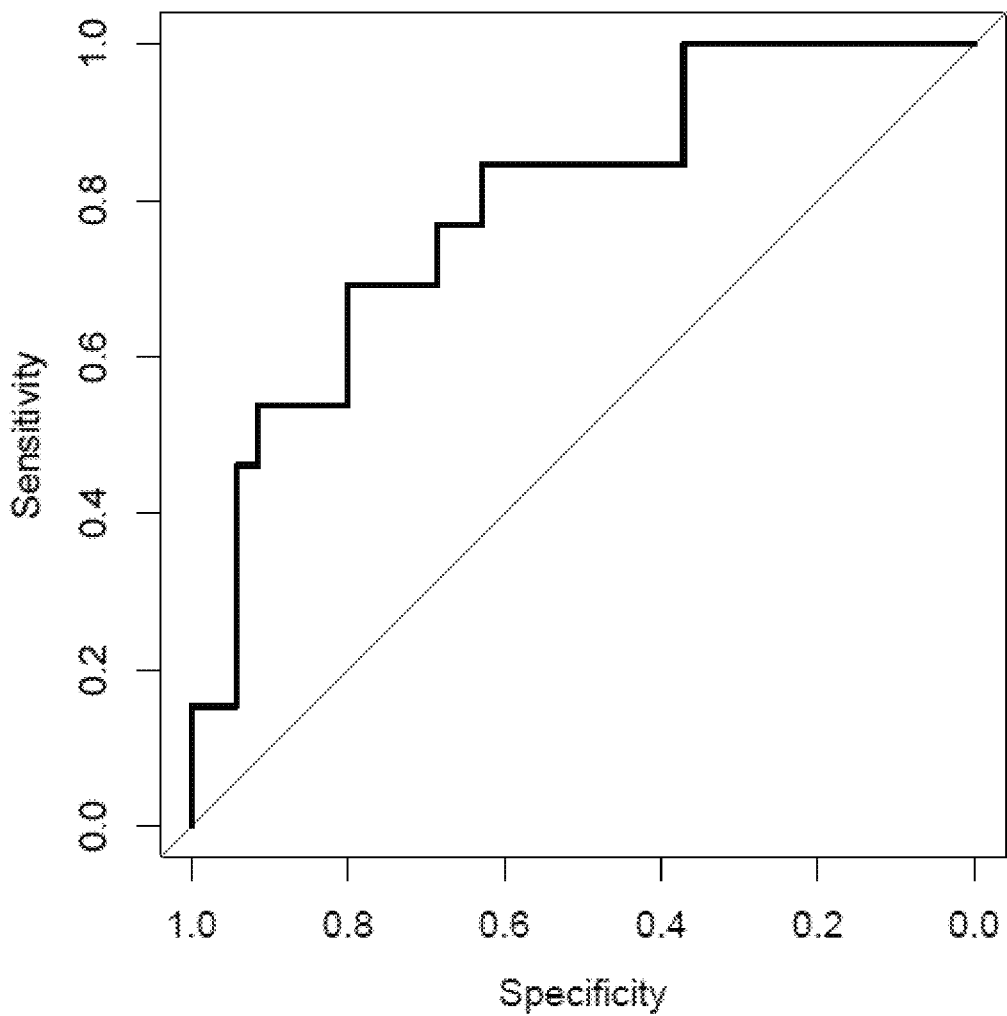
Figure 38:
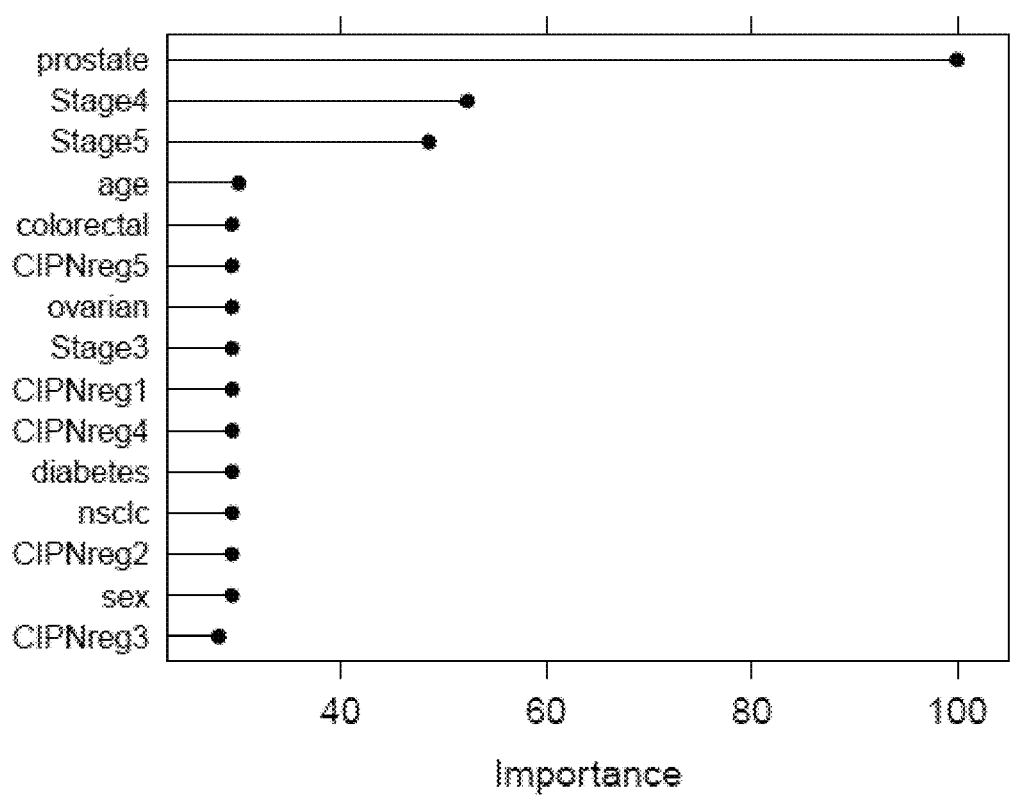

FIG. 37 depicts an example diagram showing a penalized logistic regression test set ROC curve related to the clinical predictors. FIG. 38 depicts an example diagram showing penalized logistic regression top important predictors among the clinical predictors.

6.3.3.2 Selected SNPs

Figure 39:
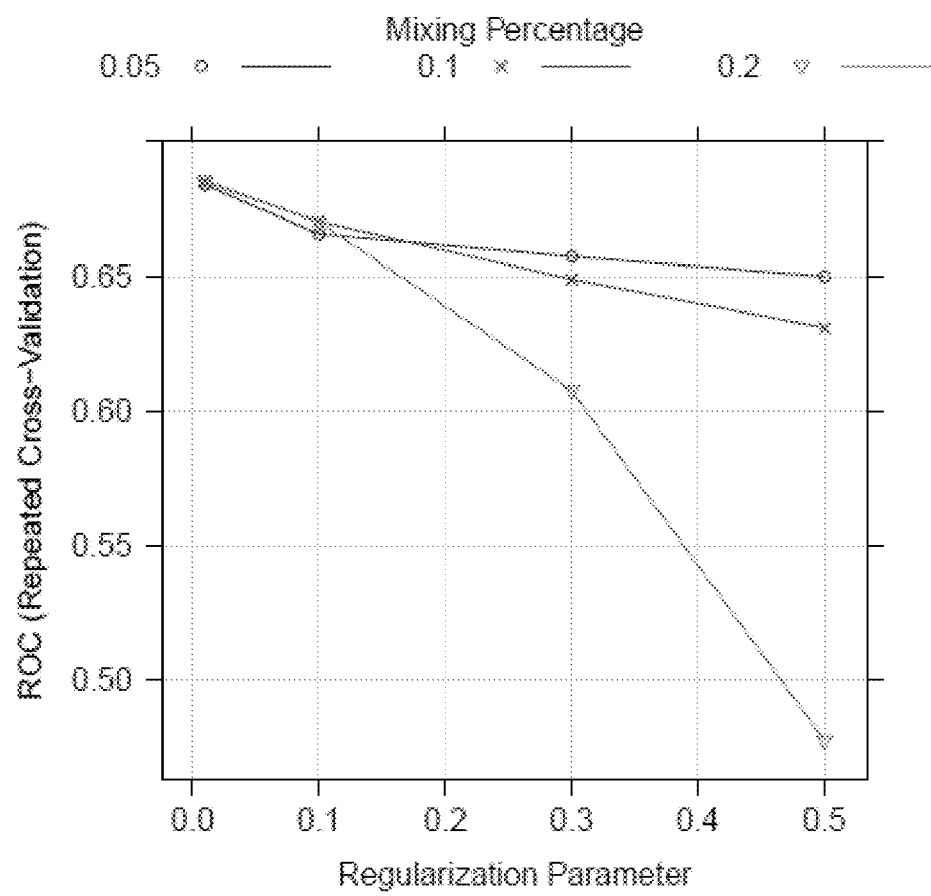

FIG. 39 depicts an example diagram showing the tuning parameter profile for the penalized logistic regression model related to the selected SNPs. The optimal mixing percentage for this data is 0.2 and the optimal regularization parameter is 0.01. The distribution of affected/unaffected subjects based on the selected SNPs for the penalized logistic regression model is presented in Table 29, where Y-axis indicates predicted affected/unaffected subjects and X-axis indicates observed affected/unaffected subjects.

TABLE 29

|  | Affected | Unaffected |
| --- | --- | --- |
| Affected | 19 | 10 |
| Unaffected | 16 | 3 |

Figure 40:
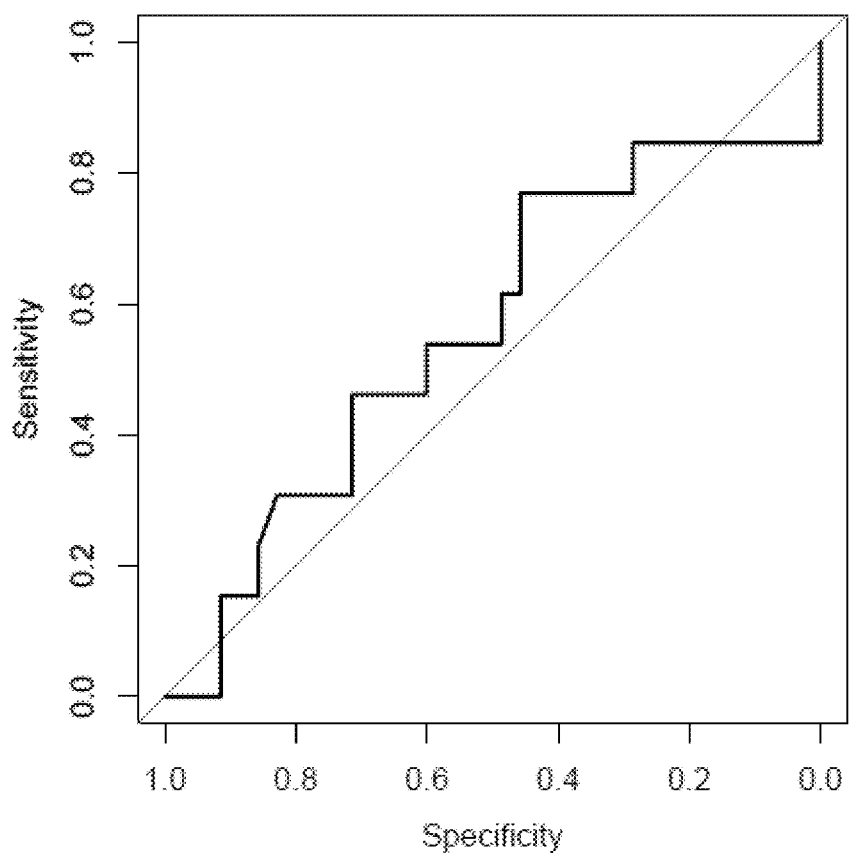
Figure 41:
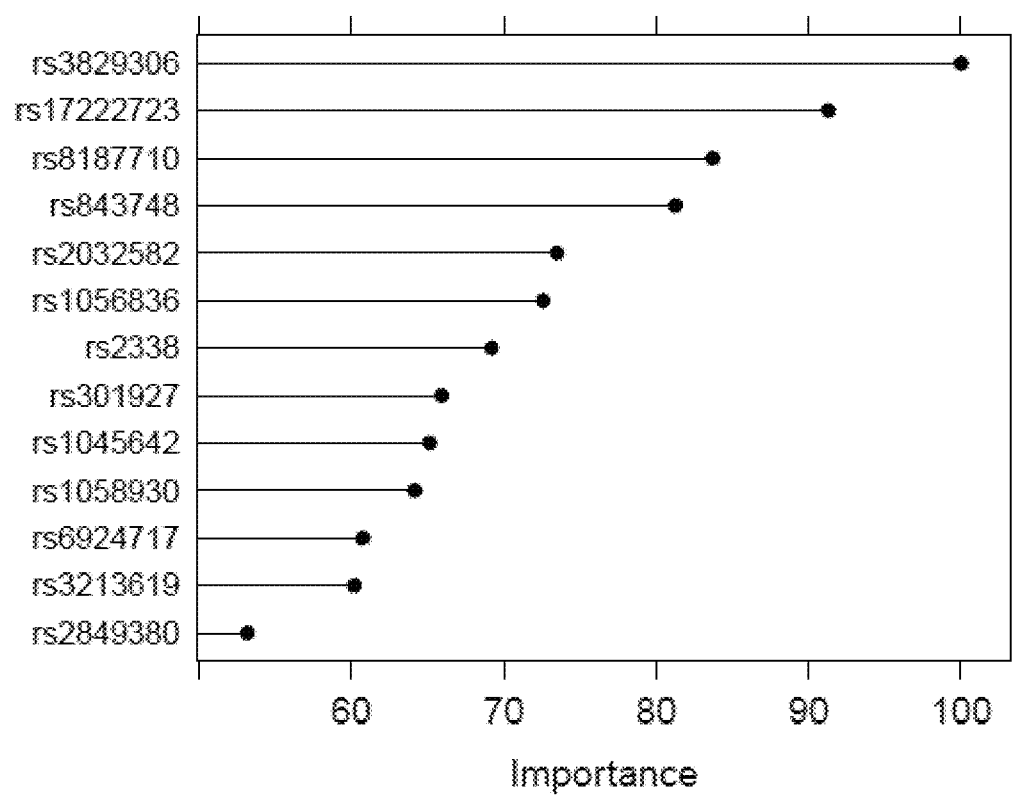

FIG. 40 depicts an example diagram showing a penalized logistic regression test set ROC curve related to the selected SNPs. FIG. 41 depicts an example diagram showing penalized logistic regression top important predictors among the selected SNPs.

Figure 42:
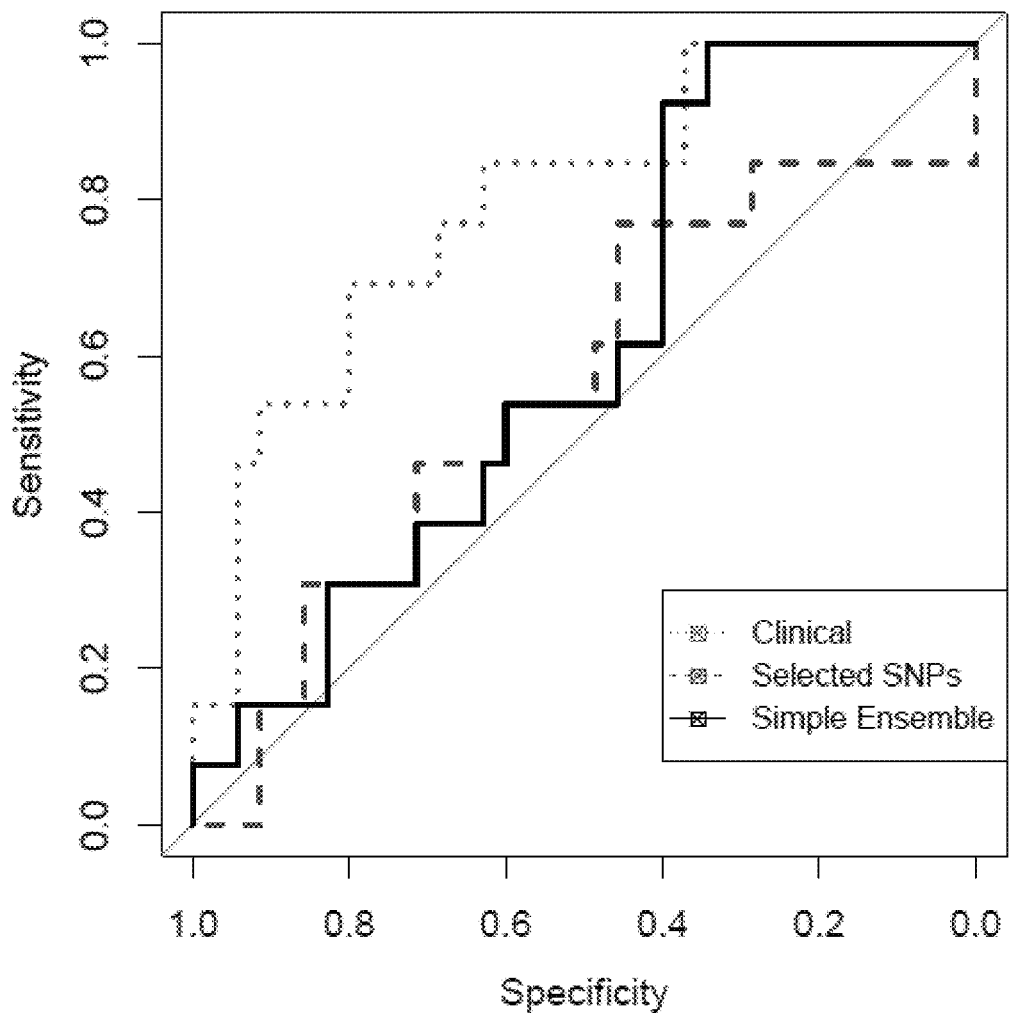

6.3.3.3 Simple Ensemble Approach: Clinical Predictions and Selected SNPs Predictions A simple ensemble approach is applied to determine a simple average of test set predicted probabilities to classify subjects into the affected and unaffected categories. FIG. 42 depicts an example diagram showing a ROC curve based on the average of clinical predictions and selected SNPs predictions for the penalized logistic regression model. The distribution of affected/unaffected subjects based on the simple ensemble approach for the penalized logistic regression model is presented in Table 30, where Y-axis indicates predicted affected/unaffected subjects and X-axis indicates observed affected/unaffected subjects. Table 31 includes prediction data of the simple ensemble approach from calculation based on an average of the model probabilities for penalized logistic regression models.

TABLE 30

|  | Affected | Unaffected |
| --- | --- | --- |
| Affected | 21 | 7 |
| Unaffected | 14 | 6 |

TABLE 31

| Observed | Clinical | Selected | Ensemble | Ensemble Pred |
|---|---|---|---|---|
| Affected | 0.46 | 0.47 | 0.47 | Unaffected |
| Affected | 0.57 | 0.60 | 0.58 | Affected |
| Affected | 0.52 | 0.23 | 0.37 | Unaffected |
| Affected | 0.51 | 0.49 | 0.50 | Affected |
| Affected | 0.47 | 0.48 | 0.47 | Unaffected |
| Affected | 0.55 | 0.42 | 0.48 | Unaffected |
| Affected | 0.46 | 0.18 | 0.32 | Unaffected |
| Affected | 0.46 | 0.54 | 0.50 | Unaffected |
| Unaffected | 0.34 | 0.51 | 0.42 | Unaffected |
| Unaffected | 0.33 | 0.58 | 0.46 | Unaffected |
| Affected | 0.48 | 0.47 | 0.48 | Unaffected |
| Unaffected | 0.44 | 0.51 | 0.47 | Unaffected |
| Affected | 0.48 | 0.68 | 0.58 | Affected |
| Unaffected | 0.47 | 0.06 | 0.27 | Unaffected |
| Unaffected | 0.47 | 0.53 | 0.50 | Affected |
| Affected | 0.51 | 0.43 | 0.47 | Unaffected |
| Affected | 0.50 | 0.23 | 0.37 | Unaffected |
| Affected | 0.44 | 0.22 | 0.33 | Unaffected |
| Unaffected | 0.44 | 0.64 | 0.54 | Affected |
| Affected | 0.57 | 0.54 | 0.55 | Affected |
| Affected | 0.50 | 0.54 | 0.52 | Affected |
| Affected | 0.58 | 0.47 | 0.52 | Affected |
| Affected | 0.51 | 0.56 | 0.53 | Affected |
| Affected | 0.51 | 0.71 | 0.61 | Affected |
| Unaffected | 0.46 | 0.61 | 0.53 | Affected |
| Affected | 0.50 | 0.52 | 0.51 | Affected |
| Unaffected | 0.51 | 0.56 | 0.53 | Affected |
| Affected | 0.44 | 0.65 | 0.54 | Affected |
| Affected | 0.53 | 0.59 | 0.56 | Affected |
| Affected | 0.51 | 0.59 | 0.55 | Affected |
| Affected | 0.48 | 0.22 | 0.35 | Unaffected |
| Affected | 0.57 | 0.47 | 0.52 | Affected |
| Affected | 0.56 | 0.56 | 0.56 | Affected |
| Unaffected | 0.51 | 0.46 | 0.49 | Unaffected |
| Affected | 0.48 | 0.57 | 0.53 | Affected |
| Affected | 0.52 | 0.59 | 0.55 | Affected |
| Affected | 0.56 | 0.58 | 0.57 | Affected |
| Affected | 0.50 | 0.62 | 0.56 | Affected |
| Affected | 0.55 | 0.20 | 0.38 | Unaffected |
| Unaffected | 0.50 | 0.17 | 0.33 | Unaffected |
| Unaffected | 0.48 | 0.58 | 0.53 | Affected |
| Unaffected | 0.45 | 0.64 | 0.54 | Affected |
| Unaffected | 0.45 | 0.61 | 0.53 | Affected |
| Affected | 0.48 | 0.61 | 0.54 | Affected |
| Affected | 0.46 | 0.63 | 0.54 | Affected |
| Affected | 0.49 | 0.42 | 0.46 | Unaffected |
| Affected | 0.51 | 0.42 | 0.46 | Unaffected |
| Affected | 0.58 | 0.57 | 0.58 | Affected |

Figure 43:
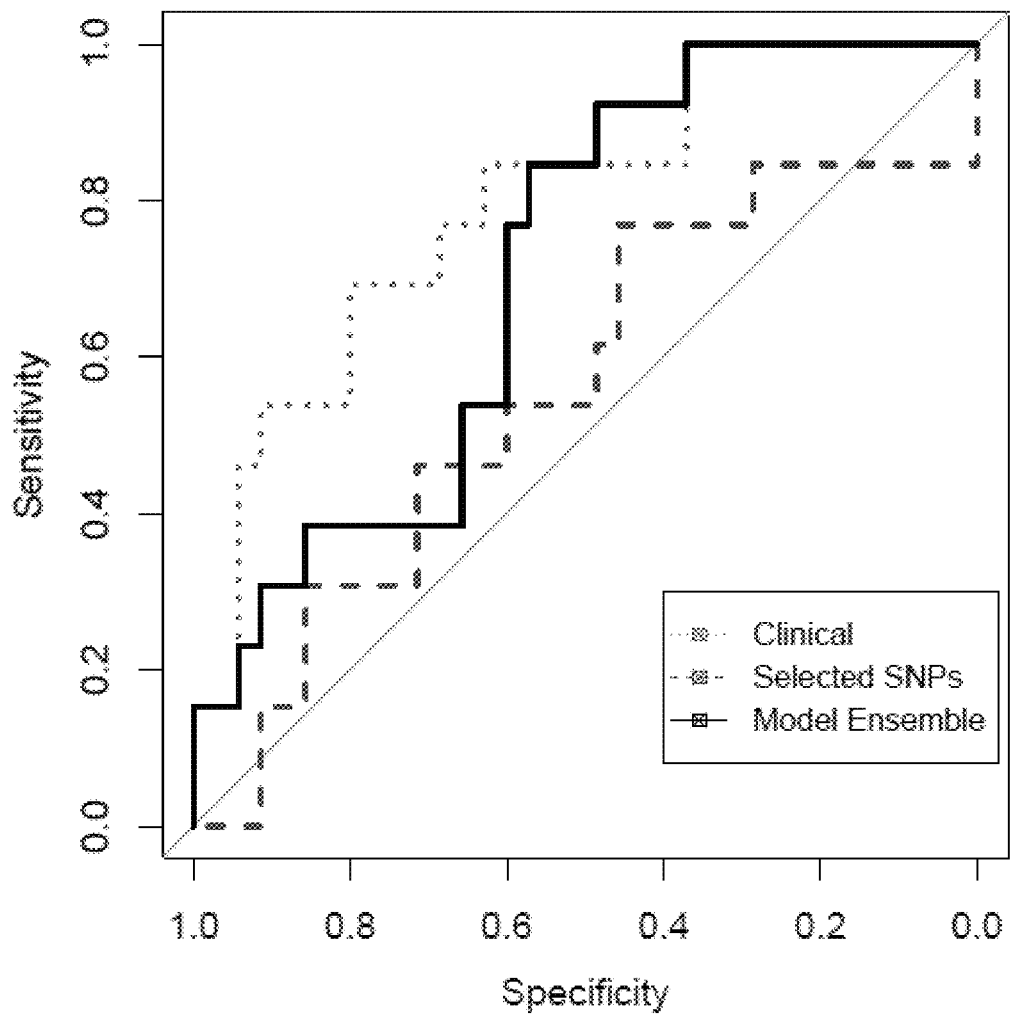

6.3.3.4 Model-Based Ensemble Approach: Clinical Predictions and Selected SNPs Predictions A logistic regression model is built on the hold-out datasets in the previous training step using the optimal tuning parameters. The logistic regression model is then applied to the test set. The distribution of affected/unaffected subjects based on a cross-validated model using the clinical predictions and selected SNPs predictions from penalized logistic regression models is presented in Table 32, where Y-axis indicates predicted affected/unaffected subjects and X-axis indicates observed affected/unaffected subjects. FIG. 43 depicts an example diagram showing a ROC curve based on clinical predictions and selected SNPs predictions using a model based on the penalized logistic regression models. Table 33 includes prediction data of the mode-based ensemble approach from calculation based on a model of the model probabilities for the penalized logistic regression models.

TABLE 32

|  | Affected | Unaffected |
|---|---|---|
| Affected | 15 | 11 |
| Unaffected | 20 | 2 |

TABLE 33

| Observed | Clinical | Selected | Model | Model Pred |
|---|---|---|---|---|
| Affected | 0.46 | 0.47 | 0.60 | Affected |
| Affected | 0.57 | 0.60 | 0.33 | Unaffected |
| Affected | 0.52 | 0.23 | 0.64 | Affected |
| Affected | 0.51 | 0.49 | 0.50 | Unaffected |
| Affected | 0.47 | 0.48 | 0.58 | Affected |
| Affected | 0.55 | 0.42 | 0.48 | Unaffected |
| Affected | 0.46 | 0.18 | 0.76 | Affected |
| Affected | 0.46 | 0.54 | 0.56 | Affected |
| Unaffected | 0.34 | 0.51 | 0.77 | Affected |
| Unaffected | 0.33 | 0.58 | 0.74 | Affected |
| Affected | 0.48 | 0.48 | 0.57 | Affected |
| Unaffected | 0.44 | 0.50 | 0.61 | Affected |
| Affected | 0.48 | 0.68 | 0.43 | Unaffected |
| Unaffected | 0.47 | 0.06 | 0.79 | Affected |
| Unaffected | 0.47 | 0.53 | 0.54 | Affected |
| Affected | 0.51 | 0.43 | 0.54 | Affected |
| Affected | 0.50 | 0.23 | 0.66 | Affected |
| Affected | 0.44 | 0.22 | 0.76 | Affected |
| Unaffected | 0.44 | 0.64 | 0.53 | Affected |
| Affected | 0.57 | 0.54 | 0.37 | Unaffected |
| Affected | 0.50 | 0.54 | 0.47 | Unaffected |
| Affected | 0.58 | 0.47 | 0.39 | Unaffected |
| Affected | 0.51 | 0.56 | 0.46 | Unaffected |
| Affected | 0.51 | 0.71 | 0.36 | Unaffected |
| Unaffected | 0.46 | 0.61 | 0.52 | Affected |
| Affected | 0.50 | 0.52 | 0.49 | Unaffected |
| Unaffected | 0.51 | 0.56 | 0.45 | Unaffected |
| Affected | 0.44 | 0.65 | 0.53 | Affected |
| Affected | 0.53 | 0.59 | 0.41 | Unaffected |
| Affected | 0.51 | 0.59 | 0.44 | Unaffected |
| Affected | 0.48 | 0.22 | 0.71 | Affected |
| Affected | 0.57 | 0.47 | 0.40 | Unaffected |
| Affected | 0.56 | 0.57 | 0.36 | Unaffected |
| Unaffected | 0.51 | 0.46 | 0.51 | Affected |
| Affected | 0.48 | 0.58 | 0.49 | Unaffected |
| Affected | 0.52 | 0.59 | 0.42 | Unaffected |
| Affected | 0.56 | 0.58 | 0.36 | Unaffected |
| Affected | 0.50 | 0.62 | 0.44 | Unaffected |
| Affected | 0.55 | 0.20 | 0.60 | Affected |
| Unaffected | 0.50 | 0.17 | 0.70 | Affected |
| Unaffected | 0.48 | 0.58 | 0.49 | Unaffected |
| Unaffected | 0.45 | 0.64 | 0.51 | Affected |
| Unaffected | 0.45 | 0.61 | 0.54 | Affected |
| Affected | 0.48 | 0.61 | 0.48 | Unaffected |
| Affected | 0.45 | 0.63 | 0.51 | Affected |
| Affected | 0.50 | 0.42 | 0.56 | Affected |
| Affected | 0.51 | 0.42 | 0.55 | Affected |
| Affected | 0.58 | 0.58 | 0.32 | Unaffected |

6.3.3.5 Filtered SNPs

Figure 44:
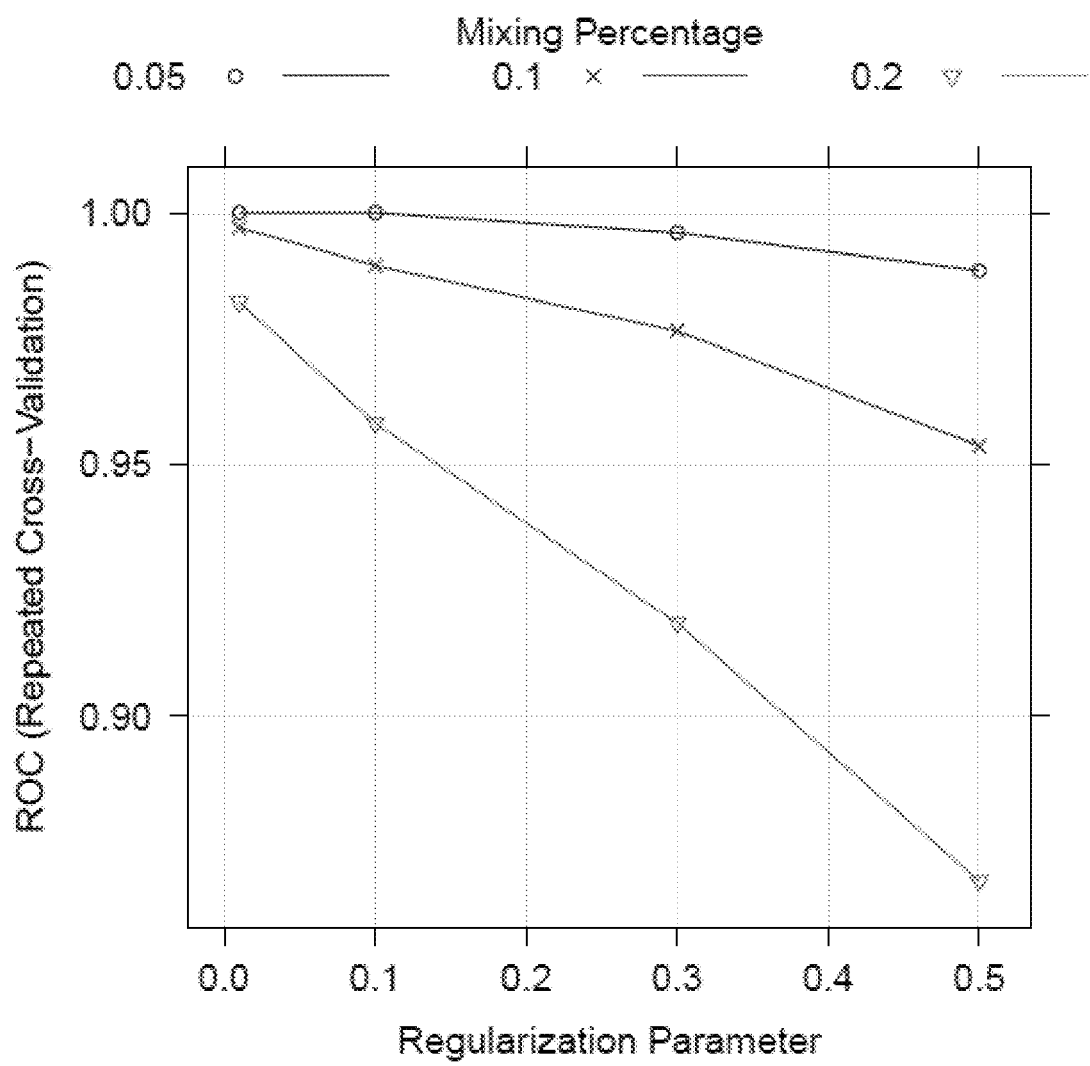
Figure 45:
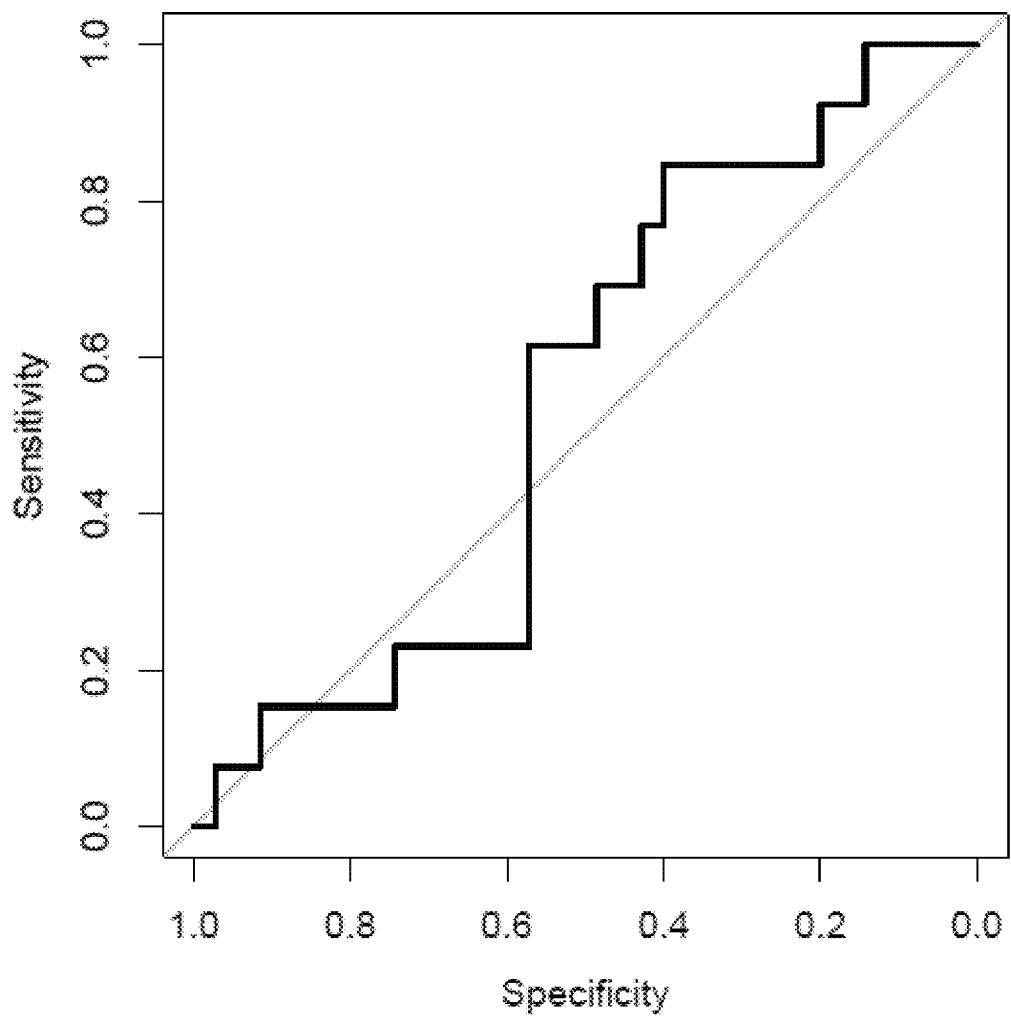
Figure 46:
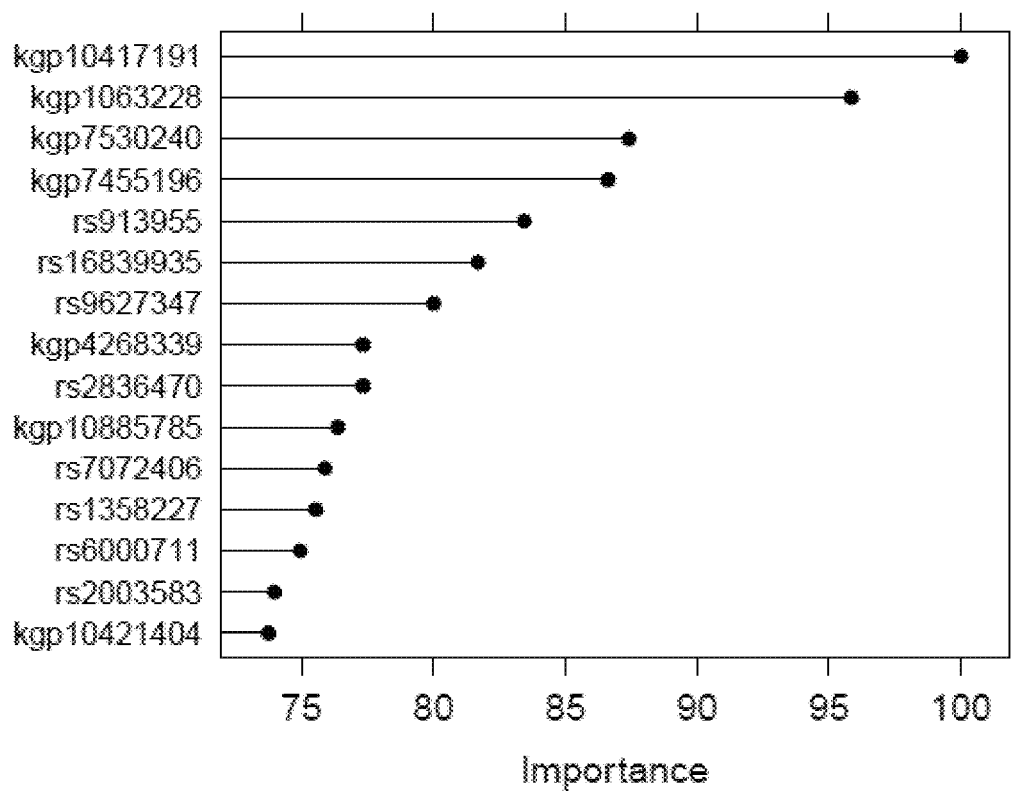

FIG. 44 depicts an example diagram showing the tuning parameter profile for the penalized logistic regression model related to the filtered SNPs. The cross-validated ROC is high in FIG. 44, indicating that it may be over-fitting, likely due to a high proportion of irrelevant predictors. The optimal mixing percentage for this data is 0.05 and the optimal regularization parameter is 0.1. The distribution of affected/unaffected subjects based on the filtered SNPs for the penalized logistic regression model is presented in Table 34, where Y-axis indicates predicted affected/unaffected subjects and X-axis indicates observed affected/unaffected subjects. FIG. 45 depicts an example diagram showing a penalized logistic regression test set ROC curve related to the filtered SNPs. FIG. 46 depicts an example diagram showing penalized logistic regression top important predictors among the filtered SNPs.

TABLE 34

|  | Affected | Unaffected |
|---|---|---|
| Affected | 26 | 10 |
| Unaffected | 9 | 3 |

6.3.3.6 Simple Ensemble Approach: Clinical Predictions, Selected and Filtered SNPs Predictions A simple ensemble approach is applied to determine a simple average of test set predicted probabilities to classify subjects into the affected and unaffected categories. The distribution of affected/unaffected subjects based on the average of clinical predictions and selected and filtered SNPs predictions for penalized logistic regression models is presented in Table 35, where Y-axis indicates predicted affected/unaffected subjects and X-axis indicates observed affected/unaffected subjects.

TABLE 35

|  | Affected | Unaffected |
|---|---|---|
| Affected | 27 | 9 |
| Unaffected | 8 | 4 |

Figure 47:
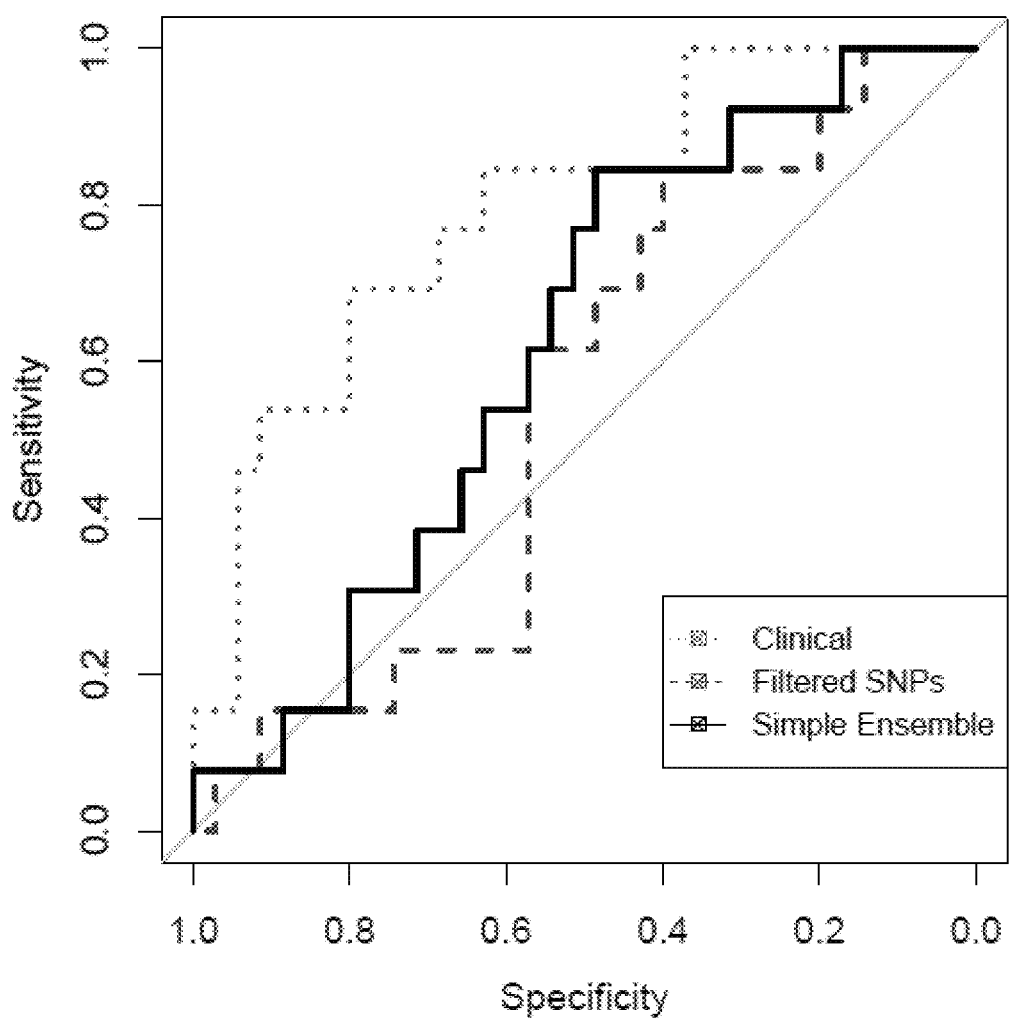

FIG. 47 depicts an example diagram showing a ROC curve based on the average of clinical predictions and selected and filtered SNPs predictions for penalized logistic regression models. Table 36 includes prediction data of the simple ensemble approach from calculation based on an average of the model probabilities for penalized logistic regression models.

TABLE 36

| Observed | Clinical | Selected | Filtered | Ensemble | Ensemble Pred |
|---|---|---|---|---|---|
| Affected | 0.46 | 0.47 | 0.63 | 0.52 | Affected |
| Affected | 0.57 | 0.60 | 0.86 | 0.68 | Affected |
| Affected | 0.52 | 0.23 | 0.39 | 0.38 | Unaffected |
| Affected | 0.51 | 0.49 | 0.54 | 0.52 | Affected |
| Affected | 0.47 | 0.48 | 0.35 | 0.43 | Unaffected |
| Affected | 0.55 | 0.42 | 0.75 | 0.57 | Affected |
| Affected | 0.46 | 0.18 | 0.59 | 0.41 | Unaffected |
| Affected | 0.46 | 0.54 | 0.81 | 0.60 | Affected |
| Unaffected | 0.34 | 0.51 | 0.60 | 0.48 | Unaffected |
| Unaffected | 0.33 | 0.58 | 0.60 | 0.51 | Affected |
| Affected | 0.48 | 0.47 | 0.57 | 0.51 | Affected |
| Unaffected | 0.44 | 0.51 | 0.89 | 0.61 | Affected |
| Affected | 0.48 | 0.68 | 0.72 | 0.63 | Affected |
| Unaffected | 0.47 | 0.06 | 0.39 | 0.31 | Unaffected |
| Unaffected | 0.47 | 0.53 | 0.33 | 0.44 | Unaffected |
| Affected | 0.51 | 0.43 | 0.41 | 0.45 | Unaffected |
| Affected | 0.50 | 0.23 | 0.64 | 0.46 | Unaffected |
| Affected | 0.44 | 0.22 | 0.55 | 0.40 | Unaffected |
| Unaffected | 0.44 | 0.64 | 0.47 | 0.52 | Affected |
| Affected | 0.57 | 0.54 | 0.91 | 0.67 | Affected |
| Affected | 0.50 | 0.54 | 0.92 | 0.66 | Affected |
| Affected | 0.58 | 0.47 | 0.75 | 0.60 | Affected |
| Affected | 0.51 | 0.56 | 0.96 | 0.68 | Affected |
| Affected | 0.51 | 0.71 | 0.95 | 0.73 | Affected |
| Unaffected | 0.46 | 0.61 | 0.47 | 0.51 | Affected |
| Affected | 0.50 | 0.52 | 0.74 | 0.59 | Affected |
| Unaffected | 0.51 | 0.56 | 0.62 | 0.56 | Affected |
| Affected | 0.44 | 0.65 | 0.83 | 0.64 | Affected |
| Affected | 0.53 | 0.59 | 0.89 | 0.67 | Affected |
| Affected | 0.51 | 0.59 | 0.54 | 0.55 | Affected |
| Affected | 0.48 | 0.22 | 0.86 | 0.52 | Affected |
| Affected | 0.57 | 0.47 | 0.74 | 0.59 | Affected |
| Affected | 0.56 | 0.56 | 0.41 | 0.51 | Affected |
| Unaffected | 0.51 | 0.46 | 0.60 | 0.52 | Affected |
| Affected | 0.48 | 0.57 | 0.49 | 0.52 | Affected |
| Affected | 0.52 | 0.59 | 0.39 | 0.50 | Affected |
| Affected | 0.56 | 0.58 | 0.96 | 0.70 | Affected |

TABLE 36-continued

| Observed | Clinical | Selected | Filtered | Ensemble | Ensemble Pred |
|---|---|---|---|---|---|
| Affected | 0.50 | 0.62 | 0.82 | 0.64 | Affected |
| Affected | 0.55 | 0.20 | 0.76 | 0.50 | Affected |
| Unaffected | 0.50 | 0.17 | 0.71 | 0.46 | Unaffected |
| Unaffected | 0.48 | 0.58 | 0.60 | 0.56 | Affected |
| Unaffected | 0.45 | 0.64 | 0.90 | 0.66 | Affected |
| Unaffected | 0.45 | 0.61 | 0.50 | 0.52 | Affected |
| Affected | 0.48 | 0.61 | 0.62 | 0.57 | Affected |
| Affected | 0.46 | 0.63 | 0.89 | 0.66 | Affected |
| Affected | 0.49 | 0.42 | 0.76 | 0.56 | Affected |
| Affected | 0.51 | 0.42 | 0.57 | 0.50 | Unaffected |
| Affected | 0.58 | 0.57 | 0.20 | 0.45 | Unaffected |

Figure 48:
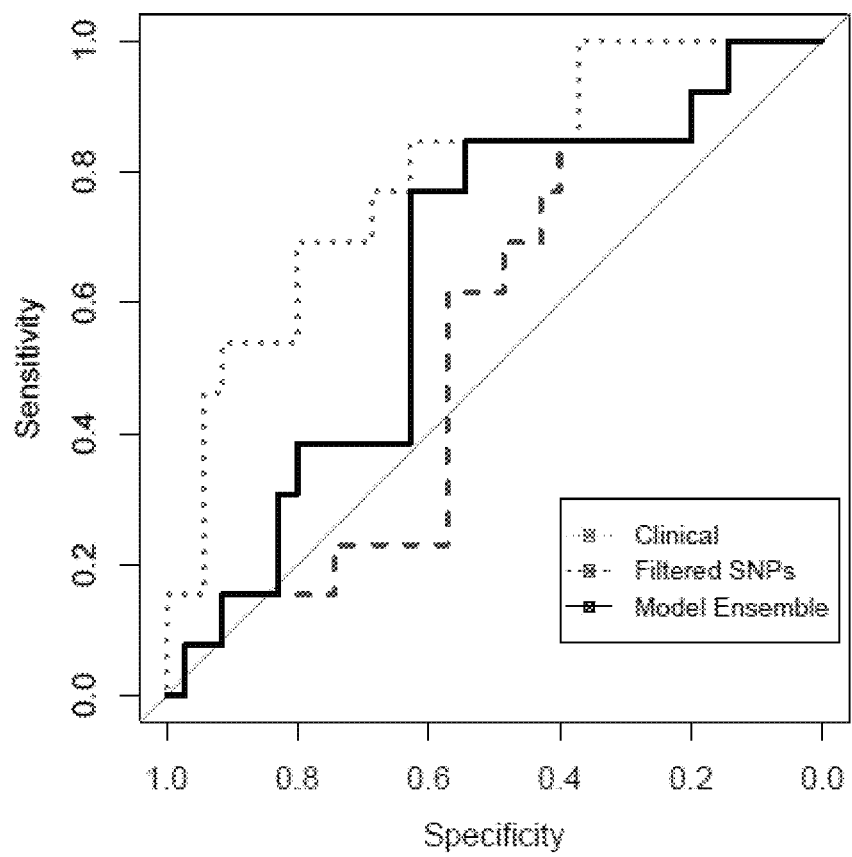

6.3.3.7 Model-Based Ensemble Approach: Clinical Predictions, Selected and Filtered SNPs Predictions A logistic regression model is built on the hold-out datasets in the previous training step using the optimal tuning parameters. The logistic regression model is then applied to the test set. The distribution of affected/unaffected subjects based on a cross-validated model using the clinical predictions and selected and filtered SNPs predictions for the penalized logistic regression models is presented in Table 37, where Y-axis indicates predicted affected/unaffected subjects and X-axis indicates observed affected/unaffected subjects. FIG. 48 depicts an example diagram showing a ROC curve based on clinical predictions and selected and filtered SNPs predictions using a model for the penalized logistic regression models. Table 38 includes prediction data of the mode-based ensemble approach from calculation based on a model of the model probabilities for the penalized logistic regression models.

TABLE 37

|  | Affected | Unaffected |
|---|---|---|
| Affected | 28 | 8 |
| Unaffected | 7 | 5 |

TABLE 38

| Observed | Clinical | Selected | Filtered | Model | Model Pred |
|---|---|---|---|---|---|
| Affected | 0.46 | 0.47 | 0.63 | 0.51 | Affected |
| Affected | 0.57 | 0.60 | 0.86 | 0.51 | Affected |
| Affected | 0.52 | 0.23 | 0.39 | 0.50 | Unaffected |
| Affected | 0.51 | 0.49 | 0.54 | 0.50 | Affected |
| Affected | 0.47 | 0.48 | 0.35 | 0.49 | Unaffected |
| Affected | 0.55 | 0.42 | 0.75 | 0.51 | Affected |
| Affected | 0.46 | 0.18 | 0.59 | 0.50 | Affected |
| Affected | 0.46 | 0.54 | 0.81 | 0.51 | Affected |
| Unaffected | 0.34 | 0.51 | 0.60 | 0.50 | Affected |
| Unaffected | 0.33 | 0.58 | 0.60 | 0.50 | Affected |
| Affected | 0.48 | 0.48 | 0.57 | 0.50 | Affected |
| Unaffected | 0.44 | 0.50 | 0.88 | 0.52 | Affected |
| Affected | 0.48 | 0.68 | 0.72 | 0.51 | Affected |
| Unaffected | 0.47 | 0.06 | 0.39 | 0.50 | Unaffected |
| Unaffected | 0.47 | 0.53 | 0.33 | 0.49 | Unaffected |
| Affected | 0.51 | 0.43 | 0.41 | 0.50 | Unaffected |
| Affected | 0.50 | 0.23 | 0.64 | 0.51 | Affected |
| Affected | 0.44 | 0.22 | 0.55 | 0.50 | Affected |
| Unaffected | 0.44 | 0.64 | 0.47 | 0.50 | Unaffected |
| Affected | 0.57 | 0.54 | 0.91 | 0.52 | Affected |
| Affected | 0.50 | 0.54 | 0.92 | 0.52 | Affected |
| Affected | 0.58 | 0.47 | 0.75 | 0.51 | Affected |
| Affected | 0.51 | 0.56 | 0.96 | 0.52 | Affected |
| Affected | 0.51 | 0.71 | 0.95 | 0.52 | Affected |
| Unaffected | 0.46 | 0.61 | 0.47 | 0.50 | Unaffected |
| Affected | 0.50 | 0.52 | 0.74 | 0.51 | Affected |
| Unaffected | 0.51 | 0.58 | 0.62 | 0.50 | Affected |
| Affected | 0.44 | 0.65 | 0.83 | 0.51 | Affected |

TABLE 38-continued

| Observed | Clinical | Selected | Filtered | Model | Model Pred |
|---|---|---|---|---|---|
| Affected | 0.53 | 0.59 | 0.89 | 0.52 | Affected |
| Affected | 0.51 | 0.59 | 0.54 | 0.50 | Affected |
| Affected | 0.48 | 0.22 | 0.86 | 0.51 | Affected |
| Affected | 0.57 | 0.47 | 0.74 | 0.51 | Affected |
| Affected | 0.56 | 0.57 | 0.41 | 0.50 | Unaffected |
| Unaffected | 0.51 | 0.46 | 0.60 | 0.50 | Affected |
| Affected | 0.48 | 0.58 | 0.49 | 0.50 | Unaffected |
| Affected | 0.52 | 0.59 | 0.39 | 0.50 | Unaffected |
| Affected | 0.56 | 0.58 | 0.96 | 0.52 | Affected |
| Affected | 0.50 | 0.62 | 0.82 | 0.51 | Affected |
| Affected | 0.55 | 0.20 | 0.76 | 0.51 | Affected |
| Unaffected | 0.50 | 0.17 | 0.71 | 0.51 | Affected |
| Unaffected | 0.48 | 0.58 | 0.60 | 0.50 | Affected |
| Unaffected | 0.45 | 0.64 | 0.90 | 0.52 | Affected |
| Unaffected | 0.45 | 0.61 | 0.50 | 0.50 | Unaffected |
| Affected | 0.48 | 0.61 | 0.62 | 0.50 | Affected |
| Affected | 0.45 | 0.63 | 0.89 | 0.52 | Affected |
| Affected | 0.50 | 0.42 | 0.76 | 0.51 | Affected |
| Affected | 0.51 | 0.42 | 0.57 | 0.50 | Affected |
| Affected | 0.58 | 0.58 | 0.20 | 0.49 | Unaffected |

It should be understood that the above description only discloses several scenarios presented by this invention, and the description is relatively specific and detailed, yet it cannot therefore be understood as limiting the scope of this invention's patent. It should be noted that ordinary technicians in the field may also, without deviating from the invention's conceptual premises, make a number of variations and modifications, which are all within the scope of this invention. As a result, in terms of protection, the patent claims shall prevail.

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, various embodiments and/or examples of the present invention can be combined.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to carry out the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, etc.) that contain instructions (e.g., software) for use in execution by a processor to perform the methods' operations and implement the systems described herein.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope or of what may be claimed, but rather as descriptions of features specific to particular embodiments. Certain features that are described in this specification in the context or separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

It is claimed:

1. A processor-implemented method for predicting regimen-related outcomes, the method comprising:
    generating, using the one or more data processors, one or more training datasets and one or more testing datasets based at least in part on clinical data and gene feature data of a plurality of patients the gene feature data including data related to one or more single-nucleotide polymorphisms (SNPs), and the clinical data including diagnosis data, cancer-stage data, regimen related data, and neuropathy related data;
wherein generating one or more training datasets and one or more testing datasets based at least in part on clinical data and gene feature data of a plurality of patients includes:
determining a plurality of SNPs;
filtering the plurality of SNPs to determine one or more filtered SNPs using a recursive partitioning operation for filtering by:
dividing the gene feature dataset related to the plurality of SNPs into a plurality of sub-datasets;
selecting one or more first sub-datasets from the plurality of sub-datasets;
developing a first recursive partitioning model based at least in part on the one or more first sub-datasets;
determining one or more first predictive SNPs based at least in part on the first recursive partitioning model, wherein the one or more first predictive SNPs are included into the one or more filtered SNPs;
selecting one or more second sub-datasets from the plurality of sub-datasets;
developing a second recursive partitioning model based at least in part on the one or more second sub-datasets; and
determining one or more second predictive SNPs based at least in part on the second recursive partitioning model, wherein the one or more second predictive SNPs are included into the one or more filtered SNPs; and
determining the gene feature data based at least in part on the one or more filtered SNPs;
determining, using one or more data processors, one or more initial predictive models using one or more machine learning algorithms based at least in part on the one or more training datasets;
applying, using the one or more data processors, the one or more initial predictive models on the one or more training datasets to generate result data;
performing, using the one or more data processors, an ensemble algorithm on the result data to generate ensemble data;
determining, using the one or more data processors, one or more final predictive models based at least in part on the ensemble data;
evaluating, using the one or more data processors, performance of the one or more final predictive models based at least in part on the one or more test datasets;
predicting, using the one or more data processors, regimen-related outcomes including side effects using the one or more final predictive models including likelihoods for each of a plurality of side effects;
providing a first interface for receiving indications of patient tolerances for side effects, wherein a numerical value is assigned to each of the plurality of side effects based on the received indications; and
providing a second interface that identifies the likelihoods for each of the plurality of side effects, wherein a treatment regimen for the patient is determined based on the likelihoods for each of the plurality of side effects and the numerical values assigned for each of the patient tolerances for side effects.

2. The method of claim 1, wherein generating one or more training datasets and one or more testing datasets based at least in part on clinical data or gene feature data of a plurality of patients includes:
determining the gene feature data based at least in part on one or more predetermined SNPs.

3. The method of claim 1, wherein filtering the plurality of SNPs to determine the one or more filtered SNPs includes:
removing a number of SNPs based on missing data from the plurality of SNPs.

4. The method of claim 1, wherein filtering the plurality of SNPs to determine the one or more filtered SNPs includes:
removing one or more SNPs that are associated from the plurality of SNPs.

5. The method of claim 1, wherein the one or more machine learning algorithms correspond to one or more of the following: a penalized logistic regression algorithm, a random forests algorithm, and a C5.0 algorithm.

6. The method of claim 1, wherein generating one or more training datasets and one or more testing datasets based at least in part on clinical data or gene feature data of a plurality of patients includes:
generating one or more clinical predictor datasets based at least in part on the clinical data; and
generating one or more gene feature datasets based at least in part on the gene feature data.

7. The method of claim 6, wherein applying the one or more initial predictive models on the one or more training datasets to generate result data includes:
applying the initial predictive models on the one or more clinical predictor datasets to generate clinical result data; and
applying the initial predictive models on the one or more gene feature datasets to generate gene feature result data.

8. The method of claim 1, wherein the ensemble algorithm corresponds to an average calculation or a logistic regression algorithm.

9. The method of claim 1, wherein generating one or more training datasets and one or more testing datasets based at least in part on clinical data or gene feature data of a plurality of patients includes:
generating one or more clinical predictor datasets by generating binary predictor data based at least in part on the clinical data.

10. The method of claim 1, further comprising:
performing 10-fold cross-validation on the one or more training datasets to determine one or more tuning parameters for the initial predictive models.

11. The method of claim 1, wherein the first interface displays a scale running from perfect health to death.

12. The method of claim 11, wherein low magnitude numerical values are assigned to less tolerable side effects, where a magnitude of zero is associated with death.

13. The method of claim 11, wherein the second interface further displays a scale running from perfect health to death that includes the plurality of side effects, the plurality of side effects being positioned on the scale according to the numerical values assigned to each of the plurality of side effects.

* * * * *